United States Patent
Kroth et al.

(10) Patent No.: US 9,701,660 B2
(45) Date of Patent: Jul. 11, 2017

(54) 2,6-DIAMINOPYRIDINE COMPOUNDS SUITABLE FOR TREATING DISEASES ASSOCIATED WITH AMYLOID OR AMYLOID-LIKE PROTEINS OR FOR TREATING OR PREVENTING OCULAR DISEASES OR CONDITIONS ASSOCIATED WITH A PATHOLOGICAL ABNORMALITY/CHANGE IN THE TISSUE OF THE VISUAL SYSTEM

(71) Applicant: AC Immune S.A., Lausanne (CH)

(72) Inventors: Heiko Kroth, Ecublens (CH); Wolfgang Froestl, Ecublens (CH); Andrea Pfeifer, St-Legier (CH); Andreas Muhs, Cugy (CH)

(73) Assignee: AC Immune S.A., Lausanne (CH)

( * ) Notice: Subject to any disclaimer, the term of this patent is extended or adjusted under 35 U.S.C. 154(b) by 0 days.

(21) Appl. No.: 14/502,907

(22) Filed: Sep. 30, 2014

(65) Prior Publication Data
US 2015/0023950 A1    Jan. 22, 2015

Related U.S. Application Data

(62) Division of application No. 12/905,356, filed on Oct. 15, 2010, now Pat. No. 8,916,590.

(30) Foreign Application Priority Data

Oct. 15, 2009  (EP) ..................... 09173184

(51) Int. Cl.
*A61K 31/444* (2006.01)
*C07D 401/14* (2006.01)
*C07D 471/04* (2006.01)
*G01N 33/68* (2006.01)

(52) U.S. Cl.
CPC .......... *C07D 401/14* (2013.01); *A61K 31/444* (2013.01); *C07D 471/04* (2013.01); *G01N 33/6896* (2013.01); *G01N 2333/4709* (2013.01); *G01N 2800/28* (2013.01)

(58) Field of Classification Search
CPC .................................................. A61K 31/444
USPC ......................................................... 514/332
See application file for complete search history.

(56) References Cited

U.S. PATENT DOCUMENTS

| | | | |
|---|---|---|---|
| 3,212,892 A | 10/1965 | von Konig et al. |
| 3,651,023 A | 3/1972 | Ottenheym et al. |
| 4,545,809 A | 10/1985 | Seki et al. |
| 6,385,594 B1 | 5/2002 | Lebda et al. |
| 7,105,503 B2 | 9/2006 | Zhang |
| 7,882,025 B1 | 2/2011 | Seal et al. |
| 8,244,618 B1 | 8/2012 | Fashenpour et al. |
| 8,438,096 B1 | 5/2013 | Fashenpour et al. |
| 2003/0105696 A1 | 6/2003 | Kalotay et al. |
| 2004/0205019 A1 | 10/2004 | Painter et al. |
| 2008/0109347 A1 | 5/2008 | Pilcher et al. |

FOREIGN PATENT DOCUMENTS

| | | |
|---|---|---|
| CN | 102656161 A | 9/2012 |
| EP | 0129830 A2 | 1/1985 |
| RU | 99117921 | 6/2004 |
| SU | 181121 | 4/1966 |
| SU | 400583 A1 | 10/1973 |
| WO | WO 96/14843 A2 | 5/1996 |
| WO | WO 02/078693 A2 | 10/2002 |
| WO | WO 03/013523 A1 | 2/2003 |
| WO | WO 03/040402 A2 | 5/2003 |
| WO | WO 03/045949 A1 | 6/2003 |
| WO | WO 03/080616 A1 | 10/2003 |
| WO | WO 03/095429 A1 | 11/2003 |
| WO | WO 2004/029050 A1 | 4/2004 |
| WO | WO 2004/058258 | 7/2004 |
| WO | WO 2004/110350 | 12/2004 |
| WO | WO 2005/000798 A1 | 1/2005 |
| WO | WO 2005/082856 A2 | 9/2005 |
| WO | WO 2006/032631 A1 | 3/2006 |
| WO | WO 2006/039327 A2 | 4/2006 |
| WO | WO 2006/065204 A1 | 6/2006 |
| WO | WO 2007/068411 A2 | 6/2007 |
| WO | WO 2007/098967 A2 | 9/2007 |
| WO | WO 2008/011348 A2 | 1/2008 |
| WO | WO 2008/061795 A2 | 5/2008 |

OTHER PUBLICATIONS

Tsolaki et al., "Alzheimer's disease, etc.," Clinical Ophthalmology 2011: 5 887-890.*
Wang et al., "Cholesterol enhances, etc.," Biochemical and Biophysical Research Communications 424 (2012) 704-709.*
Ghiso et al., "Alzheimer's Disease, etc.," J Glaucoma 22(5) Suppl 1, 2013, S36-S38.*
McKinnon, "Glaucoma, etc.," Frontiers in Bioscience 8, s1140-1156, 2003.*
Moore et al., "A Review of, etc.," Survey of Ophthalmology, 58(3), 2013, 278-285.*
Bruban et al., "Amyloid-, etc.," Aging Cell (2009) 8, pp. 162-177.*
Guo et al., "Targeting amyloid, etc.," PNAS, 104(33) 2007, 13444-13449.*
Surguchev et al., "Conformational, etc.," Brain Research Bulletin 81 (2010) 12-24.*
Russian Decision on Grant for Russian Patent Application No. 2012119757 dated Sep. 15, 2014, pp. 1-7.

(Continued)

*Primary Examiner* — Patricia L Morris
(74) *Attorney, Agent, or Firm* — F. Brent Nix, Esq.; Johnson, Marcou & Isaacs, LLC

(57) ABSTRACT

The present invention relates to 2,6-diaminopyridine compounds that can be employed in the treatment of a group of disorders and abnormalities associated with amyloid protein and of diseases or conditions associated with amyloid-like proteins. The compounds of the present invention can also be used in the treatment of ocular diseases associated with pathological abnormalities/changes in the tissues of the visual system.

8 Claims, 1 Drawing Sheet

(56) References Cited

OTHER PUBLICATIONS

Anderson, et al., "Characterization of β Amyloid Assemblies in Drusen: the Deposits Associated with Aging and Age-Related Macular Degeneration", Experimental Eye Research, vol. 78, 2004, 243-256.
Dentchev, et al., "Amyloid-β is Found in Drusen from Some Age-Related Macular Degeneration Retinas, but not in Drusen from Normal Retinas", Molecular Vision, May 14, 2003, 2003.
Ding, et al., "Targeting Age-Related Macular Degeneration with Alzheimer's Disease Based Immunotherapies: Anti-Amyloid β Antibody Attenuates Pathologies in an Age-Related Macular Degeneration Mouse Model", Vision Research, vol. 48, 2008, 339-345.
Herold, et al., "Neurodegeneration in Autoimmune Optic Neuritis is Associated with Altered APP Cleavage in Neurons and Up-Regulation of p53", PLOS ONE, Oct. 1, 2015, 17.
Ito, et al., "Induction of Amyloid-β1-42 in the Retina and Optic Nerve Head of Chronic Ocular Hypertensive Monkeys", Molecular Vision, vol. 18, Oct. 29, 2012, 2647-2657.
Levin, et al., "History of Neuroprotection and Rationale as a Therapy for Glaucoma", The American Journal of Managed Care, vol. 14, No. 1, Feb. 2008, S11-S14.
London, et al., "The Retina as a Window to the Brain—from Eye Research to CNS Disorders", Nature, vol. 9, Jan. 2013, 44-53.
Ning et al., "Amyloid-β Deposits Lead to Retinal Degeneration in a Mouse Model of Alzheimer Disease", Invest Ophthalmol Vis Sci., vol. 49, No. 11, Nov. 2008, 5136-5143.
Reichard, et al., "β-Amyloid Precursor Protein Immunohistochemistry in the Evaluation of Pediatric Traumatic Optic Nerve Injury", American Academy of Ophthalmology, 2004, 822-827.
Chinese Office Action for Counterpart Chinese Application No. 201410407476.7, Apr. 25, 2016, 6 pages. (English Translation provided).
Cheung et al. "Neuroprotection in Glaucoma: Drug-based Approaches," Optom Vis Sci 85(6): 406-416 (2008).
Goldblum et al. "Distribution of Amyloid Precursor Protein and Amyloid-β Immunoreactivity in DBA/2J Glaucomatous Mouse Retinas" Investigative Ophthamology: Visual Science, 48(11): 5085-5090 (2007).
Ito et al. "Induction of Amyloid β1-42 in the Retina and Optic Nerve Head of Chronic Occular Hypertensive Monkeys" Molecular Vision, 1812647-57 (2012).
Janciauskiene et al. "Alzheimer's Peptide and Serine Protease Inhibitors in Glaucoma and Exfoliation Syndrome," Documenta Ophthamologica. 106: 215-23 (2003).
Morrison et al. "Rat models for glaucoma research" Prog Brain Res. 173: 285-301.
Office Action dated Oct. 26, 2011 for U.S. Appl. No. 12/516,151, pp. 1-18.
Office Action dated Jun. 22, 2011 for U.S. Appl. No. 12/516,151, pp. 1-18.
Final Office Action dated May 2, 2013 for U.S. Appl. No. 12/905,356, pp. 1-10.
English-language translation of Office Action dated Nov. 23, 2011 for Russian Patent Application No. 2009123647, pp. 1-8.
English-language translation of Office Action dated Feb. 28, 2011 for Chinese Patent Application No. 2007800496221, pp. 1-9.
English-language translation of Office Action dated Feb. 4, 2013 for Japanese Patent Application No. 2009-537556, pp. 1-11.
English-language translation of Office Action dated Apr. 30, 2013 in counterpart Mexican patent application No. MX/a/2012/004388, pp. 1-2.
Citron, "Alzheimer's Disease: Strategies for Disease Modification," Nature Rev. Drug Discov., vol. 9, 2010, pp. 387-398.
Citron, "Alzheimer's Disease: Treatments in Discovery and Development," Nature Neurosci. (Suppl.) 5, 2002, pp. 1055-1057.
Dorgan et al., "N-Alkyl and N-Acyl Derivatives of 3(5)-Aminopyrazole," Journal of Chemical Research, vol. 6, 1979, p. 198.
Dorwald, Side Reactions in Organic Synthesis, 2005, VCH Weinheim Preface, pp. 1-15 & Chapter 8, pp. 279-308.
Gever, "Beta-Amyloid Inhibitor Fails in Alzheimer's Trial," retrieved from www.MedPageToday.com, Dec. 15, 2009.
Graubaum, "Acylwanderungen am 3(5)-Amino-Pyrazol," J. Prakt. Chem, vol. 335, 1993, pp. 585-588.
Grohol, "Alzheimer's Drug Fails Clinical Trials," retrieved from psychocentral.com, Aug. 18, 2010.
Hergenrother, "Poly-1,2,4-Triazoles and Poly-1,3,4-Oxadiazoles from Precursor Poly-N-Acylhydrazines," Macromolecules, vol. 3, No. 1, Jan.-Feb. 1970, pp. 10-15.
Hill, "Flurizan Hopes Flattened by Failure in Latest Clinical Trial," retrieved from About.com, Jun. 30, 2008.
Huc, I. et al., "Hydroxy-Substituted Oligopyridine Dicarboxamide Helical Foldamers," Chem. Commun., 2002, pp. 578-579.
Moustafa, "Synthesis and Some Reactions of Quinoxalinecarboazides," J. Chin. Chem. Soc., vol. 47, No. 2, 2000, pp. 351-357.
Pahnke, "Alzheimer's Disease and Blood-Brain Barrier Function: Why Have Anti-β-Amyloid Therapies Failed to Prevent Dementia Progression?" Neurosci. Biobehav. Rev., vol. 33, 2009, pp. 1099-1108.
Pajouhesh et al., J. Am. Soc. Exp. Neurother., 2005, vol. 2, p. 541.
Pfeiffer et al., "Effect of Butyllithium on 6H-1,3,4-Thiadiazines," vol. 22, No. 4, 1982, pp. 137-138.
Pfeiffer et al., "The Ring Contraction of 6H-1,3,4-Thiadiazines to Pyrazoles under the Effects of Triphenylphosphine and Triethylphosphite," vol. 7, Feb. 17, 1977, pp. 485-487.
Rzepecki et al., "Prevention of Alzheimer's Disease-Associated AB Aggregation by Rationally Designated Nonpeptidic B-Sheet Ligands," The Journal of Biological Chemistry, vol. 279, No. 46, Nov. 12, 2004, pp. 47497-47505.
Rzepecki, P. et al., "Aminopyrazole Oligomers for β-Sheet Stabilization of Peptides," Synthesis 2003, No. 12, pp. 1815-1826.
Stoicescu-Crivat et al., "Poly-1,3,4-Oxadiazoles III, Polycondensation of 5-Aminotetrazole with Diacid Chlorides," Inst. Macromol. Chem. May 25, 2009.
Uversky, "Mysterious Oligomerization of the Amyloidogenic Proteins," Febs J., vol. 277, 2010, pp. 2940-2953.
Database Beilstein Beilstein Institute for Organic Chemistry, Frankfurt-Main, DE; 1988, Database accession No. BRN: 4961227.
Database Beilstein Beilstein Institute for Organic Chemistry, Frankfurt-Main, DE; 1985, Database accession No. BRN: 5954121.
Database Beilstein Beilstein Institute for Organic Chemistry, Frankfurt-Main, DE; 1982, Database accession No. BRN: 5739402.
Database Beilstein Beilstein Institute for Organic Chemistry, Frankfurt-Main, DE; 1979, Database accession No. BRN: 779646.
Database Beilstein Beilstein Institute for Organic Chemistry, Frankfurt-Main, DE; 1979, Database accession No. BRN: 1099195.
Database Beilstein Beilstein Institute for Organic Chemistry, Frankfurt-Main, DE; 1970, Database accession No. BRN: 744195.

* cited by examiner

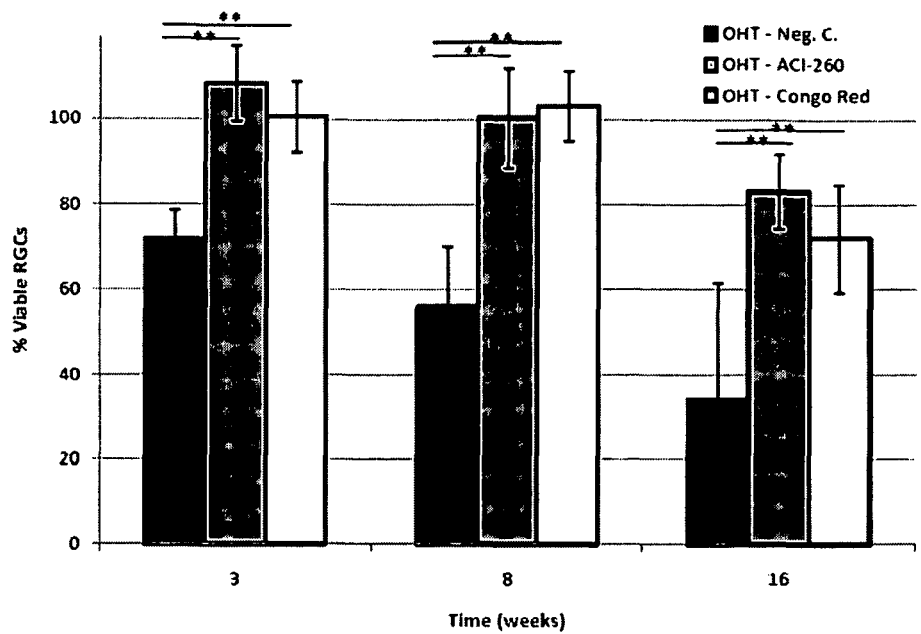

SEQUENCE LISTING

<160> NUMBER OF SEQ ID NOS: 4

<210> SEQ ID NO 1
<211> LENGTH: 112
<212> TYPE: PRT
<213> ORGANISM: Artificial Sequence
<220> FEATURE:
<223> OTHER INFORMATION: Artificial Humanized C2 HuVK 1 Variable light
      chain

<400> SEQUENCE: 1

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Tyr Ser
            20                  25                  30

Asn Gly Asp Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110

<210> SEQ ID NO 2
<211> LENGTH: 219
<212> TYPE: PRT
<213> ORGANISM: Artificial Sequence
<220> FEATURE:
<223> OTHER INFORMATION: Artificial Humanized C2 Variable light chain

<400> SEQUENCE: 2

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Tyr Ser
            20                  25                  30

Asn Gly Asp Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

```
Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215

<210> SEQ ID NO 3
<211> LENGTH: 112
<212> TYPE: PRT
<213> ORGANISM: Artificial Sequence
<220> FEATURE:
<223> OTHER INFORMATION: Artificial Humanized C2 HuVH AF 4 Variable
      heavy chain

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Leu Val
        35                  40                  45

Ala Ser Ile Asn Ser Asn Gly Gly Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Gly Asp Tyr Trp Gly Gln Gly Thr Thr Val Thr Val Ser Ser
            100                 105                 110

<210> SEQ ID NO 4
<211> LENGTH: 439
<212> TYPE: PRT
<213> ORGANISM: Artificial Sequence
<220> FEATURE:
<223> OTHER INFORMATION: Artificial Humanized C2 heavy chain

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Leu Val
        35                  40                  45

Ala Ser Ile Asn Ser Asn Gly Gly Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Gly Asp Tyr Trp Gly Gln Gly Thr Thr Val Thr Val Ser Ser
            100                 105                 110

Ala Ser Thr Lys Gly Pro Ser Val Phe Pro Leu Ala Pro Cys Ser Arg
            115                 120                 125

Ser Thr Ser Glu Ser Thr Ala Ala Leu Gly Cys Leu Val Lys Asp Tyr
        130                 135                 140

Phe Pro Glu Pro Val Thr Val Ser Trp Asn Ser Gly Ala Leu Thr Ser
145                 150                 155                 160
```

```
Gly Val His Thr Phe Pro Ala Val Leu Gln Ser Ser Gly Leu Tyr Ser
            165                 170                 175
Leu Ser Ser Val Val Thr Val Pro Ser Ser Ser Leu Gly Thr Lys Thr
            180                 185                 190
Tyr Thr Cys Asn Val Asp His Lys Pro Ser Asn Thr Lys Val Asp Lys
            195                 200                 205
Arg Val Glu Ser Lys Tyr Gly Pro Pro Cys Pro Pro Cys Pro Ala Pro
    210                 215                 220
Glu Phe Leu Gly Gly Pro Ser Val Phe Leu Phe Pro Pro Lys Pro Lys
225                 230                 235                 240
Asp Thr Leu Met Ile Ser Arg Thr Pro Glu Val Thr Cys Val Val Val
            245                 250                 255
Asp Val Ser Gln Glu Asp Pro Glu Val Gln Phe Asn Trp Tyr Val Asp
            260                 265                 270
Gly Val Glu Val His Asn Ala Lys Thr Lys Pro Arg Glu Glu Gln Phe
            275                 280                 285
Asn Ser Thr Tyr Arg Val Val Ser Val Leu Thr Val Leu His Gln Asp
    290                 295                 300
Trp Leu Asn Gly Lys Glu Tyr Lys Cys Lys Val Ser Asn Lys Gly Leu
305                 310                 315                 320
Pro Ser Ser Ile Glu Lys Thr Ile Ser Lys Ala Lys Gly Gln Pro Arg
            325                 330                 335
Glu Pro Gln Val Tyr Thr Leu Pro Pro Ser Gln Glu Glu Met Thr Lys
            340                 345                 350
Asn Gln Val Ser Leu Thr Cys Leu Val Lys Gly Phe Tyr Pro Ser Asp
            355                 360                 365
Ile Ala Val Glu Trp Glu Ser Asn Gly Gln Pro Glu Asn Asn Tyr Lys
    370                 375                 380
Thr Thr Pro Pro Val Leu Asp Ser Asp Gly Ser Phe Phe Leu Tyr Ser
385                 390                 395                 400
Arg Leu Thr Val Asp Lys Ser Arg Trp Gln Glu Gly Asn Val Phe Ser
            405                 410                 415
Cys Ser Val Met His Glu Ala Leu His Asn His Tyr Thr Gln Lys Ser
            420                 425                 430
Leu Ser Leu Ser Leu Gly Lys
            435
```

2,6-DIAMINOPYRIDINE COMPOUNDS SUITABLE FOR TREATING DISEASES ASSOCIATED WITH AMYLOID OR AMYLOID-LIKE PROTEINS OR FOR TREATING OR PREVENTING OCULAR DISEASES OR CONDITIONS ASSOCIATED WITH A PATHOLOGICAL ABNORMALITY/CHANGE IN THE TISSUE OF THE VISUAL SYSTEM

CROSS REFERENCE TO RELATED APPLICATIONS

This application is a divisional of U.S. patent application Ser. No. 12/905,356, filed Oct. 15, 2010, which claims priority to EP 09 17 3184.4 filed Oct. 15, 2009, the disclosures of which are hereby incorporated by reference in their entirety.

FIELD OF THE INVENTION

The present invention relates to novel compounds that can be employed in the treatment of a group of disorders and abnormalities associated with amyloid protein, particularly ocular disorders such as glaucoma or Aged-related Macular Degeneration (AMD), and also treatment of diseases or conditions associated with amyloid-like proteins. The present invention further relates to pharmaceutical compositions comprising these compounds and to the use of these compounds for the preparation of medicaments for the treatment of diseases or conditions associated with amyloid or amyloid-like proteins. A method of treating diseases or conditions associated with amyloid or amyloid-like proteins is also disclosed.

The compounds of the present invention can also be used in the treatment or prevention of ocular diseases associated with pathological abnormalities/changes in the tissues of the visual system, particularly associated with amyloid-beta-related pathological abnormalities/changes in the tissues of the visual system, such as neuronal degradation. Said pathological abnormalities may occur, for example, in different tissues of the eye, such as the visual cortex leading to cortical visual deficits; the anterior chamber and the optic nerve leading to glaucoma; the lens leading to cataract due to beta-amyloid deposition; the vitreous leading to ocular amyloidoses; the retina leading to primary retinal degeneration and macular degeneration, for example age-related macular degeneration; the optic nerve leading to optic nerve drusen, optic neuropathy and optic neuritis; and the cornea leading to lattice dystrophy.

BACKGROUND OF THE INVENTION

Many diseases of aging are based on or associated with amyloid or amyloid-like proteins and are characterized, in part, by the buildup of extracellular deposits of amyloid or amyloid-like material that contribute to the pathogenesis, as well as the progression of the disease.

Those neurodegenerative diseases include both central nervous system disorders and peripheral nervous system disorders, particularly ocular disorders.

Such disorders include, but are not limited to, neurological disorders such as Alzheimer's Disease (AD), diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex. Other disorders which are based on or associated with amyloid-like proteins are progressive supranuclear palsy, multiple sclerosis; Creutzfeld Jacob disease, Parkinson's disease, HIV-related dementia, ALS (amyotropic lateral sclerosis), inclusion-body myositis (IBM), Adult Onset Diabetes; senile cardiac amyloidosis; endocrine tumors, and other diseases, including amyloid-associated ocular diseases that target different tissues of the eye, such as the visual cortex, including cortical visual deficits; the anterior chamber and the optic nerve, including glaucoma; the lens, including cataract due to beta-amyloid deposition; the vitreous, including ocular amyloidoses; the retina, including primary retinal degenerations and macular degeneration, in particular age-related macular degeneration; the optic nerve, including optic nerve drusen, optic neuropathy and optic neuritis; and the cornea, including lattice dystrophy.

Beta-amyloid (A$\beta$) is the major constituent of senile plaques in Alzheimer's disease (AD). Those plaques are caused by the abnormal processing of the amyloid precursor protein (APP) and have been involved in AD neuropathy. A$\beta$ has also recently been implicated in the development of ocular disorders, such as glaucoma, via retinal ganglion cells (RGC) apoptosis. The link between glaucoma and AD was demonstrated in several studies with AD patients also showing RGC loss associated with typical glaucomatous changes, such as optic neuropathy and visual function impairment.

Glaucoma is a group of diseases of the optic nerve involving loss of retinal ganglion cells (RGCs) in a characteristic pattern of optic neuropathy. Glaucoma is often, but not always, accompanied by an increased eye pressure, which may be a result of blockage of the circulation of aqueous fluid, or its drainage.

Although raised intraocular pressure is a significant risk factor for developing glaucoma, no threshold of intraocular pressure can be defined which would be determinative for causing glaucoma.

The damage may also be caused by poor blood supply to the vital optic nerve fibers, a weakness in the structure of the nerve, and/or a problem in the health of the nerve fibers themselves.

Untreated glaucoma leads to permanent damage of the optic nerve and resultant visual field loss, which can progress to blindness.

RGCs are the nerve cells that transmit visual signals from the eye to the brain. Caspase-3 and caspase-8, two major enzymes in the apoptotic process, are activated in the process leading to apoptosis of RGCs. Caspase-3 cleaves amyloid precursor protein (APP) to produce neurotoxic fragments, including amyloid $\beta$. Without the protective effect of APP, amyloid $\beta$ accumulation in the retinal ganglion cell layer results in the death of RGCs and irreversible loss of vision.

The different types of glaucomas are classified as open-angle glaucomas, if the condition is chronic, or closed-angle glaucomas, if acute glaucoma occurs suddenly. Glaucoma usually affects both eyes, but the disease can progress more rapidly in one eye than in the other. Chronic open-angle glaucoma (COAG), also known as primary open angle glaucoma (POAG), is the most common type of glaucoma. COAG is caused by microscopic blockage in the trabecular meshwork, which decreases the drainage of the aqueous outflow into the Schlemm's canal and raises the intraocular pressure (IOP). POAG usually affects both eyes and is strongly associated with age and a positive family history. Its frequency increases in elderly people as the eye drainage mechanism may gradually become clogged with aging. The increase in intraocular pressure in subjects affected by chronic open-angle glaucoma is not accompanied by any symptoms until the loss is felt on the central visual area.

Acute Angle Closure Glaucoma (AACG) or closed-angle glaucoma is a relatively rare type of glaucoma characterized by a sudden increase in intraocular pressure to 35 to 80 mmHg, leading to severe pain and irreversible loss of vision. The sudden pressure increase is caused by the closing of the filtering angle and blockage of the drainage channels. Individuals with narrow angles have an increased risk for a sudden closure of the angle. AACG usually occurs monocularly, but the risk exists in both eyes. Age, cataract and pseudoexfoliation are also risk factors since they are associated with enlargement of the lens and crowding or narrowing of the angle. A sudden glaucoma attack may be associated with severe eye pain and headache, inflamed eye, nausea, vomiting, and blurry vision.

Mixed or Combined Mechanism Glaucoma is a mixture or combination of open and closed angle glaucoma. It affects patients with acute ACG whose angle opens after laser iridotomy, but who continue to require medications for IOP control, as well as patients with POAG or pseudoexfoliative glaucoma who gradually develop narrowing of the angle.

Normal tension glaucoma (NTG), also known as low tension glaucoma (LTG), is characterized by progressive optic nerve damage and loss of peripheral vision similar to that seen in other types of glaucoma; however, the intraocular pressure is the normal range or even below normal.

Congenital (infantile) glaucoma is a relatively rare, inherited type of open-angle glaucoma. Insufficient development of the drainage area results in increased pressure in the eye that can lead to the loss of vision from optic nerve damage and to an enlarged eye. Early diagnosis and treatment are critical to preserve vision in infants and children affected by the disease.

Secondary glaucoma may result from an ocular injury, inflammation in the iris of the eye (iritis), diabetes, cataract, or use of steroids in steroid-susceptible individuals. Secondary glaucoma may also be associated with retinal detachment or retinal vein occlusion or blockage.

Pigmentary glaucoma is characterized by the detachment of granules of pigment from the iris. The granules cause blockage of the drainage system of the eye, leading to elevated intraocular pressure and damage to the optic nerve.

Exfoliative glaucoma (pseudoexfoliation) is characterized by deposits of flaky material on the anterior capsule and in the angle of the eye. Accumulation of the flaky material blocks the drainage system and raises the eye pressure.

Diagnosis of glaucoma may be made using various tests. Topometry determines the pressure in the eye by measuring the tone or firmness of its surface. Several types of tonometers are available for this test, the most common being the applanation tonometer. Pachymetry determines the thickness of the cornea which, in turn, measures intraocular pressure. Gonioscopy allows examination of the filtering angle and drainage area of the eye. Gonioscopy can also determine if abnormal blood vessels may be blocking the drainage of the aqueous fluid out of the eye. Ophtalmoscopy allows examination of the optic nerve and can detect nerve fiber layer drop or changes in the optic disc, or indentation (cupping) of this structure, which may be caused by increased intraocular pressure or axonal drop out. Gonioscopy is also useful in assessing damage to the nerve from poor blood flow or increased intraocular pressure. Visual field testing maps the field of vision, subjectively, which may detect signs of glaucomatous damage to the optic nerve. This is represented by specific patterns of visual field loss. Ocular coherence tomography, an objective measure of nerve fiber layer loss, is carried out by looking at the thickness of the optic nerve fiber layer (altered in glaucoma) via a differential in light transmission through damaged axonal tissue.

Macular degeneration is a common eye disease that causes deterioration of the macula, which is the central area of the retina (the paper-thin tissue at the back of the eye where light-sensitive cells send visual signals to the brain). Sharp, clear, 'straight ahead' vision is processed by the macula. Damage to the macula results in the development of blind spots and blurred or distorted vision. Age-related macular degeneration (AMD) is a major cause of visual impairment in the United States and for people over age 65 it is the leading cause of legal blindness among Caucasians. Approximately 1.8 million Americans age 40 and older have advanced AMD, and another 7.3 million people with intermediate AMD are at substantial risk for vision loss. The government estimates that by 2020 there will be 2.9 million people with advanced AMD. Victims of AMD are often surprised and frustrated to find out how little is known about the causes and treatment of this blinding condition.

There are two forms of macular degeneration: dry macular degeneration and wet macular degeneration. The dry form, in which the cells of the macula slowly begin to break down, is diagnosed in 85 percent of macular degeneration cases. Both eyes are usually affected by dry AMD, although one eye can lose vision while the other eye remains unaffected. Drusen, which are yellow deposits under the retina, are common early signs of dry AMD. The risk of developing advanced dry AMD or wet AMD increases as the number or size of the drusen increases. It is possible for dry AMD to advance and cause loss of vision without turning into the wet form of the disease; however, it is also possible for early-stage dry AMD to suddenly change into the wet form.

The wet form, although it only accounts for 15 percent of the cases, results in 90 percent of the blindness, and is considered advanced AMD (there is no early or intermediate stage of wet AMD). Wet AMD is always preceded by the dry form of the disease. As the dry form worsens, some people begin to have abnormal blood vessels growing behind the macula. These vessels are very fragile and will leak fluid and blood (hence 'wet' macular degeneration), causing rapid damage to the macula.

The dry form of AMD will initially often cause slightly blurred vision. The center of vision in particular may then become blurred and this region grows larger as the disease progresses. No symptoms may be noticed if only one eye is affected. In wet AMD, straight lines may appear wavy and central vision loss can occur rapidly.

Diagnosis of macular degeneration typically involves a dilated eye exam, visual acuity test, and a viewing of the back of the eye using a procedure called fundoscopy to help diagnose AMD, and—if wet AMD is suspected—fluorescein angiography may also be performed. If dry AMD reaches the advanced stages, there is no current treatment to prevent vision loss. However, a specific high dose formula of antioxidants and zinc may delay or prevent intermediate AMD from progressing to the advanced stage. MACU-GEN® (pegaptanib sodium injection), laser photocoagulation and photodynamic therapy can control the abnormal blood vessel growth and bleeding in the macula, which is helpful for some people who have wet AMD; however, vision that is already lost will not be restored by these techniques. If vision is already lost, low vision aids exist that can help improve the quality of life.

One of the earliest signs of age-related macular degeneration (AMD) is the accumulation of extracellular deposits known as drusen between the basal lamina of the retinal pigmented epithelium (RPE) and Bruch's membrane (BM). Recent studies conducted by Anderson et al. have confirmed that drusen contains amyloid beta. (Experimental Eye Research 78 (2004) 243-256).

Prions cause neurodegenerative diseases such as scrapie in sheep, bovine spongiform encephalopathy in cattle and Creutzfeldt-Jacob disease in humans. The only known component of the particle is the scrapie isoform of the protein, PrPSc. Although prions multiply, there is no evidence that they contain nucleic acid. PrPSc is derived from the non-infectious, cellular protein PrPC by a posttranslational process during which PrPC undergoes a profound conformational change.

The scrapie protein PrPSc has a critical role in neuronal degeneration and during disease development undergoes a three stage transition as follows: PrPC (normal cellular isoform of protein)—PrPSc: infectious form (scrapie isoform of protein)—protein PrP27-30.

Such a cascade of events occurs during the development of Creutzfeldt-Jacob disease (CJD), Kuru, Gerstmann-Straussler-Scheinker Syndrome (GSS), fatal familial insomnia in man, scrapie in sheep and goats, encephalopathy in mink and bovine spongiform encephalopathy in cattle.

The cellular non-toxic protein (PrPC) is a sialoglycoprotein of molecular weight 33000 to 35000 that is expressed predominantly in neurons. In the diseases mentioned above, PrPC is converted into an altered form (PrPSc), which is distinguishable from its normal homologue by its relative resistance to protease digestion. PrPSc accumulates in the central nervous system of affected animals and individuals and its protease-resistant core aggregates extracellularly.

Amyloidosis is not a single disease entity but rather a diverse group of progressive disease processes characterized by extracellular tissue deposits of a waxy, starch-like protein called amyloid, which accumulates in one or more organs or body systems. As the amyloid deposits build up, they begin to interfere with the normal function of the organ or body system. There are at least 15 different types of amyloidosis. The major forms are primary amyloidosis without known antecedent, secondary amyloidosis following some other condition, and hereditary amyloidosis.

Secondary amyloidosis occurs in people who have a chronic infection or inflammatory disease, such as tuberculosis, a bacterial infection called familial Mediterranean fever, bone infections (osteomyelitis), rheumatoid arthritis, inflammation of the small intestine (granulomatous ileitis), Hodgkin's disease, and leprosy.

Optic nerve drusen are globular concretions of protein and calcium salts which are felt to represent secretions through congenitally altered vascular structures affecting the axonal nerve fiber layer. These accumulations occur in the peripapillary nerve fiber layer and are felt to damage the nerve fiber layer either directly by compression or indirectly through disruptions of the vascular supply to the nerve fiber layer. They usually become visible after the first decade of life in affected individuals. They occur most often in both eyes but may also affect one eye, and may cause mild loss of peripheral vision over many years.

Optic neuropathy is a disease characterized by damage to the optic nerve caused by demyelination, blockage of blood supply, nutritional deficiencies, or toxins. Demyelinating optic neuropathies (see optic neuritis below) are typically caused by an underlying demyelinating process such as multiple sclerosis. Blockage of the blood supply, known as ischemic optic neuropathy, can lead to death or dysfunction of optic nerve cells. Non-arteritic ischemic optic neuropathy usually occurs in middle-age people. Risk factors include high blood pressure, diabetes and atherosclerosis. Arteritic ischemic optic neuropathy usually occurs in older people following inflammation of the arteries (arteritis), particularly the temporal artery (temporal arteritis). Loss of vision may be rapid or develop gradually over 2 to 7 days and the damage may be to one or both eyes. In people with optic neuropathy caused by exposure to a toxin or to a nutritional deficiency, both eyes are usually affected.

About 40% of people with non-arteritic ischemic optic neuropathy experience spontaneous improvement over time. Non-arteritic ischemic optic neuropathy is treated by controlling blood pressure, diabetes and cholesterol levels. Arteritic ischemic optic neuropathy is treated with high doses of corticosteroids to prevent loss of vision in the second eye.

Optic neuritis is associated with mild or severe vision loss in one or both eyes and may be caused by a systemic demyelinating process (see above), viral infection, vaccination, meningitis, syphilis, multiple sclerosis and intraocular inflammation (uveitis). Eye movement may be painful and vision may deteriorate with repeat episodes. Diagnosis involves examination of the reactions of the pupils and determining whether the optic disk is swollen. Magnetic resonance imaging (MRI) may show evidence of multiple sclerosis or, rarely, a tumor pressing on the optic nerve, in which case vision improves once the tumor pressure is relieved. Most cases of optic neuritis improve over a few months without treatment. In some cases, treatment with intravenous corticosteroids may be necessary.

A cataract is an opacity that develops in the crystalline lens of the eye or in its envelope. Cataracts typically cause progressive vision loss and may cause blindness if left untreated. In the Morgagnian Cataract, the cataract cortex progressively liquefies to form a milky white fluid and may cause severe inflammation if the lens capsule ruptures and leaks. If left untreated, the cataract may also cause phacomorphic glaucoma. Cataracts may be congenital in nature or caused by genetic factors, advanced age, long-term ultraviolet exposure, exposure to radiation, diabetes, eye injury or physical trauma.

Extra-capsular (ECCE) surgery is the most effective treatment to treat cataract. In the surgery, the lens is removed, but the majority of the lens capsule is left intact. Phacoemulsification, a small incision on the side of the cornea, is typically used to break up the lens before extraction.

Ocular amyloidosis is a hereditary disorder associated with Type I Familial Amyloidotic Polyneuropathy (FAP) and characterized by abnormal conjunctival vessels, keratoconjunctivitis sicca, pupillary abnormalities and, in some cases, vitreous opacities and secondary glaucoma. Type I FAP is associated with mutations in transthyretin (TTR), a tetrameric plasma protein (prealbumin) synthesized in the liver, the retinal pigment epithelium2 and thechoroid plexus of the brain. Different mutations cause transthyretin to polymerize into a pleated structure of amyloid fibril, leading to hereditary amyloidosis. The most frequent mutation is TTR-met303, in which methionine replaces valine at position 30 in transthyretin.

Type IV FAP is associated with lattice corneal dystrophy (LCD). Lattice corneal dystrophy is an inherited, primary, usually bilateral corneal amyloidosis characterized by the presence of refractile lattice lines with a double contour in the corneal stroma. LCD type I (Biber-Haab-Dimmer) is an autosomal dominant, bilaterally symmetrical corneal disorder characterized by the presence of numerous translucent fine lattice lines with white dots and faint haze in the superficial and middle layers of the central stroma. The symptoms start during the first or second decades of life, causing a progressive loss of vision. Most patients require a corneal transplant by 40 years of age. LCD type II is associated with systemic amyloidosis (Meretoja's syndrome) and is characterized by the presence of thick lattice lines in the limbus, central cornea and stroma. Vision is not affected until later in life. LCD type III affect middle-age people and is characterized by the presence of thick lattice lines that extend from limbus to limbus. LCD type III A is characterized by the accumulation of amyloid deposits in the stroma and the presence of ribbons of amyloid between the stroma and Bowman's layer, LCD type III A differs from LCD type III because of the presence of corneal erosions, the occurrence in whites and the autosomal dominant inheritance pattern. There is no cure for glaucoma. Most treatments for glaucoma are designed to lower and/or control intraocular pressure (IOP), which can damage the optic nerve that transmits visual information to the brain. Glaucoma eye drops often are the first choice over glaucoma surgery and can be very effective at controlling IOP to prevent eye damage. Medications for the treatment of glaucoma are classified by their active chemical compounds and can be listed in the following categories, with current approved drugs approved shown in brackets):

Beta blockers (TIMOPTIC®, BETOPTIC®, ISTALOL®, TIMOLOL™) work by decreasing fluid (aqueous) production in the eye.

Carbonic anhydrase inhibitors (TRUSOPT®, AZOPT®, DIAMOX®, NAPTAZANE™, DARANIDE®) decrease the rate of aqueous humor production.

Alpha-adrenergic agonists (ALPHAGAN®, ALPHAGAN-P®, IOPIDINE®) also decrease the rate of aqueous humor production.

Prostaglandins (XALATAN®, LUMIGAN®, TRAVATAN Z®, RESCULA®) redirect drainage of the aqueous humor through a different pathway at the back of the eye, thus reducing buildup of eye pressure.

Parasympathomimetics (Carbachol, Pilocarpine) work by increasing the outflow of aqueous fluid from the eye, thus increasing drainage of intraocular fluids.

Epinephrine decreases the rate of aqueous humor production and increases the outflow of aqueous fluid from the eye.

Beside medications aimed at controlling IOP, certain investigational glaucoma treatment focus at protecting the optic nerve. The Alzheimer's disease drug memantine is currently being investigated for the glaucoma indication as a neuroprotectant. However randomized clinical study of the N-methyl-d-aspartate (NMDA) antagonist memantine in open-angle glaucoma did not show significant efficacy.

Further glaucoma treatments are laser surgeries, which include trabeculoplasty, a procedure that helps the aqueous humor leave the eye more efficiently. According to the Glaucoma Foundation, nearly 80% of patients respond well enough to the procedure to delay or avoid further surgery. However, pressure increases again in the eyes of half of all patients within two years after laser surgery, according to the National Eye Institute. Incisional surgery is performed if medication and initial laser treatments are unsuccessful in reducing pressure within the eye. One type of surgery, a trabeculectomy, creates an opening in the wall of the eye so that aqueous humor can drain. However, about one-third of trabeculectomy patients develop cataracts within five years, according to the Glaucoma Foundation. If the trabeculectomy fails, additional incisional procedures include placing a drainage tube into the eye between the cornea and iris and the use of a laser or freezing treatment to destroy tissue in the eye that makes aqueous humor. Surgery may save the remaining vision in the patient, but it does not improve sight. Vision may actually be worse following surgery.

Current therapies for the treatment of glaucoma strive to slow the progression of the visual field loss by lowering and controlling intraocular pressure. As mentioned above, this is done either with IOP lowering drugs or by laser trabeculoplasty. Long-term studies of the effects of lowering IOP have been shown to be effective in slowing the disease progression in some patients. Unfortunately, there are patients who continue to lose visual field despite having their IOP lowered or do not respond at all to IOP lowering drugs. Therefore, there is a need to develop new treatments targeting a different feature than intraocular pressure. Such a new target is the neuroprotection of RGCs.

Age-related macular degeneration (AMD) is a major cause of blindness among Caucasians over age 65. Although much progress has been made recently in macular degeneration research, there are no treatments that rescue neuronal cell death that occurs during the course of the disease. There are also no definitive treatments for other ocular diseases associated with amyloid beta-related neuronal degradation, such as cortical visual deficits, optic nerve drusen, optic neuropathy, optic neuritis, ocular amyloidosis and lattice dystrophy.

Amyloid deposits typically contain three components. Amyloid protein fibrils, which account for about 90% of the amyloid material, comprise one of several different types of proteins. These proteins are capable of folding into so-called "beta-pleated" sheet fibrils, a unique protein configuration which exhibits binding sites for Congo red resulting in the unique staining properties of the amyloid protein. In addition, amyloid deposits are closely associated with the amyloid P (pentagonal) component (AP), a glycoprotein related to normal serum amyloid P (SAP), and with sulphated glycosaminoglycans (GAG), complex carbohydrates of connective tissue.

One development towards the treatment of disorders and abnormalities associated with amyloid protein or conditions associated with amyloid-like proteins, such as Alzheimer's disease and prion diseases has been the design of molecules that bind the abnormal β-sheet conformation of Aβ and PrP, respectively, thereby preventing aggregation of these molecules. The β-sheet conformation of peptides is characterized in that hydrogen bonds are formed in a regular pattern between neighboring amino acid strands. This arrangement leads to a stable three dimensional structure. H-bond acceptors (C=O group) and H-bond donors (NH group) alternate in naturally occurring β-sheet peptides with the atoms to be bonded being roughly in one line. Within each amino acid strand, the distances between neighboring H-bond donors and H-bond acceptors fall within specific ranges. In particular, the distance between the H-bond donor (NH group) and the H-bond acceptor (C=O group) within one amino acid residue is from 3.5 to 4.0 Å. The distance between the H-bond acceptor (C=O group) of one amino acid residue and the H-bond donor (NH group) of the following amino acid residue participating in the inter-strand bonding is from 2.6 to 2.9 Å. In other words, the distances between neighboring H-bond donors and H-bond acceptors within one amino acid strand alternate between the following ranges:

H-bond donor (amino acid 1)–H-bond acceptor (amino acid 1)=3.5 to 4.0 Å;

H-bond acceptor (amino acid 1)–H-bond donor 2 (amino acid 2)=2.6 to 2.9 Å.

Ligands that are designed to bind β-sheets ideally have an order of H-bond donors and H-bond acceptors that is complementary to the order of H-bond donors and H-bond acceptors in the amino acid strands of the β-sheet.

In WO 03/095429 and Rzepecki et al., Synthesis (2003) 12, 1815-1826 synthetic molecules are described which are said to bind the β-conformation of Aβ or PrP, thereby preventing their aggregation. To this end, certain molecules were synthesized containing two or more amino pyrazole moieties linked by carbonyl group-containing linkers, e.g. "AmpOx" and "Trimer".

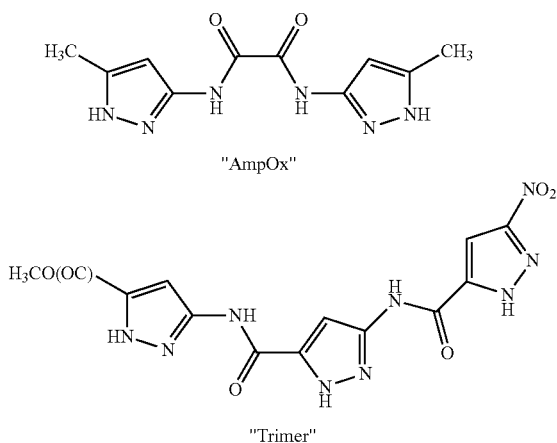

Some of the molecules described in WO 03/095429 are said to have an inhibiting effect on the formation of aggregates of Aβ in two biophysical assays. According to Rzepecki et al., Synthesis (2003) 12, 1815-1826 one of the molecules described therein was able to reduce the aggregation of a recombinant $PrP^C$ in solution. Physicochemical properties, however, were not investigated in these studies.

WO 2008/061795 describes certain heterocyclic compounds which are suitable for treating diseases associated with amyloid or amyloid-like proteins.

Physicochemical properties play a key role in the penetration of the blood-brain barrier by neurotherapeutics. Factors relevant to the success of CNS drugs have been reviewed (H. Pajouhesh and G. R. Lenz, NeuroRx®: J. Am. Soc. Exp. Neurother. (2005) Vol. 2, 541). These include the partition coefficient between water and n-octanol (LogP), i.e. basically the lipophilicity of the compound. Some of the compounds described in WO 03/095429 and Rzepecki et al., Synthesis (2003) 12, 1815-1826 have an unfavorable calculated LogP and are, therefore, not expected to pass the blood-brain barrier. In particular, "AmpOx" has a calculated LogP below zero.

Other compounds described in the above documents have properties that make them unsuitable for administration to a patient due to their deleterious side-effects. For example, "Trimer" is mutagenic, carcinogenic and metabolically unstable.

As discussed above, numerous ocular disorders exist that require improved treatment. In some conditions, there are few treatment options. The treatments that are currently available are not adequate as they are not always effective and may in some instances create secondary complications. What is needed therefore, are an improved and effective therapeutics that provide additional treatment options with improved efficacy and fewer side effects.

SUMMARY OF THE INVENTION

It was an object of the present invention to provide compounds that can be employed in the treatment of diseases or conditions associated with amyloid or amyloid-like proteins, including amyloidosis, but particularly ocular diseases, such as glaucoma. The compounds should be able to pass the blood-brain barrier. Furthermore, they should be pharmaceutically acceptable, in particular, they should not have mutagenic or carcinogenic properties or be metabolically unstable. The compounds should have reasonably high water solubility, while maintaining their biological activity.

A further object of the invention is to provide improved treatment options for subjects affected by ocular diseases associated with pathological abnormalities/changes in the tissues of the visual system, particularly associated with amyloid-beta-related pathological abnormalities/changes in the tissues of the visual system, such as, for example, neuronal degradation. Said pathological abnormalities may occur, for example, in different tissues of the eye, such as the visual cortex leading to cortical visual deficits; the anterior chamber and the optic nerve leading to glaucoma; the lens leading to cataract due to beta-amyloid deposition; the vitreous leading to ocular amyloidoses; the retina leading to primary retinal degeneration and macular degeneration, for example age-related macular degeneration; the optic nerve leading to optic nerve drusen, optic neuropathy and optic neuritis; and the cornea leading to lattice dystrophy.

The present inventors have surprisingly found that these objects can be achieved by the compounds of the general formula (I) as described hereinafter. Accordingly, the present invention relates to a compound of general formula (I).

In a further aspect, the present invention relates to a pharmaceutical composition comprising a compound of general formula (I).

Yet another aspect of the present invention relates to the use of a compound of general formula (I) for the preparation of a medicament for the treatment of diseases or conditions associated with amyloid or amyloid-like proteins, including amyloidosis.

Also disclosed herein is a method of treating diseases or conditions associated with amyloid or amyloid-like proteins, comprising administering to a subject in need of such treatment an effective amount of a compound of general formula (I).

In a preferred embodiment, the disease or condition is an ocular disease or condition. More preferably the disease is glaucoma, even more preferably the disease is selected from the group consisting of chronic (idiopathic) open-angle glaucoma, pupillary block glaucoma, developmental glaucoma, glaucoma associated with other ocular disorders, glaucoma associated with elevated episcleral venous pressure, glaucoma associated with inflammation and trauma, glaucoma following intraocular surgery, high-pressure glaucoma, normal-pressure glaucoma, acute angle-closure glaucoma, subacute angle-closure glaucoma, chronic angle-closure glaucoma, combined mechanism glaucoma, congenital (infantile) glaucoma, juvenile glaucoma aniridia, glaucoma associated with disorders of the corneal endothelium, glaucoma associated with disorders of the iris and ciliary body, glaucoma associated with disorders of the lens, glaucoma associated with disorders of the retina, choroid, and vitreous, glaucoma associated with retinal detachment and vitreoretinal abnormalities, neovascular glaucoma, pigmentary glaucoma, exfoliation syndrome, lens-induced open-angle glaucoma, glaucoma associated with lens intumescence and dislocation, glaucoma associated with keratitis, episcleritis, and scleritis, ciliary block (malignant) glaucoma, glaucoma in aphakia and pseudophakia, epithelial, fibrous, and endothelial proliferation, glaucoma associated with corneal surgery, and glaucoma associated with vitreoretinal surgery.

Yet another aspect of the present invention relates to the use of a compound of general formula (I) for the preparation of a medicament for treating or alleviating the effects of ocular diseases associated with pathological abnormalities/changes in the tissues of the visual system.

Also disclosed herein is a method of treating or alleviating the effects of ocular diseases associated with pathological abnormalities/changes in the tissues of the visual system comprising administering to a subject in need of such treatment an effective amount of a compound of general formula (I).

The ocular diseases associated with pathological abnormalities/changes in the tissues of the visual system are particularly associated with amyloid-beta-related pathological abnormalities/changes in the tissues of the visual system, such as, for example, neuronal degradation. Said pathological abnormalities may occur, for example, in different tissues of the eye, such as the visual cortex leading to cortical visual deficits; the anterior chamber and the optic nerve leading to glaucoma; the lens leading to cataract due to beta-amyloid deposition; the vitreous leading to ocular amyloidoses; the retina leading to primary retinal degeneration and macular degeneration, for example age-related macular degeneration; the optic nerve leading to optic nerve drusen, optic neuropathy and optic neuritis; and the cornea leading to lattice dystrophy.

In one preferred embodiment the ocular disease or condition is selected from the group consisting of glaucoma, neuronal degradation, cortical visual deficits, cataract due to beta-amyloid deposition, ocular amyloidoses, primary retinal degeneration, macular degeneration, for example age-related macular degeneration, optic nerve drusen, optic neuropathy, optic neuritis, and lattice dystrophy.

In a further aspect the invention relates to a mixture (such as a pharmaceutical composition) comprising a compound according to the present invention and optionally at least one further biologically active compound and/or a pharmaceutically acceptable carrier and/or a diluent and/or an excipient. The further biologically active substance can be a known compound used in the medication of diseases and disorders which are caused by or associated with amyloid or amyloid-like proteins.

In one embodiment the further biologically active compound is preferably selected from the group consisting of beta-blockers, carbonic anhydrase inhibitors, alpha- or beta-adrenergic agonists, prostaglandins, parasymphomimetics, cholinesterase inhibitors, acetylcholine synthesis, storage or release enhancers, acetylcholine postsynaptic receptor agonists, N-methyl-D-aspartate glutamate receptor antagonists, compounds used in the treatment of amyloidoses, compounds against oxidative stress, anti-apoptotic compounds, metal chelators, inhibitors of DNA repair such as pirenzepin and metabolites, 3-amino-1-propanesulfonic acid (3APS), 1,3-propanedisulfonate (1,3PDS), α-secretase activators, β- and γ-secretase inhibitors, neurotransmitter, β-sheet breakers, attractants for amyloid beta clearing/depleting cellular components, inhibitors of N-terminal truncated amyloid beta including pyroglutamated amyloid beta 3-42, anti-inflammatory molecules, or cholinesterase inhibitors (ChEIs) such as tacrine, rivastigmine, donepezil, and/or galantamine, M1 agonists, other drugs including any amyloid modifying drug and nutritive supplements, antibodies, vaccines.

In another preferred embodiment the further biologically active compound is selected from the group consisting of timoptic, betoptic, istalol, timolol, trusopt, azopt, diamox, naptazane, daranide, alphagan, alphagan-p, iopidine, xalatan, lumigan, travatan Z, rescula, carbachol, pilocarpine, epinephrine and memantine.

In a further preferred embodiment, the further biologically active compound is an antibody, preferably a monoclonal antibody, including any functionally equivalent antibody or functional parts thereof. Preferably the antibody, more preferably the monoclonal antibody, can include any functionally equivalent antibody or functional parts thereof, is an antibody which binds amyloid β. Preferably the antibody, more preferably the monoclonal antibody, which can include any functionally equivalent antibody or functional parts thereof, is an antibody which antibody, upon co-incubation with amyloid monomeric and/or polymeric soluble amyloid peptides, for example, with β-amyloid monomeric peptides such as Aβ monomeric peptides 1-39; 1-40, 1-41, or 1-42, and/or a polymeric soluble β-amyloid peptide comprising a plurality of the Aβ monomeric units, but especially with an $A\beta_{1-42}$ monomeric and/or an Aβ polymeric soluble amyloid peptide comprising a plurality of the $A\beta_{1-42}$ monomeric units, inhibits the aggregation of the Aβ monomers into high molecular polymeric fibrils or filaments and, in addition, upon co-incubation with pre-formed high molecular polymeric amyloid fibrils or filaments formed by the aggregation of amyloid monomeric peptides, particularly β-amyloid monomeric peptides such as, for example, Aβ monomeric peptides 1-39; 1-40, 1-41, or 1-42, but especially $A\beta_{1-42}$ monomeric peptides, is capable of disaggregating preformed polymeric fibrils or filaments. In one embodiment, the antibody can be a chimeric antibody or a functional part thereof, or a humanized antibody or a functional part thereof. In another embodiment, the antibody can be a monoclonal antibody selected from the group of antibodies having the characteristic properties of an antibody produced by the hybridoma cell line:

a) FP 12H3, deposited on Dec. 1, 2005 and Dec. 9, 2005, respectively as DSM ACC2752;
b) FP 12H3-C2, deposited on Dec. 1, 2005 and Dec. 9, 2005, respectively as DSM ACC2750;
c) FP 12H3-G2, deposited on Dec. 1, 2005 and Dec. 9, 2005, respectively as DSM ACC2751;
d) ET 7E3, deposited on Dec. 8, 2005 as DSM ACC2755; and
e) EJ 7H3, deposited on Dec. 8, 2005 as DSM ACC2756.

In a further embodiment, the antibody can be a humanized antibody exhibiting a light chain and a heavy chain as depicted in SEQ ID NO: 2 and SEQ ID NO: 4 of International Application No. PCT/US2007/073504.

In yet another embodiment the antibody can be a humanized antibody exhibiting a light chain variable region and a heavy chain variable region as depicted in SEQ ID NO: 1 and SEQ ID NO: 3 of International Application NO. PCT/US2007/073504.

In a further embodiment the further biologically active compound can be an Aβ antigenic peptide fragment consisting of a single or repetitive stretch of a plurality of contiguous amino acid residues from the N-terminal part of the Aβ peptide, particularly a stretch of between 13 and 15 contiguous amino acid residues. The Aβ antigenic peptide fragment can be an $A\beta_{1-15}$ peptide antigen such as a palmitoylated $A\beta_{1-15}$ peptide antigen modified by covalently attached palmitoyl residues, particularly between 2 and 4, more particularly 4 residues, at each end of the peptide reconstituted in a liposome.

The further biologically active substance or compound may exert its biological effect by the same or a similar mechanism as the compound according to the invention or by an unrelated mechanism of action or by a multiplicity of related and/or unrelated mechanisms of action.

In all embodiments of the invention the compound of the invention and/or the further biologically active compound are preferably employed in a therapeutically effective amount.

Another aspect of the present invention includes a method for collecting data for the diagnosis of an amyloid-associated disease or condition in a sample or a patient is also disclosed which comprises:
(a) bringing a sample or a specific body part or body area suspected to contain an amyloid protein into contact with a compound according to the present invention;
(b) allowing the compound to bind to the amyloid protein;
(c) detecting the compound bound to the protein; and
(d) optionally correlating the presence or absence of compound binding with the amyloid protein with the presence or absence of amyloid protein in the sample or specific body part or area.

Another embodiment of the present invention is a method of determining the extent of amyloidogenic plaque burden in a tissue and/or a body fluid comprising:
(a) providing a sample representative of the tissue and/or body fluid under investigation;
(b) testing the sample for the presence of amyloid protein with a compound according to the present invention;
(c) determining the amount of compound bound to the amyloid protein; and
(d) calculating the plaque burden in the tissue and/or body fluid.

In a preferred embodiment, the determination in step (c) is conducted such that presence or absence of the compound binding with the amyloid protein correlates with presence or absence of amyloid protein.

A further aspect relates to a method of collecting data for determining a predisposition to an amyloid-associated disease or condition in a patient comprising detecting the specific binding of a compound according to the present invention to an amyloid protein in a sample or in situ which comprises the steps of:
(a) bringing the sample or a specific body part or body area suspected to contain the amyloid protein into contact with a compound according to the present invention, which compound specifically binds to the amyloid protein;
(b) allowing the compound to bind to the amyloid protein to form a compound/protein complex;
(c) detecting the formation of the compound/protein complex;
(d) optionally correlating the presence or absence of the compound/protein complex with the presence or absence of amyloid protein in the sample or specific body part or area; and
(e) optionally comparing the amount of the compound/protein complex to a normal control value.

Yet another aspect of the present invention is a method of collecting data for monitoring minimal residual disease in a patient following treatment with an antibody or a vaccine composition, wherein the method comprises:
(a) bringing a sample or a specific body part or body area suspected to contain an amyloid protein into contact with a compound according to the present invention, which compound specifically binds to the amyloid protein;
(b) allowing the compound to bind to the amyloid protein to form a compound/protein complex;
(c) detecting the formation of the compound/protein complex;
(d) optionally correlating the presence or absence of the compound/protein complex with the presence or absence of amyloid protein in the sample or specific body part or body area; and
(e) optionally comparing the amount of the compound/protein complex to a normal control value.

A method of collecting data for predicting responsiveness of a patient being treated with an antibody or a vaccine composition is also described which comprises:
(a) bringing a sample or a specific body part or body area suspected to contain an amyloid protein into contact with a compound according to the present invention, which compound specifically binds to the amyloid protein;
(b) allowing the compound to bind to the amyloid protein to form a compound/protein complex;
(c) detecting the formation of the compound/protein complex;
(d) optionally correlating the presence or absence of the compound/protein complex with the presence or absence of amyloid protein in the sample or specific body part or body area; and
(e) optionally comparing the amount of the compound/protein complex to a normal control value.

A further aspect of the present invention is a test kit for detection and diagnosis of an amyloid-associated disease or condition comprising a compound according to the present invention. Preferably the test kit comprises a container holding one or more compounds according to the present invention and instructions for using the compound for the purpose of binding to an amyloid protein to form a compound/protein complex and detecting the formation of the compound/protein complex such that presence or absence of the compound/protein complex correlates with the presence or absence of the amyloid protein.

BRIEF DESCRIPTION OF DRAWINGS

FIG. 1 provides a graph showing the effect of a compound of the invention in a Rat Model of Chronic Ocular Hypertension/Glaucoma

DEFINITIONS

One of ordinary skill in this art will understand the meanings of terminology used in the specification. Within the meaning of the present application the following definitions generally apply and are detailed as follows:

"Alkyl" refers to a saturated organic moiety consisting of carbon and hydrogen atoms. Examples of suitable alkyl groups have 1 to 6 carbon atoms, preferably 1 to 4 carbon atoms, and include methyl, ethyl, propyl and butyl.

"Alkylene" refers to a divalent alkyl group. The above comments on "alkyl" apply analogously to this embodiment.

"Cycloalkyl" refers to a cyclic organic moiety consisting of carbon and hydrogen atoms. Examples of suitable alkyl groups have 5 to 10 carbon atoms, preferably 5 or 6 carbon atoms, and include cyclopentyl and cyclohexyl.

"Heterocycloalkyl" refers to a cycloalkyl group as defined above in which one of the carbon atoms has been replaced by a heteroatom which is, e.g., selected from N, O or S, or heteroatom (e.g., N, O and/or S)-containing moiety.

Examples of possible heterocycloalkyl groups include pyrrolidine, tetrahydrofuran, piperidine, etc.

"Alkenyl" refers to an organic moiety consisting of carbon and hydrogen atoms which includes at least one double bond. Examples of suitable alkenyl groups have 2 to 6 carbon atoms, preferably 2 to 4 carbon atoms, and include propenyl, and butenyl.

"Alkinyl" refers to an organic moiety consisting of carbon and hydrogen atoms which includes at least one triple bond. Examples of suitable alkinyl groups have 2 to 6 carbon atoms, preferably 2 to 4 carbon atoms, and include propinyl, and butinyl.

"Aryl" refers to an aromatic organic moiety consisting of carbon and hydrogen atoms which preferably has 5 to 10 carbon atoms, more preferably 5 or 6 carbon atoms. An example is a phenyl ring.

"Heteroaryl" refers to an aryl group as defined above in which one of the carbon atoms has been replaced by a heteroatom which is, e.g., selected from N, O or S, or heteroatom (e.g., N, O and/or S)-containing moiety. Examples of possible heteroaryl groups include pyridine, etc.

"Alkoxy" refers to the group —O-alkyl.

"Aminoalkylene" refers to the group-alkylene-$NR^{14}R^{15}$.

If a group is defined as being "optionally substituted" it can have one or more substituents selected from Hal, $C_{1-6}$ alkyl or $C_{1-6}$ alkoxy.

"Hal" refers to F, Cl, Br, and I. Preferred Hal are F and Cl, more preferably F.

Compounds of the present invention having one or more optically active carbons can exist as racemates and racemic mixtures, diastereomeric mixtures and individual diastereomers, enantiomeric mixtures and single enantiomers, tautomers, atropisomers, and rotamers. All isomeric forms are included in the present invention. Compounds described in this invention containing olefinic double bonds include E and Z geometric isomers. Also included in this invention are all salt forms, polymorphs, hydrates and solvates.

The preferred definitions given in the "Definition"-section apply to all of the embodiments described below unless stated otherwise.

DETAILED DESCRIPTION OF THE INVENTION

In a first embodiment the present invention relates to a compound of the general formula (I)

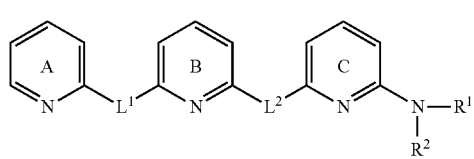

(I)

The pyridine rings A, B and C are independently unsubstituted or substituted by one or more substituents which are independently selected from the group consisting of: $C_{1-6}$-alkylene-C(=$NR^{13}$)—$NHR^{14}$, $C_{1-6}$-alkylene-C(O)—NH—CN, $C_{1-6}$-alkylene-C(O)—$NR^{16}$—$C_{1-6}$-alkylene-$NR^{14}R^{15}$, $C_{1-6}$-alkylene-C(O)—$NR^{14}R^{15}$, $C_{1-6}$-alkylene-C(O)—$OR^{13}$, $C_{1-6}$-alkylene-$NR^{16}$—C(=$NR^{13}$)—$NR^{14}R^{15}$, $C_{1-6}$-alkylene-$NR^{16}$—C(O)—$NR^{14}R^{15}$, $C_{1-6}$-alkylene-$NR^{16}$—C(O)—$OR^{14}$, $C_{1-6}$-alkylene-$NR^{16}$—C(O)—$R^{14}$, $C_{1-6}$-alkylene-$NR^{14}R^{15}$, $C_{1-6}$-alkylene-$NR^{16}$—$SO_2$—$NR^{14}R^{15}$, $C_{1-6}$-alkylene-$NR^{16}$—$SO_2R^{14}$, C(=$NR^{13}$)—$NHR^{14}$, C(O)—NH—CN, C(O)—$NR^{16}$—$C_{1-6}$-alkylene-$NR^{14}R^{15}$, C(O)—$NR^{16}$—$NR^{14}R^{15}$, C(O)—$NR^{14}R^{15}$, C(O)—OH, C(O)—$OR^{13}$, C(O)—$R^{13}$, $CHal_3$, CN, Hal, $NO_2$, $NR^{13}$—C(=$NR^{13}$)—$NR^{14}R^{15}$, $NR^{16}$—C(O)—$NR^{14}R^{15}$, $NR^{16}$—C(O)—$OR^{14}$, $NR^{16}$—C(O)—$R^{14}$, $NR^{14}R^{15}$, $NR^{16}$—$SO_2$—$NR^{14}R^{15}$$NR^{16}$—$SO_2R^{14}$, O—$C_{1-6}$-alkylene-C(O)—$NR^{14}R^{15}$, O—C(O)—$NR^{14}R^{15}$, O—C(O)—$R^{13}$, $OR^{13}$, $S(O)_t$—$C_{1-6}$-alkylene-C(O)—$NR^{14}R^{15}$, $S(O)_t$—C(O)—$OR^{13}$, $S(O)_tR^{13}$, $SO_2$—$NR^{14}R^{15}$, $C_{1-6}$-alkyl, $C_{5-10}$-cycloalkyl, $C_{5-10}$-cycloalkyl-$C_{1-6}$-alkylene, 5- to 10-membered heterocycloalkyl, haloalkyl having 1 to 6 carbon atoms, 6 to 10-membered heterocycloalkyl-$C_{1-6}$-alkylene, $C_{2-6}$-alkenyl, $C_{2-6}$-alkynyl, $C_{5-10}$-aryl, 5- to 10-membered heteroaryl, $C_{5-10}$-aryl-$C_{1-6}$-alkylene, 5- to 10-membered heteroaryl-$C_{1-6}$-alkylene, $C_{1-6}$-alkoxy-$C_{1-6}$-alkylene and aminoalkylene wherein the alkylene group has 1 to 6 carbon atoms, wherein alkyl, cycloalkyl, cycloalkylalkylene, heterocycloalkylene, heterocycloalkylalkylene, alkenyl, alkynyl, aryl, heteroaryl, arylalkylene, heteroarylalkylene, alkoxyalkylene and aminoalkylene may be optionally substituted. In a preferred embodiment the pyridine rings A, B and C are independently unsubstituted or substituted by one or two substituents. In a preferred embodiment the substituents are independently selected from the group consisting of: $C_{1-6}$-alkyl, haloalkyl having 1 to 6 carbon atoms, Hal or $OR^{13}$, more they are independently selected from the group consisting of: $C_{1-6}$-alkyl or OH. Most preferably the pyridine rings A, B and C are unsubstituted.

$L^1$ and $L^2$ are independently selected from moieties having the formula (a) or (b)

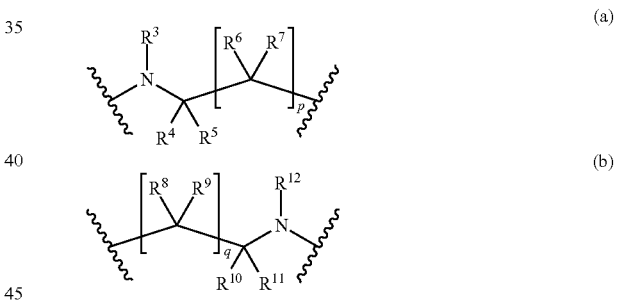

wherein at least one of $L^1$ or $L^2$ has the formula (b). This ensures that the compound having the general formula (I) includes a 2,6-diaminopyridine moiety.

In the formula (a) $R^3$ is selected from the group consisting of C(=$NOR^{13}$)—$R^{14}$, C(=$NR^{13}$)—$NR^{14}R^{15}$, C(O)—C(=$NR^{13}$)—$NR^{14}R^{15}$, C(O)—$NR^{14}R^{15}$, C(O)—$OR^{13}$, $R^{13}$, $S(O)_tNR^{14}R^{15}$, and $S(O)_tR^{13}$. In a preferred embodiment $R^3$ is $R^{13}$. In a more preferred embodiment $R^3$ is selected from the group consisting of hydrogen and $C_{1-6}$-alkyl. In an even more preferred embodiment $R^3$ is hydrogen.

$R^4$, $R^5$, $R^6$, and $R^7$ are independently selected from the group consisting of hydrogen, $C_{1-6}$-alkylene-C(=$NR^{13}$)$NHR^{14}$, $C_{1-6}$-alkylene-C(O)—NH—CN, $C_{1-6}$-alkylene-C(O)—$NR^{16}$—$C_{1-6}$alkylene-$NR^{14}R^{15}$, $C_{1-6}$-alkylene-C(O)—$NR^{16}$—$NR^{14}R^{15}$, $C_{1-6}$-alkylene-C(O)—$NR^{14}R^{15}$, $C_{1-6}$-alkylene-C(O)—$OR^{13}$, $C_{1-6}$-alkylene-$NR^{16}C$(=$NR^{13}$)$NR^{14}R^{15}$, $C_{1-6}$-alkylene-$NR^{16}$—C(O)—$NR^{14}R^{15}$, $C_{1-6}$-alkylene-$NR^{16}$—C(O)$OR^{14}$, $C_{1-6}$-alkylene-$NR^{16}$—C(O) $R^{14}$, $C_{1-6}$-alkylene-$NR^{14}R^{15}$, $C_{1-6}$-alkylene-$NR^{16}$—$SO_2$—$NR^{14}R^{15}$, $C_{1-6}$-alkylene-$NR^{16}$—$SO_2$—$R^{14}$, C(=$NR^{13}$)$NHR^{14}$, C(O)—NH—CN, C(O)—$NR^{16}$—$C_{1-6}$-alkylene- $NR^{14}R^{15}$, $C(O)-NR^{16}-NR^{14}R^{15}$, $C(O)-NR^{14}R^{15}$, $C(O)-OH$, $C(O)-OR^{16}$, $CHal_3$, $CN$, $CO-NR^{14}R^{15}$, $CO-R^{13}$, $Hal$, $NO_2$, $NR^{16}C(=NR^{13})NR^{14}R^{15}$, $NR^{16}-C(O)-NR^{14}R^{15}$, $NR^{16}-C(O)-OR^{14}$, $NR^{16}-C(O)-R^{14}$, $NR^{14}R^{15}$, $NR^{16}-SO_2-NR^{14}R^{15}$, $NR^{16}-SO_2-R^{13}$, $O-C_{1-6}$-alkylene-$C(O)-NR^{14}R^{15}$, $O-C(O)-NR^{14}R^{15}$, $OC(O)-R^{13}$, $OR^{13}$, $S(O)_t-C_{1-6}$-alkylene-$C(O)-NR^{14}R^{15}$, $S(O)_t-C_{1-6}$-alkylene-$C(O)-OR^{13}$, $S(O)_t-C(O)-NR^{14}R^{15}$, $S(O)_t-C(O)-OR^{13}$, $S(O)_tR^{13}$, $SO_2-NR^{14}R^{15}$, and $SO_2OR^{13}$. In a preferred embodiment $R^4$, $R^5$, $R^6$, and $R^7$ are independently selected from the group consisting of hydrogen and $C_{1-6}$-alkyl. In an even more preferred embodiment $R^4$, $R^5$, $R^6$, and $R^7$ are hydrogen.

p is 1 or 2. In a preferred embodiment p is 1.

In the formula (b) $R^{12}$ is selected from the group consisting of $C(=NOR^{13})-R^{14}$, $C(=NR^{13})-NR^{14}NR^{15}$, $C(O)-C(=NR^{13})-NR^{14}NR^{15}$, $C(O)-NR^{14}R^{15}$, $C(O)-OR^{13}$, $R^{13}$, $S(O)_tNR^{14}R^{15}$, and $S(O)_tR^{13}$. In a preferred embodiment $R^{12}$ is $R^{13}$. In a more preferred embodiment $R^{12}$ is selected from the group consisting of hydrogen and $C_{1-6}$-alkyl. In an even more preferred embodiment $R^{12}$ is hydrogen.

$R^8$, $R^9$, $R^{10}$, and $R^{11}$ are independently selected from the group consisting of hydrogen, $C_{1-6}$-alkylene-$C(=NR^{13})NHR^{14}$, $C_{1-6}$-alkylene-$C(O)-NH-CN$, $C_{1-6}$-alkylene-$C(O)-NR^{16}-C_{1-6}$-alkylene-$NR^{14}R^{15}$, $C_{1-6}$-alkylene-$C(O)-NR^{16}-NR^{14}R^{15}$, $C_{1-6}$-alkylene-$C(O)-NR^{14}R^{15}$, $C_{1-6}$-alkylene-$C(O)-OR^{13}$, $C_{1-6}$-alkylene-$NR^{16}C(=NR^{13})NR^{14}R^{15}$, $C_{1-6}$-alkylene-$NR^{16}-C(O)-NR^{14}R^{15}$, $C_{1-6}$-alkylene-$NR^{16}-C(O)OR^{14}$, $C_{1-6}$-alkylene-$NR^{16}-C(O)R^{14}$, $C_{1-6}$-alkylene-$NR^{14}R^{15}$, $C_{1-6}$-alkylene-$NR^{16}-SO_2-NR^{14}R^{15}$, $C_{1-6}$-alkylene-$NR^{16}-SO_2-R^{14}$, $C(=NR^{13})-NHR^{14}$, $C(O)-NH-CN$, $C(O)-NR^{16}-C_{1-6}$-alkylene-$NR^{14}R^{15}$, $C(O)-NR^{16}-NR^{14}R^{15}$, $C(O)-NR^{14}R^{15}$, $C(O)-OH$, $C(O)-OR^{16}$, $CHal_3$, $CN$, $CO-NR^{14}R^{15}$, $CO-R^{13}$, $Hal$, $NO_2$, $NR^{16}C(=NR^{13})NR^{14}R^{15}$, $NR^{16}-C(O)-NR^{14}R^{15}$, $NR^{16}-C(O)-OR^{14}$, $NR^{16}C(O)-R^{14}$, $NR^{14}R^{15}$, $NR^{16}-SO_2-NR^{14}R^{15}$, $NR^{16}-SO_2-R^{13}$, $O-C_{1-6}$-alkylene-$C(O)-NR^{14}R^{15}$, $O-C(O)-NR^{14}R^{15}$, $OC(O)-R^{13}$, $OR^{13}$, $S(O)_t-C_{1-6}$-alkylene-$C(O)-NR^{14}R^{15}$, $S(O)_t-C_{1-6}$-alkylene-$C(O)-OR^{13}$, $S(O)_t-C(O)-NR^{14}R^{15}$, $S(O)_t-C(O)-OR^{13}$, $S(O)_tR^{13}$, $SO_2-NR^{14}R^{15}$, and $SO_2OR^{13}$. In a preferred embodiment $R^8$, $R^9$, $R^{10}$, and $R^{11}$ are independently selected from the group consisting of hydrogen and $C_{1-6}$-alkyl. In an even more preferred embodiment $R^8$, $R^9$, $R^{10}$, and $R^{11}$ are hydrogen.

q is 0, 1 or 2. In a preferred embodiment q is 1 because these compounds have improved solubility compared to the compounds in which q is 2.

t is 1 or 2.

$R^1$ and $R^2$ are independently selected from the group consisting of hydrogen, $C_{1-6}$-alkyl, $C_{5-10}$-cycloalkyl, $C_{5-10}$-cycloalkyl-$C_{1-6}$-alkyl, 5- to 10-membered heterocycloalkyl, haloalkyl having 1 to 6 carbon atoms, $C_{5-10}$-heterocycloalkyl-$C_{1-6}$-alkyl, $C_{2-6}$-alkenyl, $C_{5-10}$-aryl, 5- to 10-membered heteroaryl, $C_{5-10}$-aryl-$C_{1-6}$-alkyl, 5- to 10-membered heteroaryl-$C_{1-6}$-alkyl or aminoalkyl wherein the alkyl group has 1 to 6 carbon atoms, wherein alkyl, cycloalkyl, cycloalkylalkyl, heterocycloalkyl, haloalkyl, heterocycloalkylalkyl, alkenyl, alkynyl, aryl, heteroaryl, arylalkyl, heteroarylalkyl and aminoalkyl, which can optionally be substituted, or $R^1$ and $R^2$ when taken together with the nitrogen to which they are attached can form a 3- to 8-membered ring which may optionally contain one or more additional heteroatoms selected from O, S, or $NR^3$ and wherein the 3- to 8-membered ring may be optionally substituted. In a preferred embodiment $R^1$ and $R^2$ are independently selected from the group consisting of hydrogen, $C_{1-6}$-alkyl, $C_{5-10}$-cycloalkyl, and $C_{5-10}$-aryl. In a more preferred embodiment $R^1$ and $R^2$ are independently selected from the group consisting of hydrogen, $C_{1-6}$-alkyl, and phenyl. Most preferably $R^1$ and $R^2$ are independently selected from the group consisting of hydrogen and $C_{1-6}$-alkyl. Even more preferably $R^1$ is hydrogen and $R^2$ is methyl.

$R^{16}$ is independently selected from the group consisting of $C(=NOR^{13})-R^{14}$, $C(=NR^{13})-NR^{14}R^{15}$, $C(O)-C(=NR^{13})-NR^{14}R^{15}$, $C(O)-NR^{14}R^{15}$, $C(O)-OR^{13}$, $R^{13}$, $S(O)_tNR^{14}R^{15}$, and $S(O)_tR^{13}$. In a preferred embodiment $R^{16}$ is $R^{13}$. In a more preferred embodiment $R^{16}$ is selected from the group consisting of hydrogen and $C_{1-6}$-alkyl. In an even more preferred embodiment $R^{16}$ is hydrogen.

$R^{13}$ is independently selected from the group consisting of hydrogen, $C_{1-6}$-alkyl, $C_{5-10}$-cycloalkyl, $C_{5-10}$-cycloalkyl-$C_{1-6}$-alkyl, 5- to 10-membered heterocycloalkyl, haloalkyl having 1 to 6 carbon atoms, 5- to 10-membered heterocycloalkyl-$C_{1-6}$-alkyl, $C_{2-6}$-alkynyl, $C_{5-10}$-aryl, 5- to 10-membered heteroaryl, $C_{5-10}$-aryl-$C_{1-6}$-alkyl, 5- to 10-membered heteroaryl-$C_{1-6}$-alkyl or aminoalkyl wherein the alkyl group has 1 to 6 carbon atoms, wherein alkyl, cycloalkyl, cycloalkylalkyl, heterocycloalkyl, haloalkyl, heterocycloalkylalkyl, alkenyl, alkynyl, aryl, heteroaryl, arylalkyl, heteroarylalkyl and aminoalkyl, which can optionally be substituted. In a preferred embodiment $R^{13}$ is independently selected from the group consisting of hydrogen, $C_{1-6}$-alkyl, and $C_{5-10}$-aryl. In a more preferred embodiment $R^{13}$ is independently selected from hydrogen, $C_{1-6}$-alkyl, and phenyl, even more preferably from hydrogen, and $C_{1-6}$-alkyl.

$R^{14}$ and $R^{15}$ are independently selected from the group consisting of hydrogen, $C_{1-6}$-alkyl, $C_{5-10}$-cycloalkyl, $C_{5-10}$-cycloalkyl-$C_{1-6}$-alkyl, 5- to 10-membered heterocycloalkyl, haloalkyl having 1 to 6 carbon atoms, 5- to 10-membered heterocycloalkyl-$C_{1-6}$-alkyl, $C_{2-6}$-alkynyl, $C_{5-10}$-aryl, 5- to 10-membered heteroaryl, $C_{5-10}$-aryl-$C_{1-6}$-alkyl, 5- to 10-membered heteroaryl-$C_{1-6}$-alkyl or aminoalkyl wherein the alkyl group has 1 to 6 carbon atoms, wherein alkyl, cycloalkyl, cycloalkylalkyl, heterocycloalkyl, haloalkyl, heterocycloalkylalkyl, alkenyl, alkynyl, aryl, heteroaryl, arylalkyl, heteroarylalkyl and aminoalkyl, which can optionally be substituted. In a preferred embodiment $R^{14}$ and $R^{15}$ are independently selected from the group consisting of hydrogen, $C_{1-6}$-alkyl, and $C_{5-10}$-aryl. In a more preferred embodiment $R^{14}$ and $R^{15}$ are independently selected from hydrogen, $C_{1-6}$-alkyl, and phenyl, even more preferably from hydrogen, and $C_{1-6}$-alkyl.

In the case of $NR^{14}R^{15}$ $R^{14}$ and $R^{15}$ when taken together with the nitrogen to which they are attached can form a 3- to 8-membered ring which may optionally contain one or more additional heteroatoms selected from O, S, or $NR^3$ and wherein the 3- to 8-membered ring may be optionally substituted. In this embodiment the 3- to 8-membered ring can be, e.g., pyrrolidine, pyrrole, piperidine or pyridine.

Preferred compounds of the present invention are

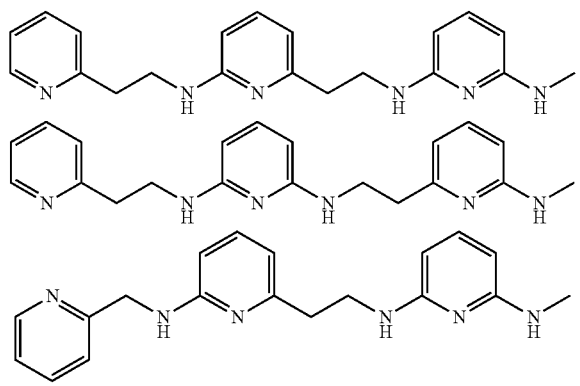

The compounds of the present invention which have the general formula (I) simultaneously have good pharmaceutical activity and good solubility. Though not wishing to be bound by the following theory, this is believed to be due to the presence of 3 pyridine rings and the 2,6-diaminopyridine substructure.

The compounds of the present invention can be prepared according to conventional methods, which are, e.g., similar to those disclosed in WO 2008/061795.

The compounds of the present invention can be synthesized by the general methods shown in Schemes 1 to 8. These methods are given as illustrative examples and are not limiting.

General Synthetic Scheme for the Preparation of Amine Building Blocks Containing Two Pyridyl Moieties with x=1 or 2.

Commercially available 2-bromo-6-methyl-pyridine was treated with lithiumdiisoproylamine in a suitable solvent at −78° C. to generate the corresponding anion.

Reaction of the anion at −78° C. with dimethylformamide and treatment of the reaction mixture with sodium borohydride yielded the corresponding hydroxyl derivative with a one carbon atom elongated side chain after purification. Protection of the hydroxyl moiety with triisopropylsilyl chloride in a suitable solvent and using a suitable base afforded the protected alcohol after purification. Reaction of the bromo-substituent of the protected alcohol with an appropriate amine employing Buchwald amination conditions (Pd-catalyst, ligand, base and solvent) afforded the coupling product after purification. Boc-protection of the amine moiety was achieved by heating the starting material with di-tert-butyl dicarbonate and subsequent purification. The silyl-protecting group was removed by tetra-n-butyl ammonium fluoride to afford the hydroxy derivative after purification. After activation of the hydroxyl moiety with methylsulfonylchloride in a suitable solvent and using a suitable base, the intermediate methylsulfonyl-derivative was converted to the corresponding azide derivative by heating with sodium azide in a suitable solvent. Purification afforded the desired azide derivative. The azide derivative was treated with triphenylphosphine employing Staudinger reaction conditions to yield the corresponding amine. Purification afforded the desired amine building block.

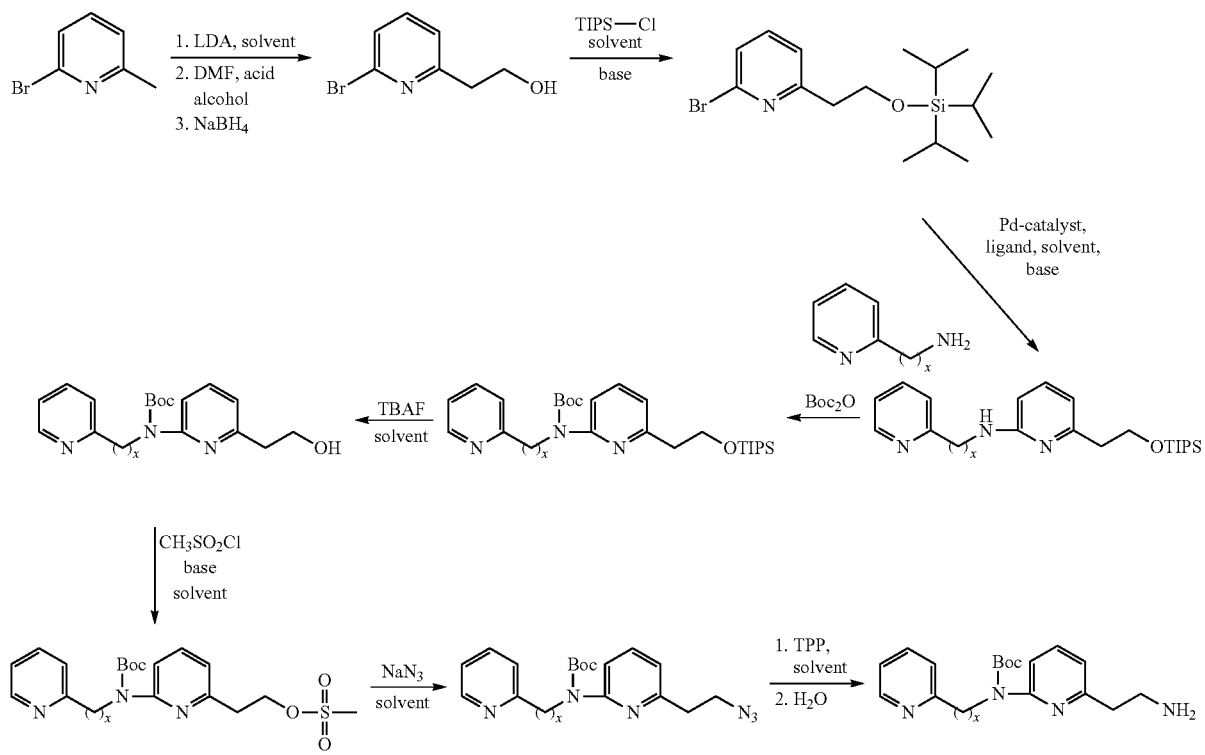

Scheme 1

General Synthetic Scheme for the Alternative Preparation of an Amine Building Block Containing Two Pyridyl with a C$_2$-Linker

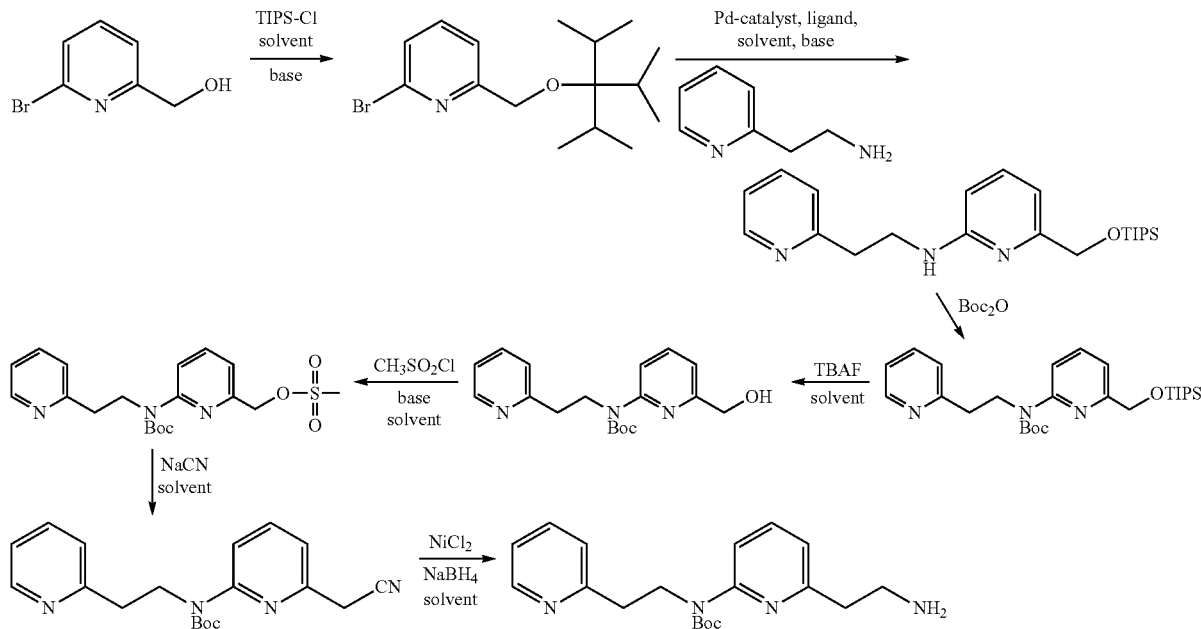

Scheme 2

Protection of the hydroxyl moiety of commercially available (6-bromopyridin-2-yl)methanol with triisopropylsilyl chloride in a suitable solvent and using a suitable base afforded the protected alcohol after purification. Reaction of the bromo-substituent of the protected alcohol with an appropriate amine employing Buchwald amination conditions (Pd-catalyst, ligand, base and solvent) afforded the coupling product after purification. Boc-protection of the amine moiety was achieved by heating the starting material with di-tert-butyl dicarbonate and subsequent purification. The silyl-protecting group was removed by tetra-n-butyl ammonium fluoride to afford the hydroxy derivative after purification. After activation of the hydroxyl moiety with methylsulfonylchloride in a suitable solvent and using a suitable base, the intermediate methylsulfonyl derivative was converted to the corresponding nitrile derivative by heating with sodium cyanide in a suitable solvent. Purification afforded the desired nitrile derivative. Treatment of the nitrile derivative with nickel(II)-chloride and sodium borohydride in a suitable solvent followed by purification afforded the desired amine building block.

General Synthetic Scheme for the Preparation of an Amine Building Block Containing Two Pyridyl Moieties with C$_3$-Linkers

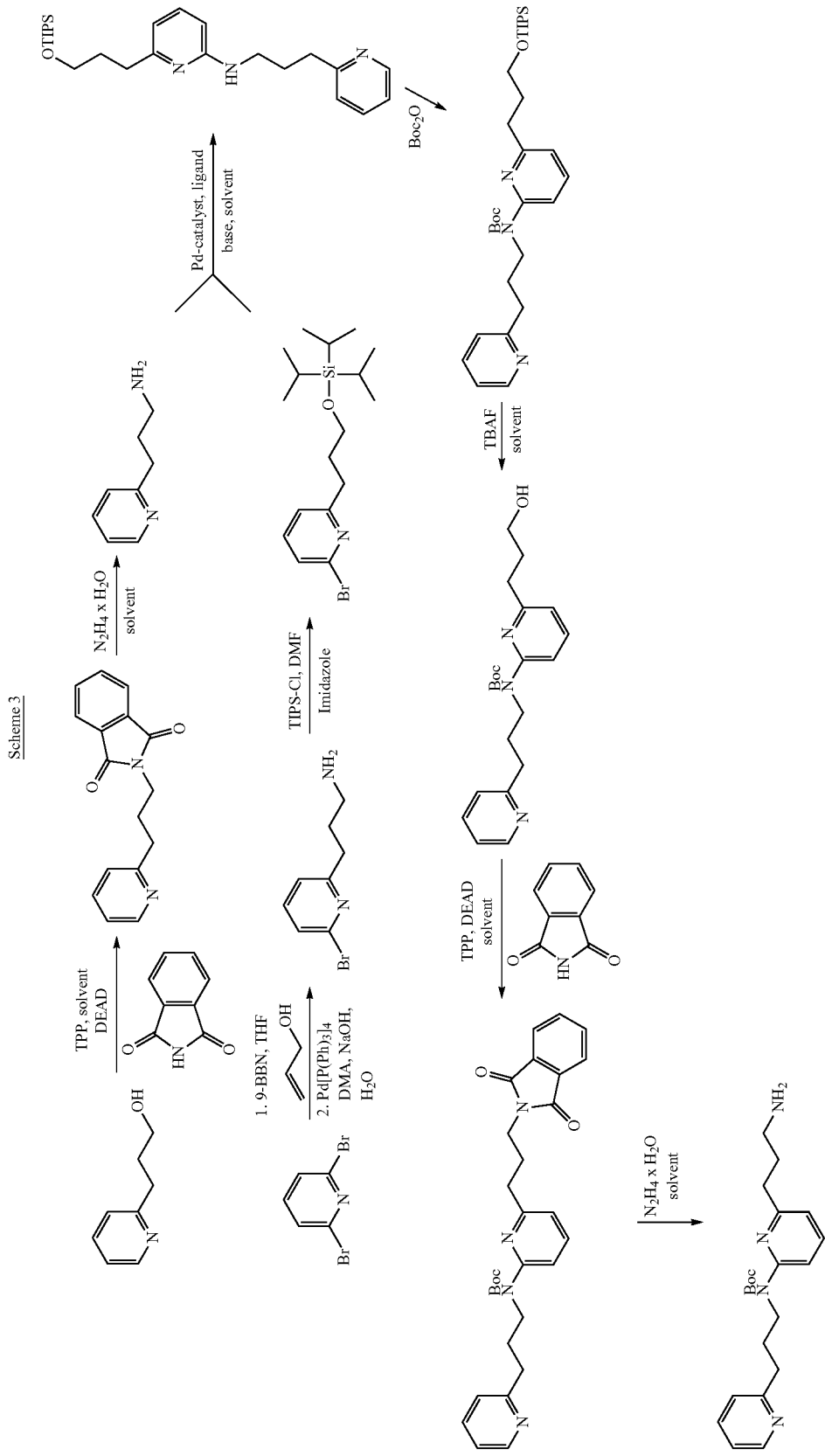

Commercially available 3-(pyridin-2-yl)propan-1-ol was converted to the corresponding amine derivative via Mitsunobu reaction employing phthalimide followed by treatment of the purified intermediate with hydrazine hydrate in a suitable solvent. Purification afforded the desired amine with a C$_3$-linker. Commercially available 2,6-dibromopyridine was allowed to react with the addition product of allylalcohol and 9-BBN in a suitable solvent employing a suitable Pd-catalyst in an appropriate solvent mixture to afford the desired alkylation product after purification. Protection of the hydroxyl moiety with triisopropylsilyl chloride in a suitable solvent and using a suitable base afforded the protected alcohol after purification. Reaction of the bromo-substituent of the protected alcohol with an appropriate amine employing Buchwald amination conditions (Pd-catalyst, ligand, base and solvent) afforded the coupling product after purification. Boc-protection of the amine moiety was achieved by heating the starting material with di-tert-butyl dicarbonate and subsequent purification. The silyl-protecting group was removed by tetra-n-butyl ammonium fluoride to afford the hydroxy derivative after purification. The hydroxy derivative was converted to the corresponding amine derivative via Mitsunobu reaction employing phthalimide followed by treatment of the purified intermediate with hydrazine hydrate in a suitable solvent. Purification afforded the desired amine building block with C$_3$-linkers.

General Synthetic Scheme for the Preparation of an Amine Building Block Containing One Pyridyl Moiety Commercially available 2-amino-6-methyl-pyridine was heated with di-tert-butyl dicarbonate to afford the mono-Boc-protected derivative after purification. The Boc-derivative was treated with lithiumdiisoproylamine in a suitable solvent at −78° C. to generate the corresponding anion. Reaction of the anion at −78° C. with dimethylformamide and treatment of the reaction mixture with sodium borohydride yielded the corresponding hydroxyl derivative with a one carbon atom elongated side chain after purification. After activation of the hydroxyl moiety with methylsulfonylchloride in a suitable solvent and using a suitable base, the intermediate methylsulfonyl derivative was converted to the corresponding azide derivative by heating with sodium azide in a suitable solvent. Purification afforded the desired azide derivative. The mono-Boc-amino substituent of the azide derivative was treated with sodium hydride in a suitable solvent followed by reaction with methyliodide to afford the N-methylated azide derivative after purification. The N-methylated azide derivative was treated with triphenylphosphine employing Staudinger reaction conditions to yield the corresponding amine. Purification afforded the desired amine building block.

General Synthetic Scheme for the Preparation of a Bromo Building Block Containing One Pyridyl Moiety Scheme 5

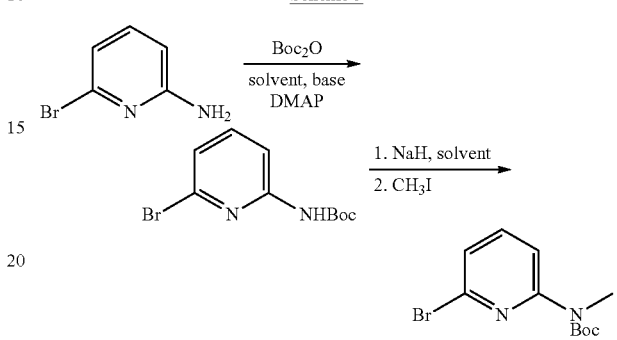

Commercially available 2-amino-6-bromo-pyridine was treated with di-tert-butyl dicarbonate, a suitable base and 4-dimethylamino pyridine in an appropriate solvent to afford the mono-Boc-derivative after purification. Treatment of the mono-Boc-derivative with sodium hydride in a suitable solvent followed by reaction with methyl iodide afforded the desired bromo building block after purification.

General Synthetic Scheme for the Preparation of a Bromo Building Block Containing Two Pyridyl Moieties Scheme 4

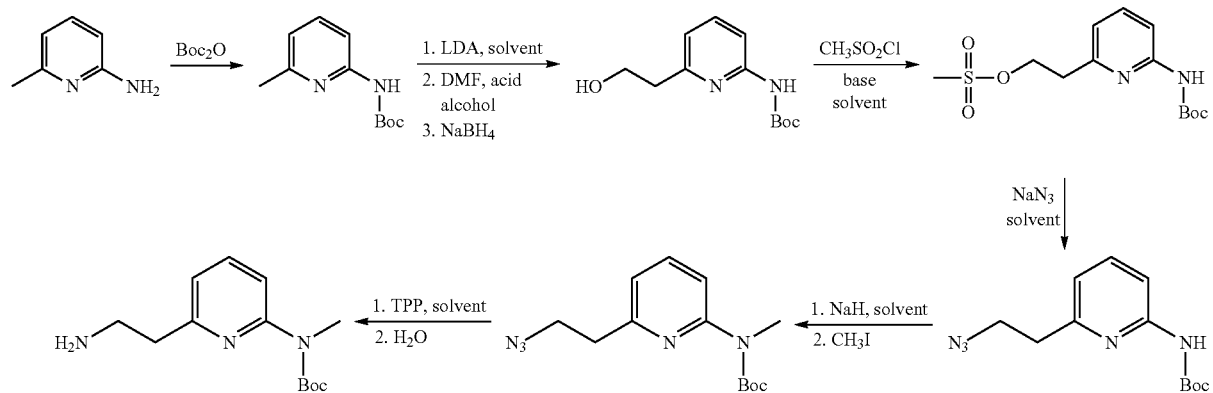

Scheme 6

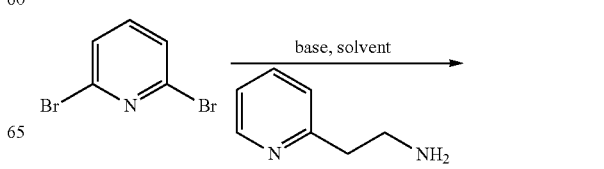

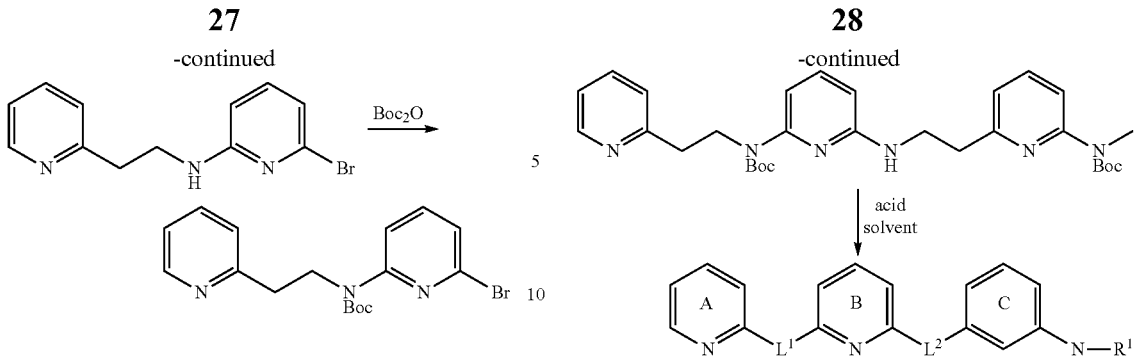

Commercially available 2,6-dibromopyridine was heated with an appropriate amine and a suitable base in a suitable solvent to afford the mono-amination product after purification. Heating of the amination product with di-tert-butyl dicarbonate afforded the desired bromo building block after purification.

General Synthetic Scheme for the Preparation of Compounds with x=1, 2 or 3 and y=1 or 2

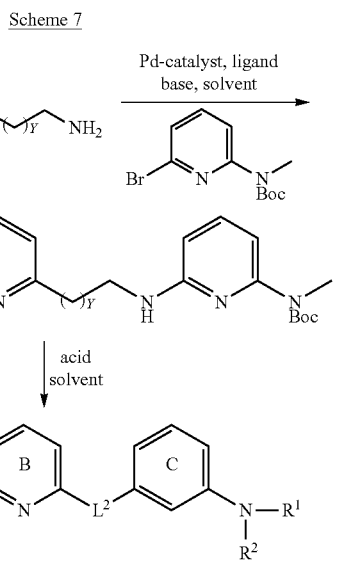

Using the appropriate amine and bromo building block from above in a Pd-catalyzed amination reaction employing Buchwald conditions (Pd-catalyst, ligand, base, solvent), the desired amination product was obtained after purification. Cleavage of the Boc-protecting groups with acid in a suitable solvent afforded the desired final compound after lyophilization.

General Synthetic Scheme for the Preparation of Compounds of this Invention

Using the appropriate amine and bromo building block from above in a Pd-catalyzed amination reaction employing Buchwald conditions (Pd-catalyst, ligand, base, solvent), the desired amination product was obtained after purification. Cleavage of the Boc-protecting groups with acid in a suitable solvent afforded the desired final compound after lyophilization.

While it is possible for the compounds of the present invention to be administered alone, it is preferable to formulate them into a pharmaceutical composition in accordance with standard pharmaceutical practice. Thus the invention also provides a pharmaceutical composition which comprises a therapeutically effective amount of a compound of formula (I) in admixture with a pharmaceutically acceptable excipient.

Pharmaceutically acceptable excipients are well known in the pharmaceutical art, and are described, for example, in Remington's Pharmaceutical Sciences, 15$^{th}$ Ed., Mack Publishing Co., New Jersey (1991). The pharmaceutical excipient can be selected with regard to the intended route of administration and standard pharmaceutical practice. The excipient must be acceptable in the sense of being not deleterious to the recipient thereof.

Pharmaceutically useful excipients that may be used in the formulation of the pharmaceutical composition of the present invention may comprise, for example, carriers, vehicles, diluents, solvents such as monohydric alcohols such as ethanol, isopropanol and polyhydric alcohols such as glycols and edible oils such as soybean oil, coconut oil, olive oil, safflower oil cottonseed oil, oily esters such as ethyl oleate, isopropyl myristate, binders, adjuvants, solubilizers, thickening agents, stabilizers, disintegrants, glidants, lubricating agents, buffering agents, emulsifiers, wetting agents, suspending agents, sweetening agents, colorants, flavors, coating agents, preservatives, antioxidants, processing agents, drug delivery modifiers and enhancers such as calcium phosphate, magnesium state, talc, monosaccharides, disaccharides, starch, gelatine, cellulose, methylcellulose, sodium carboxymethyl cellulose, dextrose, hydroxypropyl-B-cyclodextrin, polyvinylpyrrolidone, low melting waxes, and ion exchange resins.

The routes for administration (delivery) of the compounds of the invention include, but are not limited to, one or more of: oral (e.g. as a tablet, capsule, or as an ingestible solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, epidural and sublingual.

In ophthalmic administration, the compounds can be administered e.g. in the form of eye drops.

For example, the compounds can be administered orally in the form of tablets, capsules, ovules, elixirs, solutions or suspensions, which may contain flavoring or coloring agents, for immediate-, delayed-, modified-, sustained-, pulsed- or controlled-release applications.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included. Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

If the compounds of the present invention are administered parenterally, then examples of such administration include one or more of: intravenously, intraarterially, intraperitoneally, intrathecally, intraventricularly, intraurethrally, intrasternally, intracranially, intramuscularly or subcutaneously administering the compounds; and/or by using infusion techniques. For parenteral administration, the compounds are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

As indicated, the compounds of the present invention can be administered intranasally or by inhalation and are conveniently delivered in the form of a dry powder inhaler or an aerosol spray presentation from a pressurized container, pump, spray or nebulizer with the use of a suitable propellant, e.g. dichlorodifluoromethane, trichlorofluoromethane, dichlorotetra-fluoroethane, a hydrofluoroalkane such as 1,1,1,2-tetrafluoroethane (HFA134AT) or 1,1,1,2,3,3,3-heptafluoropropane (HFA 227EA), carbon dioxide or other suitable gas. In the case of a pressurized aerosol, the dosage unit may be determined by providing a valve to deliver a metered amount. The pressurized container, pump, spray or nebulizer may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of the compound and a suitable powder base such as lactose or starch.

Alternatively, the compounds of the present invention can be administered in the form of a suppository or pessary, or it may be applied topically in the form of a gel, hydrogel, lotion, solution, cream, ointment or dusting powder. The compounds of the present invention may also be dermally or transdermally administered, for example, by the use of a skin patch.

They may also be administered by the pulmonary or rectal routes. They may also be administered by the ocular route. For ophthalmic use, the compounds can be formulated as micronized suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the present invention can be formulated as a suitable ointment containing the active compound suspended or dissolved in, for example, a mixture with one or more of the following: mineral oil, liquid petrolatum, white petrolatum, propylene glycol, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Due to their high solubility the compounds of the present invention are particularly suitable for routes of administration in which the compounds are delivered in a liquid medium. Examples are eye drops and other solutions.

Typically, a physician will determine the actual dosage which will be most suitable for an individual subject. The specific dose level and frequency of dosage for any particular individual may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

A proposed dose of the compounds according to the present invention for administration to a human (of approximately 70 kg body weight) is 0.1 mg to 1 g, preferably 1 mg to 500 mg of the active ingredient per unit dose. The unit dose may be administered, for example, 1 to 4 times per day. The dose will depend on the route of administration. It will be appreciated that it may be necessary to make routine variations to the dosage depending on the age and weight of the patient as well as the severity of the condition to be treated. The precise dose and route of administration will ultimately be at the discretion of the attendant physician or veterinarian.

The compounds of the invention may also be used in combination with other therapeutic agents. When a compound of the invention is used in combination with a second therapeutic agent active against the same disease the dose of each compound may differ from that when the compound is used alone.

The combinations referred to above may conveniently be presented for use in the form of a pharmaceutical formulation. The individual components of such combinations may be administered either sequentially or simultaneously in separate or combined pharmaceutical formulations by any convenient route. When administration is sequential, either the compound of the invention or the second therapeutic agent may be administered first. When administration is simultaneous, the combination may be administered either in the same or different pharmaceutical composition. When combined in the same formulation it will be appreciated that the two compounds must be stable and compatible with each other and the other components of the formulation. When formulated separately they may be provided in any convenient formulation, conveniently in such manner as are known for such compounds in the art.

The pharmaceutical compositions of the invention can be produced in a manner known per se to the skilled person as described, for example, in Remington's Pharmaceutical Sciences, 15$^{th}$ Ed., Mack Publishing Co., New Jersey (1991).

Diseases that can be treated with the compounds of the present invention can be associated with the formation of abnormal protein structures, in particular abnormal β-sheet structures. In the context of the present invention, an abnormal protein structure is a protein structure that arises when a protein or peptide refolds from the three-dimensional structure, which it generally adopts in healthy individuals, into a different three-dimensional structure, which is associated with a pathological condition. Likewise, an abnormal β-sheet structure in the context of the present invention is a β-sheet structure that arises when a protein or peptide refolds from the three-dimensional structure, which it generally adopts in healthy individuals, into a β-sheet structure, which is associated with a pathological condition.

In particular, in one embodiment diseases that can be treated with the compounds of the present invention are diseases or conditions associated with amyloid or amyloid-like proteins.

This group of diseases and disorders include amyloid-associated ocular diseases that target different tissues of the eye, such as the visual cortex, including cortical visual deficits; the anterior chamber and the optic nerve, including glaucoma; the lens, including cataract due to beta-amyloid deposition; the vitreous, including ocular amyloidoses; the retina, including primary retinal degenerations and macular degeneration, in particular age-related macular degeneration; the optic nerve, including optic nerve drusen, optic neuropathy and optic neuritis; and the cornea, including lattice dystrophy.

The ability of a compound to inhibit the aggregation of Aβ can, for example, be determined using fluorescence correlation spectroscopy as described in Rzepecki et al., J. Biol. Chem., 2004, 279(46), 47497-47505 or by using the thioflavin T spectrofluorescence assay.

In another embodiment the compounds of the present invention can be used for treating or alleviating the effects of ocular diseases associated with pathological abnormalities/changes in the tissues of the visual system, particularly associated with amyloid-beta-related pathological abnormalities/changes in the tissues of the visual system, such as, for example, neuronal degradation. Said pathological abnormalities may occur, for example, in different tissues of the eye, such as the visual cortex leading to cortical visual deficits; the anterior chamber and the optic nerve leading to glaucoma; the lens leading to cataract due to beta-amyloid deposition; the vitreous leading to ocular amyloidoses; the retina leading to primary retinal degeneration and macular degeneration, for example age-related macular degeneration; the optic nerve leading to optic nerve drusen, optic neuropathy and optic neuritis; and the cornea leading to lattice dystrophy. The compounds of the present invention have proven to be particularly suitable for treating or preventing glaucoma.

The compounds according to the present invention can also be provided in the form of a mixture with at least one further biologically active compound and/or a pharmaceutically acceptable carrier and/or a diluent and/or an excipient. The compound and/or the further biologically active compound are preferably present in a therapeutically effective amount.

The nature of the further biologically active compound will depend on the intended use of the mixture. The further biologically active substance or compound may exert its biological effect by the same or a similar mechanism as the compound according to the invention or by an unrelated mechanism of action or by a multiplicity of related and/or unrelated mechanisms of action.

Generally, the further biologically active compound may include beta-blockers, carbonic anhydrase inhibitors, alpha- or beta-adrenergic agonists, prostaglandins, parasympahomimetics, cholinesterase inhibitors, acetylcholine synthesis, storage or release enhancers, acetylcholine postsynaptic receptor agonists, or N-methyl-D-aspartate glutamate receptor antagonists. In particular, the further biologically active compound can be selected from the group consisting of a compound used in the treatment of amyloidoses, compounds against oxidative stress, anti-apoptotic compounds, metal chelators, inhibitors of DNA repair such as pirenzepin and metabolites, 3-amino-1-propanesulfonic acid (3APS), 1,3-propanedisulfonate (1,3PDS), α-secretase activators, β- and γ-secretase inhibitors, neurotransmitter, β-sheet breakers, attractants for amyloid beta clearing/depleting cellular components, inhibitors of N-terminal truncated amyloid beta including pyroglutamated amyloid beta 3-42, anti-inflammatory molecules, or cholinesterase inhibitors (ChEIs) such as tacrine, rivastigmine, donepezil, and/or galantamine, Ml agonists, other drugs including any amyloid modifying drug and nutritive supplement, an antibody, including any functionally equivalent antibody or functional parts thereof, an Aβ antigenic peptide fragment consisting of a single or repetitive stretch of a plurality of contiguous amino acid residues from the N-terminal part of the Aβ peptide.

In a further embodiment, the mixtures according to the invention may comprise memantine together with a compound according to the present invention and, optionally, a pharmaceutically acceptable carrier and/or a diluent and/or an excipient.

In still another embodiment of the invention mixtures are provided that comprise as a further biologically active compound a intraocular pressure lowering agent, together with a compound according to the invention and, optionally, a pharmaceutically acceptable carrier and/or a diluent and/or an excipient.

In one preferred embodiment the further biologically active compound is an antibody including any functionally equivalent antibody or functional parts thereof. The antibody can preferably be monoclonal, chimeric or humanized.

In a further aspect of the invention, a mixture is provided comprising in addition to the compound of the invention an antibody including functional parts thereof, or, more particularly, a monoclonal antibody including functional parts thereof, which recognizes and binds to amyloid β (Aβ), particularly to the native conformation of amyloid β, that is to amyloid oligomers and fibers, but not to not linearized amyloid species.

In particular, said antibodies are capable of inhibiting, in vitro and in vivo, the aggregation of amyloidogenic monomeric peptides, specifically β-amyloid monomeric peptides such as, for example, Aβ monomeric peptides which include amino acids 1-39; 1-40, 1-41, 1-42, or 1-43 of β-amyloid, but especially Aβ$_{1-42}$ monomeric peptides, into high molecular polymeric amyloid fibrils or filaments. Through the inhibition of the aggregation of amyloidogenic monomeric peptides these antibodies are capable of preventing or slowing down the formation of amyloid plaques, particularly the amyloid form (1-42), which is know to become insoluble by change of secondary conformation and to be the major part of amyloid plaques in brains of diseased animals or humans.

In another aspect of the invention, the mixture comprises antibodies which, upon co-incubation with preformed high molecular polymeric amyloid fibrils or filaments formed by the aggregation of amyloid monomeric peptides, specifically β-amyloid monomeric peptides such as, for example, Aβ monomeric peptides which include amino acids 1-39; 1-40, 1-41, 1-42, or 1-43 of β-amyloid, but especially $A\beta_{1-42}$ monomeric peptides, are capable of disaggregating said high molecular polymeric amyloid fibrils or filaments. Through the disaggregation of amyloidogenic polymeric fibrils or filaments these antibodies are capable of preventing or slowing down the formation of amyloid plaques which leads to an alleviation of the symptoms associated with the disease and a delay or reversal of its progression.

In still another aspect of the invention, the mixture comprises an antibody, but especially a monoclonal antibody or functional parts thereof, which antibody is bifunctional or bispecific in that it exhibit both an aggregation inhibition property as well as a disaggregation property as defined herein before, particularly paired with a high degree of conformational sensitivity.

In one embodiment, the mixture comprises an antibody which recognizes and binds to a conformational epitope, particularly a conformational epitope which is present in the N-terminal part of the amyloid β peptide, particularly embedded into the following core region of the N-terminal part of the amyloid β peptide:

| Val- | His- | His- | Gln- | Lys- | Leu- | Val- | Phe- | Phe- | Ala- | Glu- | Asp- |
|------|------|------|------|------|------|------|------|------|------|------|------|
| 12   | 13   | 14   | 15   | 16   | 17   | 18   | 19   | 20   | 21   | 22   | 23   |

The antibody may particularly recognize an epitope localized in a region of the β-amyloid protein between amino acid residue 12 to 24, particularly between residues 14 to 23, more particularly between amino acid residues 14 and 20, comprising three distinct recognition and binding sites which residues are predominantly involved in the binding of the β-amyloid protein and located at position 16, 17, and at position 19 and 20, and at position 14, respectively.

In a specific embodiment the mixture of the present invention comprises, in addition to the compound of the invention, an antibody, particularly a bifunctional antibody, but especially a monoclonal antibody, particularly a bifunctional monoclonal antibody, including any functionally equivalent antibody or functional parts thereof, which antibody has the characteristic properties of an antibody produced by a hybridoma cell line selected from the group consisting of FP 12H3, FP 12H3-C2, and FP 12H3-G2 deposited on Dec. 1, 2005 and Dec. 9, 2005, respectively, as DSM ACC2752, DSM ACC 2750 and DSM ACC2751, respectively, ET 7E3 deposited on Dec. 8, 2005 as DSM ACC2755, and EJ 7H3 deposited on Dec. 8, 2005 as DSM ACC2756.

More particularly, the invention relates to an antibody including any functionally equivalent antibody or functional parts thereof produced by a hybridoma cell line selected from the group consisting of FP 12H3, FP 12H3-C2, and FP 12H3-G2 deposited on Dec. 1, 2005 and Dec. 9, 2005, respectively, as DSM ACC2752, DSM ACC 2750 and DSM ACC2751, respectively, ET 7E3 deposited on Dec. 8, 2005 as DSM ACC2755, and EJ 7H3 deposited on Dec. 8, 2005 as DSM ACC2756.

The above antibodies are described in the published International Application WO 2007/068412, which is incorporated herein by reference.

In a further aspect, the antibody which is comprised in the mixture according to the invention is a chimeric antibody or a fragment thereof, or a humanized antibody or a fragment thereof. These and further antibodies that can be suitably used within the mixtures according to the present invention are described, for example, in international application PCT/US2007/073504 filed Jul. 13, 2007.

If the antibody is a humanized antibody, it preferably exhibits a light chain and a heavy chain as depicted in SEQ ID NO: 2 and SEQ ID NO: 4 of International Application No. PCT/US2007/073504 or exhibits a light chain variable region and a heavy chain variable region as depicted in SEQ ID NO: 1 and SEQ ID NO: 3 of International Application No. PCT/US2007/073504. These sequences are also shown in the attached sequence listing.

In still another aspect of the invention, a mixture is provided which comprises, in addition to the compound according to the invention and as described herein before, a peptide fragment from the N-terminal part of the Aβ peptide, particularly an Aβ peptide fragment consisting of a single or repetitive stretch of between 13 and 15 contiguous amino acid residues from the N-terminal part of the Aβ peptide, but particularly an Aβ peptide fragment consisting of amino acid residues selected from the group consisting of residues 1-15, 1-14, and 1-13 from the N-terminal part of the Aβ peptide, more particularly of residue 1-15, including functionally equivalent fragments thereof, but especially a Aβ peptide fragment as mentioned herein before attached to, or incorporated or reconstituted in a carrier particle/adjuvant such as, for example, a liposome. The peptide fragment can be comprised in a vaccine composition. In particular, the peptide antigen is modified by a lipophilic or hydrophobic moiety, that facilitates insertion into the lipid bilayer of the liposome carrier/immune adjuvant, particularly by a lipophilic or hydrophobic moiety which functions as an anchor for the peptide in the liposome bilayer and has a dimension that leads to the peptide being positioned and stabilized in close proximity to the liposome surface.

In a further embodiment of the invention, the lipophilic or hydrophobic moiety is a fatty acid, a triglyceride or a phospholipid, but especially a fatty acid, a triglyceride or a phospholipid. In particular, the hydrophobic moiety is palmitic acid and the liposome preparation may in addition contain an adjuvant such as, for example, lipid A, alum, calcium phosphate, interleukin 1, and/or microcapsules of polysaccharides and proteins, but particularly a detoxified lipid A, such as monophosphoryl or diphosphoryl lipid A, or alum.

These and further compositions that can be suitably used in the mixtures of the present invention are described, for example, in the published International Application WO 2007/068411.

Diagnosis of an amyloid-associated disease or condition or of a predisposition to an amyloid-associated disease or condition in a patient may be achieved by detecting the specific binding of a compound according to the invention to the amyloid protein in a sample or in situ, which includes bringing the sample or a specific body part or body area suspected to contain the amyloid antigen into contact with a compound of the invention which binds the amyloid protein, allowing the compound of the invention to bind to the amyloid portein to form a compound/protein complex, detecting the formation of the compound/protein complex and correlating the presence or absence of the compound/protein complex with the presence or absence of amyloid protein in the sample or specific body part or area, optionally comparing the amount of said compound/protein complex to a normal control value, wherein an increase in the amount of said aggregate compared to a normal control value may indicate that said patient is suffering from or is at risk of developing an amyloid-associated disease or condition.

Monitoring minimal residual disease in a patient following treatment with acompound or a mixture according to the invention may be achieved by detecting the specific binding of a compound according to the invention to the amyloid protein in a sample or in situ, which includes bringing the sample or a specific body part or body area suspected to contain the amyloid antigen into contact with a compound of the invention which binds the amyloid protein, allowing the compound to bind to the amyloid protein to form an compound/protein complex, detecting the formation of the compound/protein complex and correlating the presence or absence of the compound/protein complex with the presence or absence of amyloid protein in the sample or specific body part or area, optionally comparing the amount of said compound/protein complex to a normal control value, wherein an increase in the amount of said aggregate compared to a normal control value may indicate that said patient may still suffer from a minimal residual disease.

Predicting responsiveness of a patient to a treatment with a compound or composition or a mixture according to the invention may be achieved by detecting the specific binding of a compound according to the invention to the amyloid protein in a sample or in situ, which includes bringing the sample or a specific body part or body area suspected to contain the amyloid protein into contact with a compound of the invention which binds the amyloid protein, allowing the compound to bind to the amyloid protein to form an compound/protein complex, detecting the formation of the compound/protein complex and correlating the presence or absence of the compound/protein complex with the presence or absence of amyloid protein in the sample or specific body part or area, optionally comparing the amount of said compound/protein complex before and after onset of the treatment, wherein an decrease in the amount of said aggregate may indicate that said patient has a high potential of being responsive to the treatment.

Biological samples that may be used in the diagnosis of an amyloid-associated disease or condition for diagnosing a predisposition to an amyloid-associated disease or condition or for monitoring minimal residual disease in a patient or for predicting responsiveness of a patient to a treatment with a compound or a composition or a mixture according to the invention and as described herein before are, for example, fluids such as serum, plasma, saliva, gastric secretions, mucus, cerebrospinal fluid, lymphatic fluid and the like or tissue or cell samples obtained from an organism such as neural, brain, cardiac or vascular tissue. For determining the presence or absence of the amyloid protein in a sample any immunoassay known to those of ordinary skill in the art (see Harlow and Lane, Antibodies: A Laboratory Manual (Cold Spring Harbor Laboratory, New York, 1988, 555 to 612) may be used such as, for example, assays which utilize indirect detection methods using secondary reagents for detection, ELISA's and immunoprecipitation and agglutination assays. A detailed description of these assays is, for example, given in WO96/13590 to Maertens and Stuyver, Zrein et al. (1998) and WO96/29605.

For in situ diagnosis, the compound or compostion or mixture according to the invention and as described herein before may be administered to the organism to be diagnosed by methods known in the art such as, for example, intravenous, intranasal, intraperitoneal, intracerebral, intraarterial injection such that a specific binding between the compound according to the invention and the amyloid antigen may occur. The compound/protein complex may be detected through a label attached to the compound.

The immunoassays used in diagnostic applications or in applications for diagnosing a predisposition to an amyloid-associated disease or condition or for monitoring minimal residual disease in a patient or for predicting responsiveness of a patient to a treatment with a compound or composition or a mixture according to the invention and as described herein before, typically rely on labelled antigens, antibodies, or secondary reagents for detection. These proteins or reagents can be labelled with compounds generally known to those skilled in the art including enzymes, radioisotopes, and fluorescent, luminescent and chromogenic substances including colored particles, such as colloidal gold and latex beads. Of these, radioactive labelling can be used for almost all types of assays and with most variations. Enzyme-conjugated labels are particularly useful when radioactivity must be avoided or when quick results are needed. Fluorochromes, although requiring expensive equipment for their use, provide a very sensitive method of detection. Antibodies useful in these assays include monoclonal antibodies, polyclonal antibodies, and affinity purified polyclonal antibodies.

Alternatively, the compound of the invention may be labelled indirectly by reaction with labelled substances that have an affinity for immunoglobulin, such as protein A or G or second antibodies. The antibody may be conjugated with a second substance and detected with a labelled third substance having an affinity for the second substance conjugated to the antibody. For example, the antibody may be conjugated to biotin and the antibody-biotin conjugate detected using labelled avidin or streptavidin. Similarly, the antibody may be conjugated to a hapten and the antibody-hapten conjugate detected using labelled anti-hapten antibody.

Those of ordinary skill in the art will know of these and other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al., 1976 (Clin. Chim. Acta 70:1-31), and Schurs, A. H. W. M., et al. 1977 (Clin. Chim Acta 81:1-40). Coupling techniques mentioned in the latter are the glutaraldehyde method, the periodate method, the dimaleimide method, and others, all of which are incorporated by reference herein.

Current immunoassays utilize a double antibody method for detecting the presence of an analyte, wherein the antibody is labelled indirectly by reactivity with a second antibody that has been labelled with a detectable label. The second antibody is preferably one that binds to antibodies of the animal from which the monoclonal antibody is derived. In other words, if the monoclonal antibody is a mouse antibody, then the labelled, second antibody is an anti-mouse antibody. For the monoclonal antibody to be used in the assay described below, this label is preferably an antibodycoated bead, particularly a magnetic bead. For the polyclonal antibody to be employed in the immunoassay described herein, the label is preferably a detectable molecule such as a radioactive, fluorescent or an electrochemiluminescent substance.

An alternative double antibody system, often referred to as fast format systems because they are adapted to rapid determinations of the presence of an analyte, may also be employed within the scope of the present invention. The system requires high affinity between the antibody and the analyte. According to one embodiment of the present invention, the presence of the amyloid antigen is determined using a pair of antibodies, each specific for amyloid antigen. One of said pairs of antibodies is referred to herein as a "detector antibody" and the other of said pair of antibodies is referred to herein as a "capture antibody". The monoclonal antibody can be used as either a capture antibody or a detector antibody. The monoclonal antibody can also be used as both capture and detector antibody, together in a single assay. One embodiment of the present invention thus uses the double antibody sandwich method for detecting amyloid antigen in a sample of biological fluid. In this method, the analyte (amyloid antigen) is sandwiched between the detector antibody and the capture antibody, the capture antibody being irreversibly immobilized onto a solid support. The detector antibody would contain a detectable label, in order to identify the presence of the antibody-analyte sandwich and thus the presence of the analyte.

Exemplary solid phase substances include, but are not limited to, microtiter plates, test tubes of polystyrene, magnetic, plastic or glass beads and slides which are well known in the field of radioimmunoassay and enzyme immunoassay. Methods for coupling antibodies to solid phases are also well known to those skilled in the art. More recently, a number of porous material such as nylon, nitrocellulose, cellulose acetate, glass fibers and other porous polymers have been employed as solid supports.

The plaque burden in the tissue and/or body fluid (such as the retinal ganglion cell layer of an animal, particularly a mammal, but especially a human suffering from an ocular disease associated with pathological abnormalities/changes in the tissues of the visual system, particularly associated with amyloid-beta-related pathological abnormalities/changes in the tissues of the visual system) can be calculated by methods known in the art such as that disclosed in Ding, J.-D. et al., "Targeting age-related macular degeneration with Alzheimer's disease based immunotherapies: Anti-amyloid-b antibody attenuates pathologies in an age-related macular degeneration mouse model", Vision Research (2007), doi:10.1016/j.visres.2007.07.025.

A compound according to the present invention can also be incorporated into a test kit for detecting an amyloid protein. The test kit typically comprises a container holding one or more compounds according to the present invention and instructions for using the compound for the purpose of binding to an amyloid protein to form a compound/protein complex and detecting the formation of the compound/protein complex such that presence or absence of the compound/protein complex correlates with the presence or absence of the amyloid protein.

The term "test kit" refers in general to any diagnostic kit known in the art. More specifically, the latter term refers to a diagnostic kit as described in Zrein et al. (1998).

EXAMPLES

The synthesis of compounds of the invention inhibiting the aggregation of $Ab_{1-42}$ and their biological activity assay are described in the following examples which are not intended to be limiting in any way.

The inhibition of aggregation of $Ab_{1-42}$ by the compounds of the present invention may be measured using any suitable assay known in the art. A standard in vitro assay for measuring the inhibition of aggregation is described.

Preparation Examples

All reagents and solvents were obtained from commercial sources and used without further purification. Proton ($^1$H) spectra were recorded on a 400 MHz NMR spectrometer in deuterated solvents. Mass spectra (MS) were recorded on a Finnigan MAT TSQ 7000 spectrometer. Chromatography was performed using silica gel (Fluka: Silica gel 60, 0.063-0.2 mm) and suitable solvents as indicated in specific examples. Thin layer chromatography (TLC) was carried out on silica gel plates with UV detection. Preparative thin layer chromatography (Prep-TLC) was conducted with 0.5 mm or 1 mm silica gel plates (Analtech: Uniplate, $F_{254}$) and the solvents indicated in the specific examples.

Preparation Example 1 (Compound 5 and Compound 13)

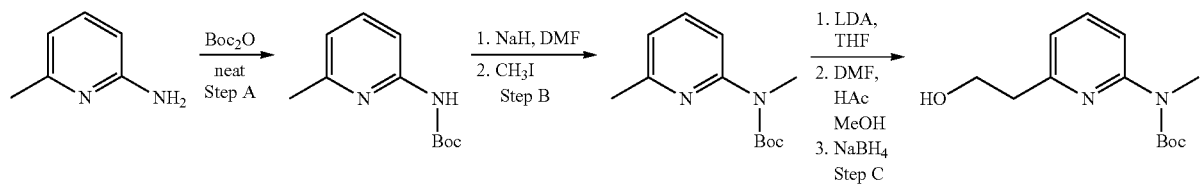

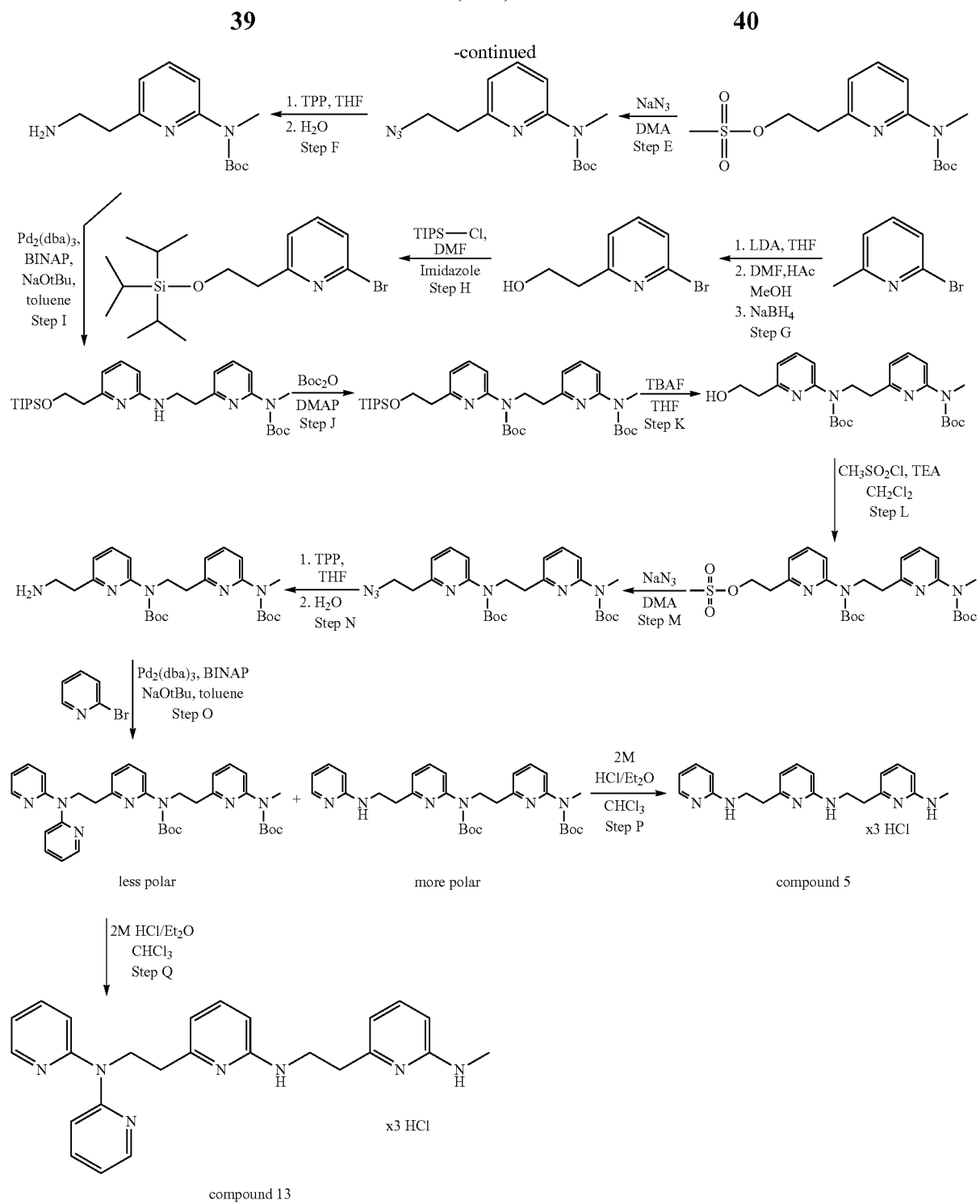

Step A

Commercially available 2 amino-6-picoline (10.8 g, 100 mmol) was treated with a solution of di-tert-butyl dicarbonate (26.2 g, 120 mmol) in dichloromethane (100 mL). The solvent was removed in vacuo and the residue was heated at ~70° C. in a sand bath overnight. The mixture was diluted with ethyl acetate (150 mL) and the organic phase washed with 10% citric acid solution (70 mL), saturated sodium bicarbonate (70 mL) and brine (70 mL). The organic phase was separated, dried over $Na_2SO_4$, filtered and the solvents were removed. The residue was purified by chromatography on silica using ethyl acetate/petrolether (10/90) to elute excess reagent, followed by ethylacetate/petrolether (20/80) to afford the desired compound as a colorless oil, which becomes a white solid by standing at room temperature (19 g, 91%).

$^1$H-NMR (400 MHz, $CDCl_3$): d=1.53 (s, 9H), 2.44 (s, 3H), 6.82 (d, 1H), 7.27 (br-s, 1H), 7.55 (t, 1H), 7.72 (d, 1H)

Step B

Sodium hydride (0.84 g, 35 mmol) was suspended in N,N'-dimethylformamide (50 mL) and the mixture was cooled to 0° C. At 0° C. a solution of the title compound from Step A above (6 g, 28.8 mmol) in N,N'-dimethylformamide (20 mL) was added over a period of 5 minutes. After the addition was completed, the reaction mixture was stirred at 0° C. for 15 minutes and then 60 minutes at room temperature. Then methyliodide (2.39 mL, 38.5 mmol) was added in one portion and the reaction mixture was stirred at room temperature overnight. The reaction mixture was diluted with ethyl acetate (150 mL) and 10% citric acid solution (150 mL). The organic phase was separated and the aqueous phase was extracted with ethylacetate (2×100 mL). The combined organic phase was washed with 10% citric acid solution (80 mL), saturated sodium bicarbonate (80 mL) and brine (80 mL). The organic phase was separated, dried over $Na_2SO_4$, filtered and the solvents were removed. The residue was purified by chromatography on silica using ethyl acetate/petrolether (10/90) to afford the desired compound as a pale yellow oil (4.75 g, 74%).

$^1$H-NMR (400 MHz, $CDCl_3$): d=1.53 (s, 9H), 2.48 (s, 3H), 3.38 (s, 3H), 6.87 (d, 1H), 7.40 (d, 1H), 7.52 (t, 1H)

Step C

A solution of LDA was prepared by adding a 2 M solution of n-butyllithium (12 mL, 24 mmol) at 0° C. to a stirred solution of N,N'-diisopropylamine (4 mL, 28.8 mmol) in tetrahydrofuran (60 mL). The mixture was stirred at 0° C. for 1 h and then cooled to −78° C. At −78° C. a solution of the title compound from Step B above (2.13 g, 9.6 mmol) in tetrahydrofuran (15 mL) was added over a period of 5 minutes. The mixture was stirred at −78° C. for 45 minutes and allowed to warm to −50° C. The mixture was then cooled to −78° C. and N,N'-dimethylformamide (0.76 mL, 10.3 mmol) was added. After 15 minutes at −78° C., methanol (8.4 mL) and acetic acid (0.59 mL, 12.8 mmol) were added. Then sodium borohydride (0.34 g, 9.4 mmol) was added at −78° C. and the mixture was stirred overnight and allowed to reach room temperature. The reaction mixture was diluted with ethylacetate (80 mL) and washed with a 10% citric acid solution (50 mL) and brine (50 mL). The organic phase was separated, dried over $Na_2SO_4$, filtered and the solvents were removed. The residue was purified by chromatography on silica using ethylacetate/petrolether (20/80) to elute starting material (0.7 g, 35% recovery), followed by ethylacetate/petrolether (60/40) to afford the title compound as a pale orange oil (1.08 g, 44%).

$^1$H-NMR (400 MHz, $CDCl_3$): d=1.56 (s, 9H), 2.98 (t, 2H), 3.37 (s, 3H), 4.05 (t, 2H), 6.88 (d, 1H), 7.53-7.60 (m, 2H)

Step D

The title compound from Step C above (1.07 g, 4.27 mmol) was dissolved in dichloromethane (10 mL) and triethylamine (1.32 mL, 9.4 mmol) was added. After the addition of methanesulfonylchloride (0.66 mL, 8.5 mmol), the reaction mixture was stirred at room temperature for 1 h. The mixture was diluted with dichloromethane (50 mL) and washed with 10% citric acid solution (20 mL), saturated sodium bicarbonate (20 mL) and brine (20 mL). The organic phase was separated, dried over $Na_2SO_4$, filtered and the solvents were removed. The residue was purified by chromatography on silica using ethylacetate/petrolether (50/50) to afford the title compound as a pale yellow oil (0.93 g, 65%).

$^1$H-NMR (400 MHz, $CDCl_3$): d=1.52 (s, 9H), 2.90 (t, 3H), 3.15 (t, 3H), 3.40 (s, 3H), 4.68 (t, 2H), 6.90 (t, 1H), 7.53-7.60 (m, 2H)

Step E

The title compound from Step D above (0.93 g, 2.8 mmol) was dissolved in N,N'-dimethylacetamide (10 mL) and sodium azide (0.91 g, 14 mmol) was added. The mixture was heated in a sand bath at ~75° C. for 16 h. The mixture was diluted with ethylacetate (80 mL) and 10% citric acid solution (30 mL). The organic phase was separated, washed with saturated sodium bicarbonate (25 mL) and brine (25 mL). The organic phase was dried over $Na_2SO_4$, filtered and the solvents were removed. The residue was purified by chromatography on silica using ethylacetate/petrolether (20/80) to afford the title compound as a pale yellow oil (0.69 g, 89%).

$^1$H-NMR (400 MHz, $CDCl_3$): d=1.55 (s, 9H), 3.00 (t, 3H), 3.40 (s, 3H), 3.71 (t, 2H), 6.88-6.92 (m, 1H), 7.53-7.60 (m, 2H)

Step F

The title compound from Step E above (0.69 g, 2.5 mmol) was dissolved in tetrahydrofuran (20 mL) and triphenylphosphine (0.79 g, 3 mmol) was added. The mixture was stirred at room temperature for 18 h and water (10 mL) was added. Stirring was continued for 5 h and the solvents were removed. The residue was purified by chromatography on silica using dichloromethane/methanol (95/5) to elute unpolar by-products, followed by dichloromethane/methanol (1/1) containing 7 M ammonia in methanol (10 mL per 500 mL) to afford the title compound as pale yellow oil (0.52 g, 82%).

$^1$H-NMR (400 MHz, $CDCl_3$): d=1.52 (s, 9H), 1.68 (br-s, 2H), 2.88 (t, 2H), 3.11 (t, 2H), 3.40 (s, 3H), 6.88 (d, 1H), 7.50 (d, 1H), 7.53 (t, 1H)

Step G

A solution of LDA was prepared by adding a 1.6 M solution of n-butyllithium in hexane (51 mL, 81.2 mmol) at 0° C. to a stirred solution of N,N'-diisopropylamine (13.5 mL, 97.4 mmol) in tetrahydrofuran (60 mL). The mixture was stirred at 0° C. for 15 min and then added at −78° C. to a solution of commercially available 2-bromo-6-methylpyridine (5 g, 29.1 mmol) in tetrahydrofuran (90 mL). The mixture was stirred at −78° C. for 25 minutes and then N,N'-dimethylformamide (7.9 mL, 107 mmol) was added. After 30 minutes at −78° C., methanol (80 mL) and acetic acid (6.1 mL, 132 mmol) were added. Then sodium borohydride (1.1 g, 28 mmol) was added at −78° C. and the mixture was stirred overnight and allowed to reach room temperature. The reaction mixture was diluted with ethylacetate (150 mL) and washed with a 10% citric acid solution (80 mL) and brine (80 mL). The organic phase was separated and the aqueous phase extracted with ethylacetate (2×150 mL). The combined organic phase was dried over $Na_2SO_4$, filtered and the solvents were removed. The residue was purified by chromatography on silica using dichloromethane/acetone (95/5) to afford the title compound as pale yellow oil (5 g, 85%).

$^1$H-NMR (400 MHz, $CDCl_3$): d=3.01 (t, 2H), 3.09 (t, 1H), 4.02 (q, 2H), 7.16 (d, 1H), 7.34 (d, 1H), 7.43 (t, 1H)

Step H

The title compound from Step G above (5 g, 24.75 mmol) was dissolved in N,N'-dimethylformamide (100 mL) and imidazole (4.84 g, 74.25 mmol) was added. After the addition of chlorotriisopropylsilane (7.92 mL, 37.1 mmol), the mixture was stirred at room temperature for 16 h. The reaction mixture was diluted with diethylether (300 mL) and washed with a 10% citric acid solution (3×40 mL) and brine (100 mL). The organic phase was separated, dried over $Na_2SO_4$, filtered and the solvents were removed. The residue was purified by chromatography on silica using ethylacetate/n-heptane (5/95) to afford the title compound as a colorless liquid (7.36 g, 83%).

$^1$H-NMR (400 MHz, CDCl$_3$): d=0.92-1.13 (m, 21H), 3.00 (t, 2H), 4.08 (q, 2H), 7.22 (d, 1H), 7.33 (d, 1H), 7.45 (t, 1H)

Step I

The title compound from Step H above (0.21 g, 0.6 mmol) and the title compound from Step F above (0.16 g, 0.63 mmol) were dissolved in toluene (11 mL) and treated with 2,2-bis-(diphenylphosphino)-1,1-naphthalene (0.082 g, 0.12 mmol) and sodium tert-butylate (0.16 g, 1.63 mmol). The reaction mixture was then degassed by bubbling argon through the reaction mixture followed by the addition of tris(dibenzylideneacetone)dipalladium chloroform complex (0.054 g, 0.06 mmol). The reaction vessel was sealed and the mixture was heated at ~80 to 85° C. in a sand bath for 45 minutes. The reaction mixture was diluted with ethyl acetate (60 mL) and water (20 mL). The organic phase was washed with saturated sodium bicarbonate (20 mL) and brine (20 mL). The organic phase was separated, dried over Na$_2$SO$_4$, filtered and the solvents were removed. The residue was purified by chromatography on silica using dichloromethane/acetone (95/5) to elute unpolar impurities, followed by ethylacetate/n-heptane (20/80) to afford the title compound as a pale yellow oil (0.26 g, 78%).

$^1$H-NMR (400 MHz, CDCl$_3$): d=0.92-1.13 (m, 21H), 1.52 (s, 9H), 2.83 (t, 2H), 3.03 (t, 2H), 3.42 (s, 3H), 3.66 (q, 2H), 4.02 (t, 2H), 4.95 (br-s, 1H), 6.26 (d, 1H), 6.49 (d, 1H), 6.88 (dd, 1H), 7.31 (t, 1H), 7.54-7.57 (m, 2H)

Step J

The title compound from Step I above (0.26 g, 0.53 mmol) was dissolved in tetrahydrofuran (1 mL) and di-tert-butyl dicarbonate (0.17 g, 0.84 mmol) was added. After the addition of 4-dimethylaminopyridine (0.006 g, 0.05 mmol), the mixture was heated in a sand bath at ~65° C. overnight. Another batch of di-tert-butyl dicarbonate (0.17 g, 0.84 mmol) and 4-dimethylaminopyridine (0.006 g, 0.05 mmol) was added and heating was continued at ~75° C. for 12 h. The remaining solvent was then removed and after the addition of di-tert-butyl dicarbonate (0.17 g, 0.84 mmol) heating at 18 75° C. was continued overnight. The residue was purified by chromatography on silica using n-heptane to elute excess di-tert-butyl dicarbonate, followed by ethylacetate/n-heptane (10/90) to afford the title compound as colorless oil (0.27 g, 80%).

$^1$H-NMR (400 MHz, CDCl$_3$): d=0.92-1.13 (m, 21H), 1.47 (s, 9H), 1.52 (s, 9H), 2.97 (t, 2H), 3.09 8t, 2H), 3.38 (s, 3H), 4.06 (t, 2H), 4.31 (t, 2H), 6.83-6.87 (m, 1H), 6.93 (d, 1H), 7.35 (d, 1H), 7.47-7.52 (m, 3H)

Step K

The title compound from Step J above (0.27 g, 0.428 mmol) was dissolved in acetonitrile (5 mL) and a 1 M solution of tetrabutylammonium fluoride (2.14 mL, 2.14 mmol) in tetrahydrofuran was added. The mixture was stirred at room temperature over the weekend and the solvents were removed. The residue was purified by chromatography on silica using ethylacetate/n-heptane (60/40) to afford the title compound as a colorless oil (0.19 g, 92%).

$^1$H-NMR (400 MHz, CDCl$_3$): d=1.51 (s, 9H), 1.53 (s, 9H), 2.98 (t, 2H), 3.07 (t, 2H), 3.3.5 (s, 3H), 3.78 (br-s, 1H), 3.98-4.04 (m, 2H), 4.28 (t, 2H), 6.86-6.88 (m, 2H), 7.39 (d, 1H), 7.45-7.57 (m, 3H)

Step L

The title compound from Step K above (0.19 g, 0.396 mmol) was dissolved in dichloromethane (2 mL) and triethylamine (0.12 mL, 0.9 mmol) was added. After the addition of methanesulfonyl chloride (0.06 mL, 0.8 mmol), the mixture was stirred at room temperature for 1 h. The mixture was concentrated and the residue was purified by chromatography on silica using ethylacetate/n-heptane (50/50) to afford the title compound as a pale yellow oil (0.2 g, 90%).

$^1$H-NMR (400 MHz, CDCl$_3$): d=1.51 (s, 9H), 1.53 (s, 9H), 2.90 (s, 3H), 3.09 (t, 2H), 3.15 (t, 2H), 3.37 (s, 3H), 4.31 (t, 2H), 4.68 (t, 2H), 6.86 (d, 1H), 6.91 (d, 1H), 7.47-7.59 (m, 4H)

Step M

The title compound from Step L above (0.2 g, 0.36 mmol) was dissolved in N,N'-dimethylacetamide (1.3 mL) and sodium azide (0.12 g, 1.8 mmol) was added. The mixture was heated at ~75° C. in a sand bath overnight. The mixture was diluted with ethylacetate (25 mL) and 10% citric acid (10 mL). The organic phase was separated, washed with brine (10 mL), dried over Na$_2$SO$_4$, filtered and the solvents were removed. The residue was purified by chromatography on silica using ethylacetate/n-heptane (20/80) to afford the title compound as a colorless oil (0.16 g, 92%).

$^1$H-NMR (400 MHz, CDCl$_3$): d=1.51 (s, 9H), 1.53 (s, 9H), 3.01 (t, 2H), 3.10 (t, 2H), 3.37 (s, 3H), 3.73 (t, 2H), 4.32 (t, 2H), 6.84 (dd, 1H), 6.90 (d, 1H), 7.46-7.55 (m, 4H)

Step N

The title compound from Step M above (0.16 g, 0.33 mmol) was dissolved in tetrahydrofuran (4 mL) and triphenylphosphine (0.1 g, 0.39 mmol) was added. The reaction mixture was stirred at room temperature for 30 h and then water (2 mL) was added. Stirring was continued for 14 h and the solvents were removed in vacuo. The residue was purified by chromatography on silica using dichloromethane/methanol (95/5) followed by dichloromethane/methanol (1/1, containing 10 mL 7 M ammonia in methanol per 500 mL) to afford the title compound as a colorless oil (0.13 g, 85%).

$^1$H-NMR (400 MHz, CDCl$_3$): d=1.51 (s, 9H), 1.53 (s, 9H), 2.90 (t, 1H), 3.08 (t, 2H), 3.14 (t, 2H), 3.37 8s, 3H), 4.32 (t, 2H), 6.85-6.89 (m, 2H), 7.39 (d, 1H), 7.44-7.55 (m, 3H)

Step O

The title compound from Step N above (0.13 g, 0.28 mmol) and 2-bromopyridine (0.043 g, 0.27 mmol) were dissolved in toluene (4.8 mL) and treated with 2,2-bis-(diphenylphosphino)-1,1-naphthalene (0.034 g, 0.059 mmol) and sodium tert-butylate (0.082 g, 0.853 mmol). The reaction mixture was then degassed by bubbling argon through the reaction mixture followed by the addition of tris(dibenzylideneacetone)dipalladium chloroform complex (0.025 g, 0.027 mmol). The reaction vessel was sealed and the mixture was heated at ~80 to 85° C. in a sand bath for 45 minutes. The reaction mixture was diluted with ethyl acetate (30 mL) and water (10 mL). The organic phase was washed with saturated sodium bicarbonate (10 mL) and brine (10 mL). The organic phase was separated, dried over Na$_2$SO$_4$, filtered and the solvents were removed. The residue was purified by chromatography on silica using dichloromethane/acetone (95/5) to elute unpolar impurities, followed by ethylacetate/n-heptane (60/40) to elute the mixture of reaction products. The less polar product was separated from the more polar product by preparative TLC plates (Analtech, 0.5 mm) using ethylacetate/n-heptane (70/30) as a mobile phase to afford the title compounds.

less polar: (0.029 g, pale yellow oil, 16%)

$^1$H-NMR (400 MHz, CDCl$_3$): d=1.49 (s, 9H), 1.51 (s, 9H), 3.19 (t, 2H), 3.32 (s, 3H), 4.30 (t, 2H), 4.59 (t, 2H), 6.81-6.88 (m, 4H), 7.07-7.09 (m, 2H), 7.34 (d, 1H), 7.43-7.51 (m, 5H), 8.30-8.32 (m, 2H)

more polar: (0.035 g, pale yellow oil, 22%)

$^1$H-NMR (400 MHz, CDCl$_3$): d=1.50 (s, 18H), 3.03 (t, 2H), 3.10 (t, 2H), 3.32 (s, 3H), 3.68-3.74 (m, 2H), 4.32 (t, 2H), 5.00 (br-s, 1H), 6.34 (d, 1H), 6.51-656 (m, 1H), 6.82-6.89 (m, 2H), 7.31-7.53 (m, 5 H), 8.08 (br-s, 1H)

Step P

The more polar product from Step 0 above (0.035 g, 0.06 mmol) was dissolved in chloroform (1.1 mL) and treated with a 2 M solution of hydrogen chloride in diethylether (1.1 mL). The reaction mixture was stirred at room temperature overnight and the solvents were removed using a syringe. The solid material was dissolved in water (2 mL) and filtered through a 0.2 μm filter cartridge. The filtrate was collected and the solvent evaporated to afford the title compound as an orange glass (0.026 g, 90%).

$^1$H-NMR (400 MHz, D$_2$O): d=2.92 (s, 3H), 3.03-3.09 (m, 4H), 3.68-3.76 (m, 4H), 6.63 (d, 1H), 6.73 8d, 1H), 6.79-6.87 (m, 3H), 6.92 (d, 1H), 7.68-7.85 (m, 4H) (MS (ESI); m/z=349.52 (MH$^+$)

Step Q

The less polar product from Step O above (0.029 g, 0.046 mmol) was dissolved in chloroform (0.8 mL) and treated with a 2 M solution of hydrogen chloride in diethylether (0.8 mL). The reaction mixture was stirred at room temperature overnight and the solvents were removed using a syringe. The solid material was dissolved in water (2 mL) and filtered through a 0.2 μm filter cartridge. The filtrate was collected and the solvent was evaporated to afford the title compound as an orange glass (0.024 g, 97%).

$^1$H-NMR (400 MHz, D$_2$O): d=2.91 (s, 3H), 3.00 (t, 2H), 3.21 (t, 2H), 3.63 (t, 2H), 4.49 (t, 2H), 6.60-6.64 (m, 2H), 6.70 (d, 1H), 6.81 (d, 1H), 7.26 (t, 2H), 7.38 (d, 2H), 7.62 (t, 1H), 7.70 (t, 1H), 7.99-8.04 (m, 2H), 8.13 (d, 2H)

MS (ESI); m/z=426.42 (MH$^+$)

Preparation Example 2 (Compound 1)

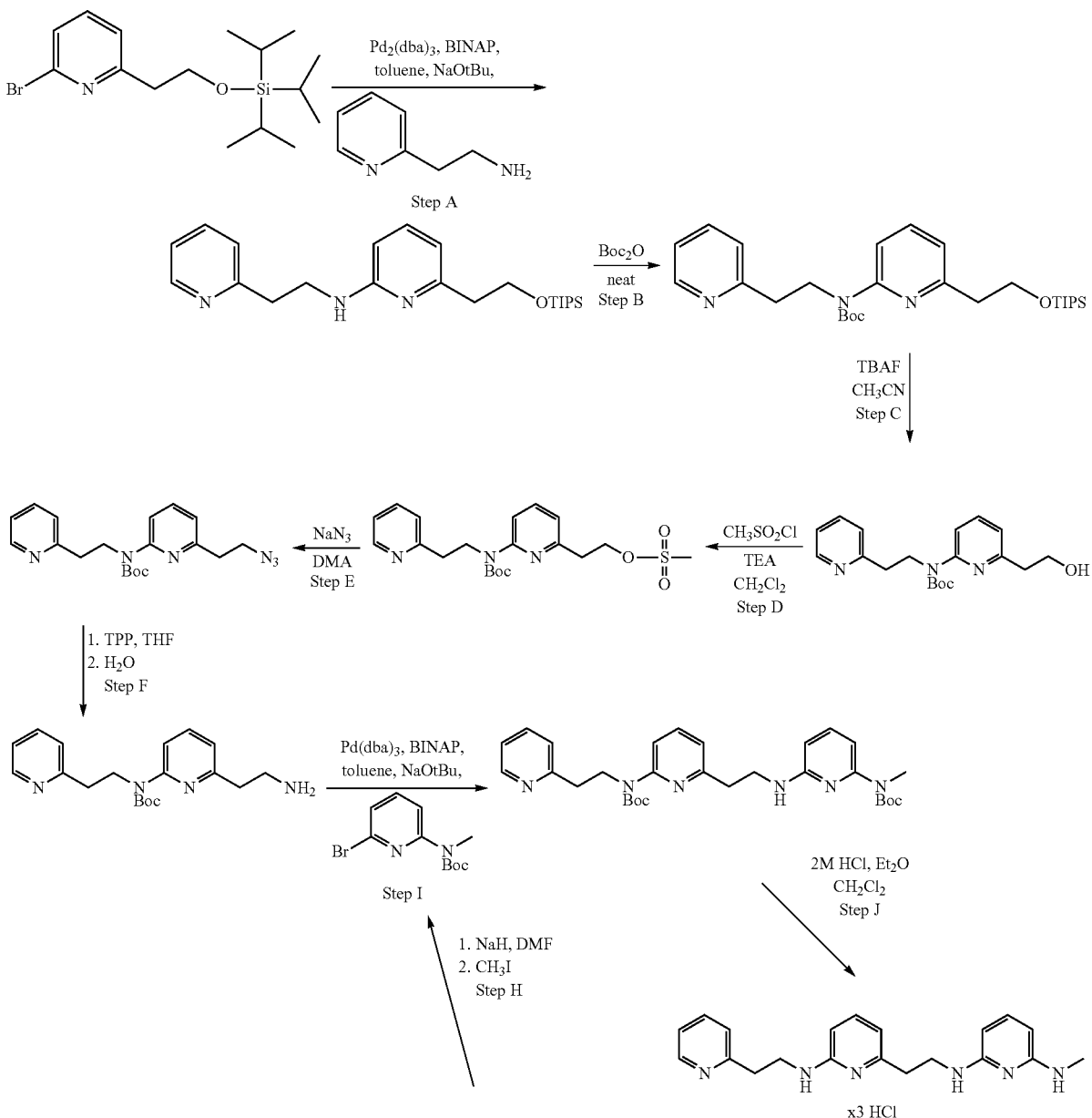

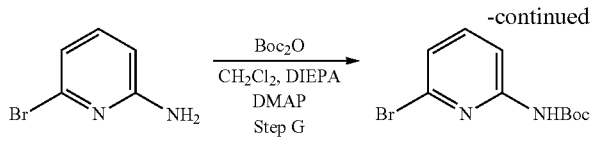

Step A

The title compound from Example 1 Step H (0.9 g, 2.51 mmol) and commercially available 2(2-aminoethyl)-pyridine (0.34 g, 2.78 mmol) were dissolved in toluene (45 mL) and treated with 2,2-bis-(diphenylphosphino)-1,1-naphthalene (0.33 g, 0.48 mmol) and sodium tert-butylate (0.63 g, 6.6 mmol). The reaction mixture was then degassed by bubbling argon through the reaction mixture followed by the addition of tris(dibenzylidene-acetone)dipalladium (0.22 g, 0.024 mmol). The reaction vessel was sealed and the mixture was heated at ~80 to 85° C. in a sand bath for 45 minutes. The reaction mixture was diluted with ethyl acetate (150 mL), water (30 mL) and brine (30 mL). The organic phase was separated, dried over $Na_2SO_4$, filtered and the solvents were removed. The residue was purified by chromatography on silica using dichloromethane/acetone (95/5) to elute unpolar impurities, followed by ethylacetate to afford the title compound as a dark yellow oil. Three additional runs yielded a total of 3.4 g (84%).

$^1$H-NMR (400 MHz, $CDCl_3$): d=0.98-1.10 (m, 21H), 2.85 (t, 2H), 3.10 (t, 2H), 3.68 (q, 2H), 4.03 (t, 2H), 4.81 (br-s, 1H), 6.24 (d, 1H), 6.50 (d, 1H), 7.13-7.18 (m, 2H), 7.32 (t, 1H), 7.60 (t, 1H), 8.58 (d, 1H)

Step B

The title compound from Step A above (1.7 g, 4.26 mmol) was dissolved in dichoromethane (30 mL) and di-tert-butyl dicarbonate (4.75 g, 21.3 mmol) was added. The solvent was removed and the oily residue was heated in a sand bath at ~75° C. for 18 to 36 h until TLC indicated the consumption of the starting material. The mixture was then purified by chromatography on silica using ethylacetate/n-heptane (10/90) to remove excess di-tert-butyl dicarbonate, followed by ethylacetate/n-heptane (30/70) to afford the title compound as a pale yellow oil. Two runs yielded a total of 3.6 g (86%).

$^1$H-NMR (400 MHz, $CDCl_3$): d=0.98-1.10 (m, 21H), 1.42 (s, 9H), 2.92 (t, 2H), 3.11 (t, 2H), 4.01 (t, 2H), 4.30 (t, 2H), 6.90 (d, 1H), 7.07-7.10 (m, 1H), 7.12 (d, 1H), 7.36 (d, 1H), 7.46-7.56 (m, 2H), 8.49 (d, 1H)

Step C

The title compound from Step B above (3.9 g, 7.81 mmol) was dissolved in acetonitrile (100 mL) and treated with 1 M solution of tetrabutylammonium fluoride (30 mL, 30 mmol) in tetrahydrofuran. The mixture was stirred at room temperature overnight and the solvents were removed. The residue was purified by chromatography on silica using ethylacetate to afford the title compound as a pale yellow oil (2.57 g, 95%).

$^1$H-NMR (400 MHz, $CDCl_3$): d=1.49 (s, 9H), 2.98 (t, 2H), 3.11 (t, 2H), 4.04 (t, 2H), 4.30 (t, 2H), 6.85 (d, 1H), 7.06-7.10 (m, 1H), 7.16 (d, 1H), 7.38 (d, 1H), 7.48-7.57 (m, 2H), 8.46 (d, 1H)

Step D

The title compound from Step C above (2.57 g, 7.49 mmol) was dissolved in dichloromethane (45 mL) and triethylamine (2.33 mL, 16.9 mmol) was added. The mixture was cooled to 0° C. and methanesulfonylchloride (1.17 mL, 15 mmol) was added. After the addition was completed, the mixture was stirred at 0° C. for 5 min and then at room temperature for 1 h. The solvents were evaporated and the residue was purified by chromatography on silica using ethylacetate to afford the title compound as a pale yellow oil (3.1 g, 98%).

$^1$H-NMR (400 MHz, $CDCl_3$): d=1.49 (s, 9H), 2.91 (s, 3H), 3.11-3.17 (m, 4H), 4.30 (t, 2H), 4.66 (t, 2H), 6.89 (d, 1H), 7.08-7.11 (m, 1H), 7.15 (d, 1H), 7.46 (d, 1H), 7.53 (t, 1H), 7.56 (dt, 1H), 8.49 (d, 1H)

Step E

The title compound from Step D above (1.57 g, 3.73 mmol) was dissolved in N,N'-dimethylacetamide (17.5 mL) and sodium azide (1.22 g, 18.6 mmol) was added. The mixture was heated at ~75° C. in a sand bath overnight. The mixture was diluted with ethylacetate (150 mL) and water (40 mL). The organic phase was separated, washed with brine (40 mL), dried over $Na_2SO_4$, filtered and the solvents were removed. The residue was purified by chromatography on silica using ethylacetate/n-heptane (60/40) to afford the title compound as a colorless oil. Two runs yielded a total of 2.4 g, 87%.

$^1$H-NMR (400 MHz, $CDCl_3$): d=1.43 (s, 9H), 2.97 (t, 2H), 3.12 (t, 2H), 3.69 (t, 2H), 4.31 (t, 2H), 6.87 (d, 1H), 7.07-7.10 (m, 1H), 7.12 (d, 1H), 7.46 8d, 1H), 7.51-7.58 (m, 2H), 8.50 (d, 1H)

Step F

The title compound from Step E above (2.4 g, 6.52 mmol) was dissolved in tetrahydrofuran (60 mL) and triphenylphosphine (2.15 g, 8.17 mmol) was added. The reaction mixture was stirred at room temperature for 48 h and then water (30 mL) was added. Stirring was continued for 16 h and the solvents were removed in vacuo. The residue was purified by chromatography on silica using dichloromethane/methanol (95/5) to remove unpolar by-products, followed by dichloromethane/methanol (1/1, containing 10 mL 7 M ammonia in methanol per 500 mL) to afford the title compound as a pale yellow oil (2.1 g, 95%).

$^1$H-NMR (400 MHz, $CDCl_3$): d=1.43 (s, 9H), 2.83 (t, 2H), 3.06-3.14 (m, 4H), 4.31 (t, 2H), 6.84 (d, 1H), 7.05-7.09 (m, 1H), 7.12 (d, 1H), 7.37 (d, 1H), 7.48 (t, 1H), 7.52 (dt, 1H), 8.47 (d, 1H)

Step G

Commercially available 2-amino-6-bromo-pyridine (4.25 g, 24.6 mmol) was dissolved in dichloromethane (50 mL) and N,N'-diisopropylethylamine (5.25 mL, 30.7 mmol) and 4-dimethylaminopyridine (0.15 g, 1.23 mmol) was added. After the addition of a solution of di-tert-butyl dicarbonate (5.9 g, 27 mmol) in dichloromethane (15 mL), the mixture was stirred at room temperature overnight. The mixture was diluted with dichloromethane (100 mL) and washed with 10% citric acid (50 mL) and brine (50 mL). The organic phase was separated, dried over $Na_2SO_4$, filtered and the solvents were removed. The residue was purified by chromatography on silica using ethylacetate/n-heptane (5/95) to afford the title compound as a white solid (2.15 g, 32%). Washing the column with ethylacetate/n-heptane (10/90) afforded the corresponding bis-Boc-derivative as a white solid (1.95 g, 21%).

$^1$H-NMR (400 MHz, $CDCl_3$): d=1.52 (s, 9H), 7.13 (d, 1H), 7.27 (br-s, 1H), 7.51 (t, 1H), 7.90 (d, 1H)

Bis-Boc derivative:

$^1$H-NMR (400 MHz, CDCl$_3$): d=1.48 (s, 18H), 7.27 (d, 1H), 7.40 (d, 1H), 7.60 (t, 1H)

Step H

Sodium hydride (0.18 g, 7.38 mmol) was suspended in N,N'-dimethylacetamide (10 mL) and the mixture was cooled to 0° C. At 0° C. a solution of the title compound from Step G above (1.66 g, 6.1 mmol) in N,N'-dimethylacetamide (5 mL) was added over a period of 5 minutes. After the addition was completed, the reaction mixture was stirred at 0° C. for 5 minutes and then 60 minutes at room temperature. Then methyliodide (0.5 mL, 8.12 mmol) was added in one portion and the reaction mixture was stirred at room temperature overnight. The reaction mixture was diluted with ethyl acetate (100 mL) and washed with 10% citric acid solution (30 mL), saturated sodium bicarbonate (30 mL) and brine (30 mL). The organic phase was separated, dried over Na$_2$SO$_4$, filtered and the solvents were removed. The residue was purified by chromatography on silica using ethyl acetate/n-heptane (5/95) to afford the desired compound as a colorless liquid (1.54 g, 90%).

$^1$H-NMR (400 MHz, CDCl$_3$): d=1.52 (s, 9H), 3.40 (s, 3H), 7.17 (d, 1H), 7.47 (t, 1H), 7.74 (d, 1H)

Step I

The title compounds from Step F (0.525 g, 1.54 mmol) and Step H (0.423 g, 1.53 mmol) above were dissolved in toluene (24 mL) and treated with 2,2-bis-(diphenylphosphino)-1,1-naphthalene (0.186 g, 0.3 mmol) and sodium tert-butylate (0.383 g, 3.98 mmol). The reaction mixture was then degassed by bubbling argon through the reaction mixture followed by the addition of tris(dibenzylideneacetone) dipalladium (0.133 g, 0.15 mmol).

The reaction vessel was sealed and the mixture was heated at ~110° C. in a sand bath for 45 minutes. The reaction mixture was diluted with ethyl acetate (100 mL), water (20 mL) and brine (20 mL). The organic phase was separated, dried over Na$_2$SO$_4$, filtered and the solvents were removed. The residue was purified by chromatography on silica using dichloromethane/acetone (95/5) to elute unpolar impurities, followed by ethylacetate/n-heptane (60/40) to elute the desired compound. The crude title compound from four runs was further purified by chromatography on silica using ethylacetate/n-heptane (60/40) to afford the title compound as a pale orange oil (3 g, 89%).

$^1$H-NMR (400 MHz, CDCl$_3$): d=1.50 (s, 9H), 1.52 (s, 9H), 3.02 (t, 2H), 3.18 (t, 2H), 3.32 (s, 3H), 3.70-3.74 (m, 2H), 4.38 (t, 2H), 5.20 (br-s, 1H), 6.13 (d, 1H), 6.83-6.88 (m, 2H), 7-06-7.09 (m, 1H), 7.13 (d, 1H), 7.31 (t, 1H), 7.40 (d, 1H), 7.50 (t, 1H), 7.53 (dt, 1H), 8.48 (d, 1H)

Step J

The title compound from Step I above (3 g, 5.47 mmol) was dissolved in dichloromethane (50 mL) and treated with a 2 M solution of hydrogen chloride in diethylether (50 mL). The reaction mixture was stirred at room temperature overnight and the solvents were removed using a syringe. The residue was dissolved in water (30 mL) and filtered through a 0.2 μm filter cartridge (10 mL per cartridge). The three cartridges were washed with water (5 mL). The combined filtrate was collected and the solvent was evaporated using a freeze-dryer to afford the title compound as a pale orange foam (2.2 g, 88%).

$^1$H-NMR (400 MHz, D$_2$O): d=2.79 (s, 3H), 3.02 (t, 2H), 3.33 (t, 2H), 3.57 (t, 2H), 3.81 (t, 2H), 5.81 (d, 1H), 5.92 (d, 1H), 6.71 (d, 1H), 6.81 (d, 1H), 7.50 (t, 1H), 7.78 (t, 1H), 7.83-7.91 (m, 2H), 8.42 (t, 1H), 8.59 (d, 1H)

MS (ESI); m/z=349.42 (MH$^+$)

Preparation Example 3 (Alternative Synthesis Scheme for Compound 1)

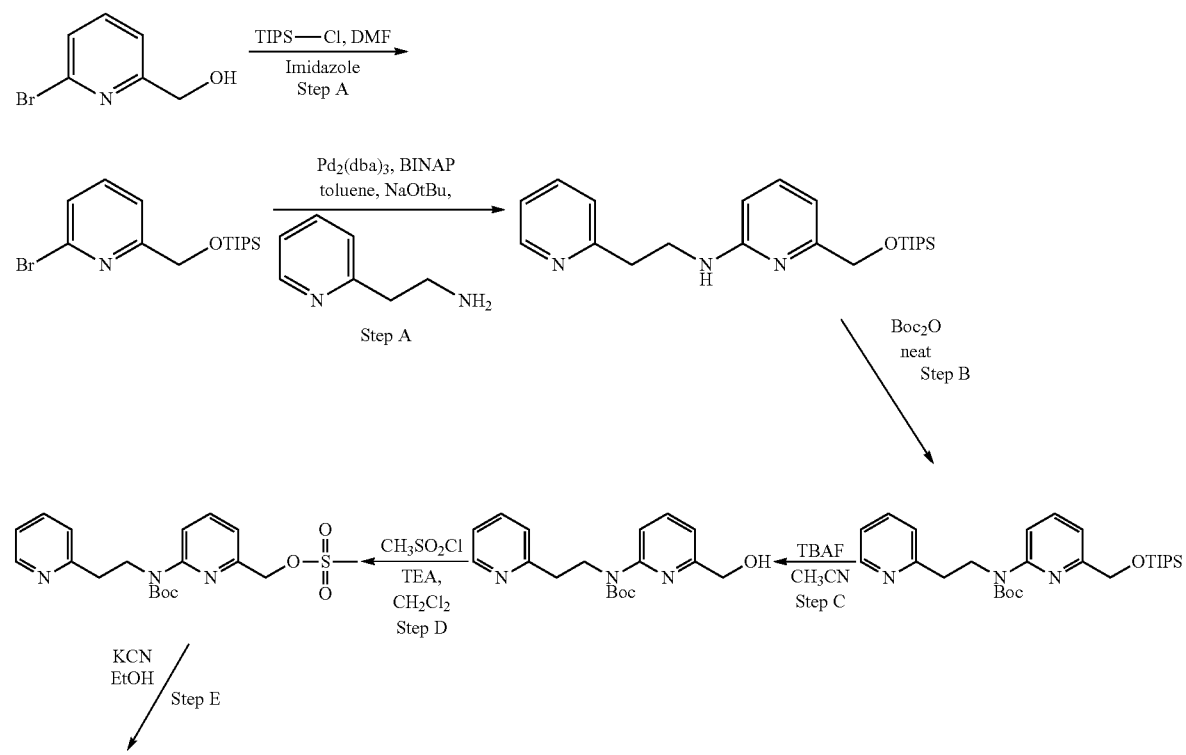

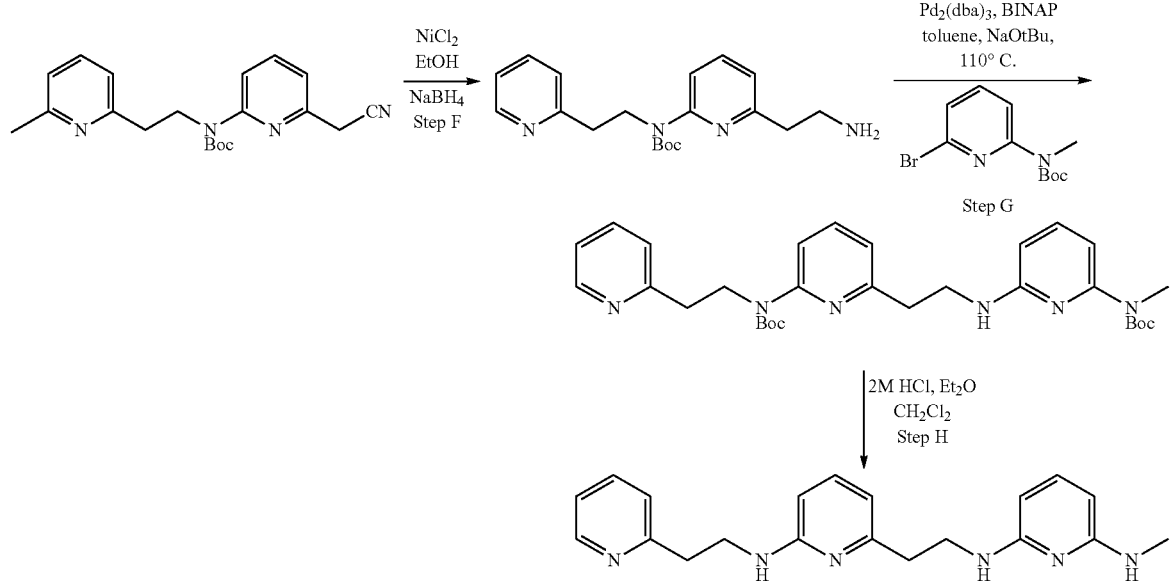

Step A

Commercially available (6-bromopyridin-2-yl)-methanol (1 g, 5.3 mmol) was dissolved in N,N'-dimethylformamide (20 mL) and imidazole (0.97 g, 14.85 mmol) was added. After the addition of triisopropylsilyl chloride (1.58 mL, 7.42 mmol), the mixture was stirred at room temperature over the weekend. The mixture was diluted with diethylether (80 mL) and washed with 10% citric acid solution (25 mL) and brine (25 mL). The organic phase was separated, dried over $Na_2SO_4$, filtered and the solvents were removed. The residue was purified by chromatography on silica using ethylacetate/n-heptane (5/95). Fractions containing the protected alcohol were collected and the solvents were evaporated to yield a colorless liquid (1.7 g, 92%). The protected alcohol (0.85 g, 2.47 mmol) and commercially available 2-(2-aminoethyl)-pyridine (0.35 g, 2.78 mmol) were dissolved in toluene (45 mL) and treated with 2,2-bis-(diphenylphosphino)-1,1-naphthalene (0.33 g, 0.48 mmol) and sodium tert-butylate (0.63 g, 6.625 mmol). The reaction mixture was then degassed by bubbling argon through the reaction mixture followed by the addition of tris(dibenzylideneacetone)dipalladium (0.22 g, 0.24 mmol). The reaction vessel was sealed and the mixture was heated at ~80 to 85° C. in a sand bath for 45 minutes. The reaction mixture was diluted with ethyl acetate (1000 mL), water (20 mL) and brine (20 mL). The organic phase was separated, dried over $Na_2SO_4$, filtered and the solvents were removed. The residue was purified by chromatography on silica using dichloromethane/acetone (95/5) to elute unpolar impurities, followed by ethylacetate to afford the title compound as a brown oil. Two runs yielded a total of 1.6 g (84%).

$^1$H-NMR (400 MHz, $CDCl_3$): d=1.06-1.08 (m, 18 H), 1.13-1.24 (m, 3H), 3.07 (t, 2H), 3.64-3.69 (m, 2H), 4.72 (s, 2H), 4.81 (br-s, 1H), 6.28 (d, 1H), 6.86 (d, 1H), 7.12-7.18 (m, 2H), 7.43 (t, 1H), 7.59 (dt, 1H), 8.56 (d, 1H)

Step B

The title compound from Step A above (1.6 g, 4.15 mmol) was dissolved in dichoromethane (30 mL) and di-tert-butyl dicarbonate (4.75 g, 21.3 mmol) was added. The solvent was removed and the oily residue was heated in a sand bath at ~75° C. for 24 h until TLC indicated the consumption of the starting material. The mixture was then purified by chromatography on silica using ethylacetate/n-heptane (10/90) to remove excess di-tert-butyl dicarbonate, followed by ethylacetate/n-heptane (30/70) to afford the title compound as a pale yellow oil (1.75 g, 86%).

$^1$H-NMR (400 MHz, $CDCl_3$): d=1.06-1.08 (m, 18 H), 1.13-1.24 (m, 3H), 1.44 (s, 9H), 3.10 (t, 2H), 4.31 (t, 2H), 4.80 (s, 2H), 7.05-7.08 (m, 1H), 7.12 (d, 1H), 7.25-7.33 (m, 2H), 7.53 (dt, 1H), 7.60 (t, 1H), 8.48 (d, 1H)

Step C

The title compound from Step B above (1.75 g, 3.6 mmol) was dissolved in acetonitrile (45 mL) and treated with 1 M solution of tetrabutylammonium fluoride (13 mL, 13 mmol) in tetrahydrofuran. The mixture was stirred at room temperature overnight and the solvents were removed. The residue was purified by chromatography on silica using ethylacetate to afford the title compound as a pale orange oil (1.16 g, 97%).

$^1$H-NMR (400 MHz, $CDCl_3$): d=1.52 (s, 9H), 3.18 (t, 2H), 4.31 (t, 2H), 4.40-4.52 (br-s, 1H), 4.70 (s, 2H), 6.87-6.90 (m, 1H), 7.08-7.16 (m, 2H), 7.54-7.62 (m, 3H), 8.55 (d, 1H)

Step D

The title compound from Step C above (0.33 g, 1 mmol) was dissolved in dichloromethane (5 mL) and triethylamine (0.28 mL, 2 mmol) was added. The mixture was cooled to 0° C. and methanesulfonylchloride (0.13 mL, 1.7 mmol) was added. After the addition was completed, the mixture was stirred at 0° C. for 5 min and then at room temperature for 1 h. The solvents were evaporated and the residue was purified by chromatography on silica using ethylacetate/n-heptane (60/40) to afford the title compound as a pale yellow oil (0.31 g, 75%).

$^1$H-NMR (400 MHz, $CDCl_3$): d=1.46 (s, 9H), 3.07 (s, 3H), 3.11 (t, 2H), 4.33 (t, 2H), 5.22 (s, 2H), 7.07-7.16 (m, 3H), 7.53-7.66 (m, 3H), 8.48 (d, 1H)

Step E

The title compound from Step D above (0.3 g, 0.75 mmol) was dissolved in ethanol (17.5 mL) and potassium cyanide (0.24 g, 3.75 mmol) was added. The mixture was heated at ~85° C. in a sand bath for 1 h. The solvent was removed and the residue was dissolved with ethylacetate (30 mL) and water (5 mL). The organic phase was separated, washed with brine (5 mL), dried over Na$_2$SO$_4$, filtered and the solvents were removed. The residue was purified by chromatography on silica using ethylacetate/n-heptane (60/40) to afford the title compound as a pale yellow oil (0.118 g, 46%).

$^1$H-NMR (400 MHz, CDCl$_3$): d=1.47 (s, 9H), 3.17 (t, 2H), 3.83 (s, 2H), 4.34 (t, 2H), 7.04-7.11 (m, 2H), 7.18 (d, 1H), 7.56 (dt, 1H), 7.60-7.63 (m, 2H), 8.49 (d, 1H)

Step F

The title compound from Step E above (0.118 g, 0.35 mmol) was dissolved in dry ethanol (1.2 mL) and nickel (II)-chloride was added (0.045 g, 0.35 mmol). To the reaction mixture was added sodium borohydride (0.04 g, 1.05 mmol) in portions (exothermic). After the addition was completed, the black reaction mixture was stirred at room temperature for 2 h until all starting material was consumed. The black reaction mixture was filtered through a pad of Celite and the pad was washed with ethanol (25 mL). The pale yellow filtrate was evaporated and the residue was purified by chromatography on silica using dichloromethane/methanol (9/1) to remove unpolar by-products, followed by dichloromethane/methanol (1/1, containing 10 mL 7 M ammonia in methanol per 500 mL) to afford the title compound as a yellow oil (0.084 g, 70%).

$^1$H-NMR (400 MHz, CDCl$_3$): d=1.51 (s, 9H), 3.03 (t, 2H), 3.16 (t, 2H), 3.30 (t, 2H), 3.12-3.48 (br-s, 2H), 4.32 (t, 2H), 6.88 (d, 1H), 7.07-7.12 (m, 1H), 7.17 (d, 1H), 7.42 (d, 1H), 7.53 (t, 1H), 7.58 (dt, 1H). 8.57 (d, 1H)

MS (ESI); m/z=342.98 (MH$^+$)

Step G

The title compounds from Step F above (0.084 g, 0.245 mmol) and from Preparative Example 2 Step I (0.068 g, 0.245 mmol) above were dissolved in toluene (4 mL) and treated with 2,2-bis-(diphenylphosphino)-1,1-naphthalene (0.03 g, 0.048 mmol) and sodium tert-butylate (0.062 g, 0.64 mmol). The reaction mixture was then degassed by bubbling argon through the reaction mixture followed by the addition of tris(dibenzylideneacetone)dipalladium (0.021 g, 0.024 mmol). The reaction vessel was sealed and the mixture was heated at ~110° C. in a sand bath for 45 minutes. The reaction mixture was diluted with ethyl acetate (30 mL), water (5 mL) and brine (5 mL). The organic phase was separated, dried over Na$_2$SO$_4$, filtered and the solvents were removed. The residue was purified by chromatography on silica using dichloromethane/acetone (95/5) to elute unpolar impurities, followed by ethylacetate to elute the desired compound. The crude title compound was further purified by PREP-TLC using ethylacetate/n-heptane (60/40) to afford the title compound as a pale yellow oil (0.04 g, 29%).

$^1$H-NMR (400 MHz, CDCl$_3$): d=1.48 (s, 9H), 1.50 (s, 9H), 3.02 (t, 2H), 3.16 (t, 2H), 3.31 (s, 3H), 3.70 (t, 2H), 4.38 (t, 2H), 5.17-5.27 (br-s, 1H), 6.11 (d, 1H), 6.81-6.86 (m, 2H), 7-06-7.09 (m, 1H), 7.13 (d, 1H), 7.29 (t, 1H), 7.38 (d, 1H), 7.48 (t, 1H), 7.52 (dt, 1H), 8.48 (d, 1H)

Step H

The title compound from Step G above (0.075 g, 0.137 mmol) was dissolved in dichloromethane (2 mL) and treated with a 2 M solution of hydrogen chloride in diethylether (2 mL). The reaction mixture was stirred at room temperature overnight and the solvents were removed using a syringe. The residue was dissolved in water (5 mL) and filtered through a 0.2 μm filter cartridge. The filtrate was collected and the solvent was evaporated using a freeze-dryer to afford the title compound as a pale orange foam (0.045 g, 72%).

$^1$H-NMR (400 MHz, D$_2$O): d=2.79 (s, 3H), 3.02 (t, 2H), 3.33 (t, 2H), 3.57 (t, 2H), 3.81 (t, 2H), 5.81 (d, 1H), 5.92 (d, 1H), 6.71 (d, 1H), 6.81 8d, 1H), 7.50 (t, 1H), 7.78 (t, 1H), 7.83-7.91 (m, 2H), 8.42 (t, 1H), 8.59 (d, 1H)

MS (ESI); m/z=349.42 (MH$^+$)

Preparation Example 4 Compound 2)

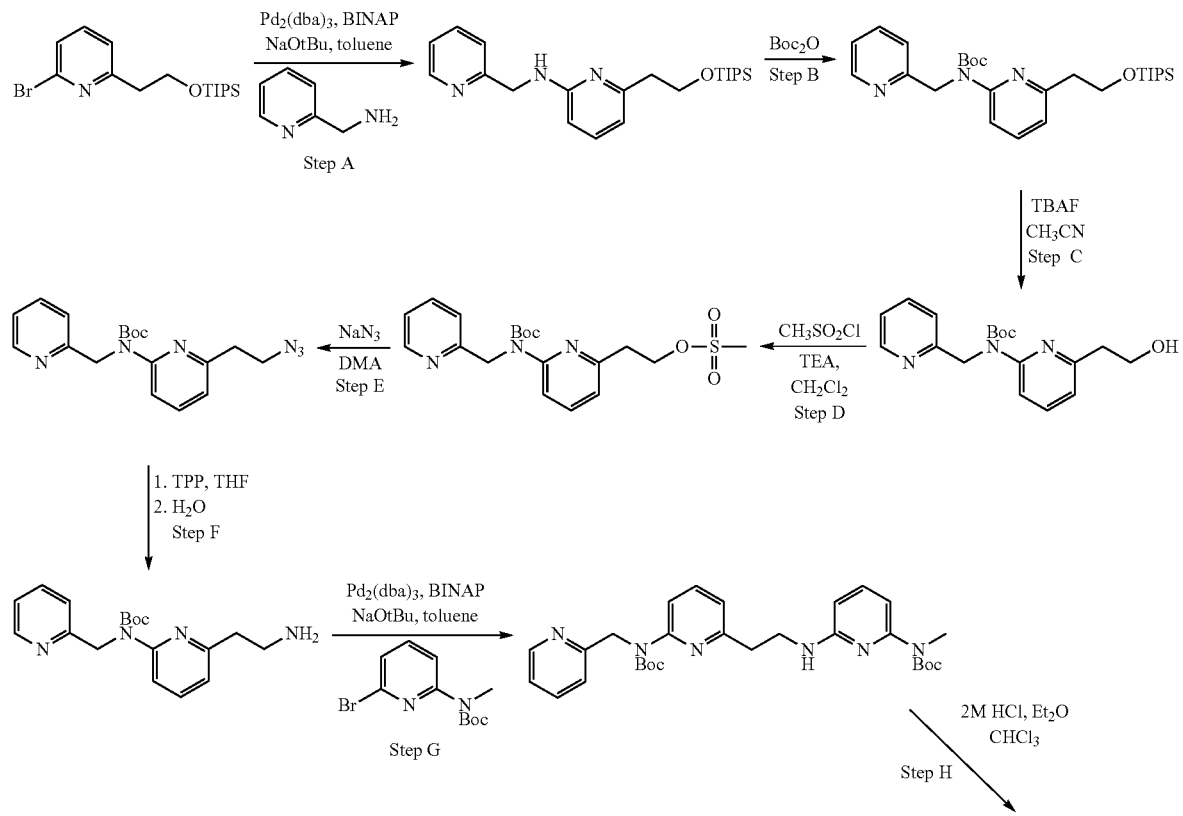

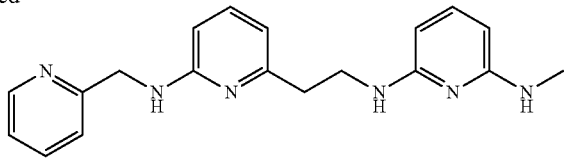

3x HCl

Step A

The title compound from Example 1 Step H (0.35 g, 0.95 mmol) and commercially available 2-aminomethyl-pyridine (0.108 g, 1 mmol) were dissolved in toluene (17 mL) and treated with 2,2-bis-(diphenylphosphino)-1,1-naphthalene (0.13 g, 0.19 mmol) and sodium tert-butylate (0.245 g, 2.58 mmol). The reaction mixture was then degassed by bubbling argon through the reaction mixture followed by the addition of tris(dibenzylideneacetone)dipalladium chloroform complex (0.086 g, 0.095 mmol). The reaction vessel was sealed and the mixture was heated at ~80 to 85° C. in a sand bath for 45 minutes. The reaction mixture was diluted with ethyl acetate (40 mL), water (10 mL) and brine (10 mL). The organic phase was separated, dried over $Na_2SO_4$, filtered and the solvents were removed. The residue was purified by chromatography on silica using dichloromethane/acetone (95/5) to elute unpolar impurities, followed by ethylacetate to elute the product. The crude material was again purified by chromatography on silica using ethylacetate/n-heptane (80/20) to afford the title compound as a pale orange oil (0.28 g, 75%).

$^1$H-NMR (400 MHz, $CDCl_3$): d=0.98-1.10 (m, 21H), 2.88 (t, 2H), 4.02 (t, 2H), 4.65 (d, 2H), 5.51 (br-s, 1H), 6.28 (d, 1H), 6.53 (d, 1H), 7.16-7.20 (m, 1H), 7.30-7.38 (m, 2H), 7.63 (dt, 1H), 8.58 (d, 1H)

Step B

The title compound from Step A above (0.28 g, 0.73 mmol) was dissolved in dichloromethane (5 mL) and di-tert-butyl dicarbonate (0.8 g, 3.65 mmol) was added. The solvent was removed and the oily residue was heated in a sand bath at ~75° C. for 3 days. The mixture was then purified by chromatography on silica using ethylacetate/n-heptane (10/90) to remove excess di-tert-butyl dicarbonate followed by ethylacetate/n-heptane (30/70) to afford the title compound as a pale yellow oil (0.32 g, 91%).

$^1$H-NMR (400 MHz, $CDCl_3$): d=0.85-1.10 (m, 21H), 1.38 (s, 9H), 2.88 (t, 2H), 3.90 (t, 2H), 5.31 (s, 2H), 6.91 (d, 1H), 7.12-7.17 (m, 1H), 7.28 (d, 1H), 7.54-7.62 (m, 2H), 7.67 (d, 1H), 8.54 (d, 1H)

Step C

The title compound from Step B above (0.32 g, 0.66 mmol) was dissolved in acetonitrile (8 mL) and treated with 1 M solution of tetrabutylammonium fluoride (3.3 mL, 3.3 mmol) in tetrahydrofuran. The mixture was stirred at room temperature overnight and the solvents were removed. The residue was purified by chromatography on silica using ethylacetate to afford the title compound as a pale orange oil (0.18 g, 84%).

$^1$H-NMR (400 MHz, $CDCl_3$): d=1.42 (s, 9H), 2.91 (t, 2H), 3.69 (br-s, 1H), 3.88 (t, 2H), 5.27 (s, 2H), 6.88 (d, 1H), 7.15-7.20 (m, 1H), 7.30 (d, 1H), 7.59 (t, 1H), 7.63-7.67 (m, 2H), 8.54 8d, 1H)

Step D

The title compound from Step C above (0.18 g, 0.56 mmol) was dissolved in dichloromethane (3 mL) and triethylamine (0.17 mL, 1.26 mmol) was added. The mixture was cooled to 0° C. and methanesulfonylchloride (0.09 mL, 1.12 mmol) was added. The reaction mixture was then stirred at room temperature for 1 h. The mixture then put onto a silica column equilibrated with ethylacetate. The column was developed with ethylacetate to afford the title compound as a pale yellow oil (0.22 g, 96%).

$^1$H-NMR (400 MHz, $CDCl_3$): d=1.42 (s, 9H), 2.82 (s, 3H), 3.07 (t, 2H), 4.43 (t, 2H), 5.30 (s, 2H), 6.91 (d, 1H), 7.18-7.23 (m, 1H), 7.29 (d, 1H), 7.61 (t, 1H), 7.69 (dt, 1H), 7.78 (d, 1H), 8.57 (d, 1H)

Step E

The title compound from Step D above (0.22 g, 0.54 mmol) was dissolved in N,N'-dimethylacetamide (2.1 mL) and sodium azide (0.18 g, 2.7 mmol) was added. The mixture was heated at ~75° C. in a sand bath overnight. The mixture was diluted with ethylacetate (25 mL) and water (10 mL). The organic phase was separated, washed with brine (10 mL), dried over $Na_2SO_4$, filtered and the solvents were removed. The residue was purified by chromatography on silica using ethylacetate/n-heptane (60/40) to afford the title compound as a colorless oil (0.15 g, 78%).

$^1$H-NMR (400 MHz, $CDCl_3$): d=1.42 (s, 9H), 2.88 (t, 2H), 3.49 (t, 2H), 5.30 (s, 2H), 6.90 (d, 1H), 7.13-7.18 (m, 1H), 7.22 (d, 1H), 7.59-7.66 (m, 2H), 7.77 (d, 1H), 8.55 (d, 1H)

Step F

The title compound from Step E above (0.15 g, 0.41 mmol) was dissolved in tetrahydrofuran (4 mL) and triphenylphosphine (0.13 g, 0.5 mmol) was added. The reaction mixture was stirred at room temperature for 24 h and then water (2 mL) was added. Stirring was continued over the weekend and the solvents were removed in vacuo. The residue was purified by chromatography on silica using dichloromethane/methanol (95/5) followed by dichloromethane/methanol (1/1, containing 10 mL 7 M ammonia in methanol per 500 mL) to afford the title compound as a colorless oil (0.135 g, 98%).

$^1$H-NMR (400 MHz, $CDCl_3$): d=1.42 (s, 9H), 2.79 (t, 2H), 2.94 (t, 2H), 5.30 (s, 2H), 6.88 (d, 1H), 7.12-7.16 (m, 1H), 7.26 (d, 1H), 7.58 (t, 1H), 7.61 (dt, 1H), 7.70 (d, 1H), 8.54 (d, 1H)

Step G

The title compound from Preparation Step F above (0.135 g, 0.41 mmol) and the title compound from Preparative Example 2 Step H (0.085 g, 0.4 mmol) were dissolved in toluene (7.2 mL) and treated with 2,2-bis-(diphenylphosphino)-1,1-naphthalene (0.05 g, 0.08 mmol) and sodium tert-butylate (0.125 g, 1.25 mmol). The reaction mixture was then degassed by bubbling argon through the reaction mixture followed by the addition of tris(dibenzylideneacetone) dipalladium chloroform complex (0.037 g, 0.04 mmol). The reaction vessel was sealed and the mixture was heated at ~110° C. in a sand bath for 45 minutes. The reaction mixture was diluted with ethyl acetate (40 mL), saturated sodium bicarbonate (10 mL) and brine (10 mL). The organic phase was separated, dried over $Na_2SO_4$, filtered and the solvents were removed. The residue was purified by chromatography on silica using dichloromethane/methanol (95/5) to elute less polar by-products, followed by dichloromethane/methanol (9/1) to elute a mixture of 2 compounds as judged by TLC (dichloromethane/methanol (9/1)). The solvents were removed and the crude mixture (87 mg, 46% combined) directly used for the next step.

Step E

The title compounds from Step B above (0.06 g, 0.183 mmol) and Step D above (0.048 g, 0.167 mmol) were dissolved in toluene (3 mL) and treated with 2,2-bis-(diphenylphosphino)-1,1-naphthalene (0.021 g, 0.034 mmol) and sodium tert-butylate (0.049 g, 0.51 mmol). The reaction mixture was then degassed by bubbling argon through the reaction mixture followed by the addition of tris(dibenzylideneacetone)dipalladium chloroform complex (0.015 g, 0.0167 mmol). The reaction vessel was sealed and the mixture was heated at ~110° C. in a sand bath for 45 minutes. The reaction mixture was diluted with ethyl acetate (20 mL), water (5 mL) and brine (5 mL). The organic phase was separated, dried over $Na_2SO_4$, filtered and the solvents were removed. The residue was purified by chromatography on silica using dichloromethane/acetone (95/5) to elute unpolar impurities, followed by ethylacetate/n-heptane (70/30) to elute the desired compound. To remove remaining impurities, the crude product was further purified by Prep-TLC (Analtech, 0.5 mm) using dichloromethane/methanol (95/5) as a mobile phase to afford the title compound as a dark yellow oil (0.023 g, 25%).

$^1$H-NMR (400 MHz, $CDCl_3$): d=1.40 (s, 9H), 1.50 (s, 9H), 2.92 (t, 2H), 3.30 (s, 3H), 3.50-3.54 (m, 2H), 4.69 (br-s, 1H), 5.31 (s, 2H), 5.92 (d, 1H), 6.82-6.88 (m, 2H), 7.11-7.14 (m, 1H), 7.27-7.30 (m, 2H), 7.55-7.62 (m, 2H), 7.70 (d, 1H), 8.53 (d, 1H)

Step F

The title compound from Step E above (0.023 g, 0.04 mmol) was dissolved in chloroform (0.8 mL) and treated with a 2 M solution of hydrogen chloride in diethylether (0.8 mL). The reaction mixture was stirred at room temperature overnight and the solvents were removed using a syringe. The solid material was dissolved in water (2 mL) and filtered through a 0.2 lam filter cartridge. The filtrate was collected and the solvent was evaporated to afford the title compound as a dark yellow glass (0.016 g, 84%).

$^1$H-NMR (400 MHz, $D_2O$): d=2.79 (s, 3H), 3.07 (t, 2H), 3.58 (t, 2H), 5.00 (s, 2H), 5.81 (d, 1H), 5.92 (d, 1H), 6.82 (d, 1H), 6.89 (d, 1H), 7.51 (t, 1H), 7.83-7.91 (m, 3H), 8.43 (t, 1H), 8.63 (d, 1H)

MS (ESI); m/z=335.44 (MH$^+$)

Preparation Example 5 (Compound 6)

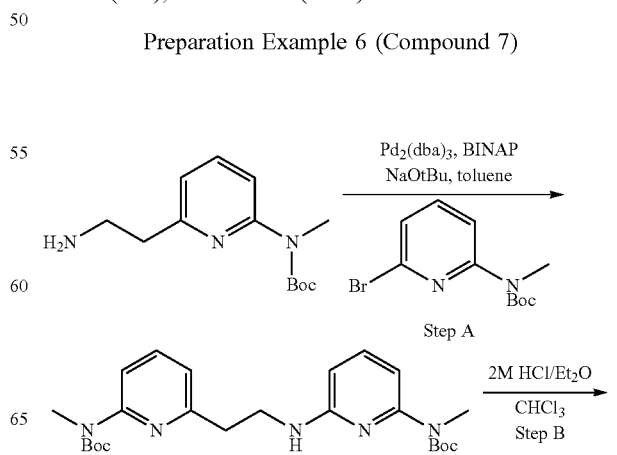

x2 HCl

Step A

Commercially available 2-(2-aminoethyl)-pyridin-2-yl (0.037 g, 0.3 mmol) and the title compound from Preparative Example 2 Step H (0.072 g, 0.25 mmol) were dissolved in toluene (4.5 mL) and treated with 2,2-bis-(diphenylphosphino)-1,1-naphthalene (0.031 g, 0.05 mmol) and sodium tert-butylate (0.075 g, 0.78 mmol). The reaction mixture was then degassed by bubbling argon through the reaction mixture followed by the addition of tris(dibenzylideneacetone) dipalladium chloroform complex (0.023 g, 0.025 mmol). The reaction vessel was sealed and the mixture was heated at ~110° C. in a sand bath for 45 minutes. The reaction mixture was diluted with ethyl acetate (20 mL), water (5 mL) and brine (5 mL). The organic phase was separated, dried over $Na_2SO_4$, filtered and the solvents were removed. The residue was purified by chromatography on silica using dichloromethane/acetone (95/5) to elute unpolar impurities, followed by ethylacetate/n-heptane (80/20) to elute the desired compound. To remove remaining impurities, the crude product was further purified by chromatography on silica using ethylacetate/n-heptane (80/20) to afford the title compound as a pale yellow oil (0.07 g, 85%).

$^1$H-NMR (400 MHz, $CDCl_3$): d=1.51 (s, 9H), 3.14 (t, 2H), 3.36 (s, 3H), 3.66-3.76 (m, 2H), 4.81 (br-s, 1H), 6.11 (d, 1H), 6.88 (d, 1H), 7.13-7.19 (m, 2H), 7.36 (t, 1H), 7.61 (dt, 1H), 8.56 (d, 1H)

Step B

The title compound from Step A above (0.062 g, 0.189 mmol) was dissolved in chloroform (2.75 mL) and treated with a 2 M solution of hydrogen chloride in diethylether (2.75 mL). The reaction mixture was stirred at room temperature overnight and the solvents were removed using a syringe. The solid material was dissolved in water (5 mL) and filtered through a 0.2 μm filter cartridge. The filtrate was collected and the solvent was evaporated to afford the title compound as a dark yellow glass (0.047 g, 84%).

$^1$H-NMR (400 MHz, $D_2O$): d=2.78 (s, 3H), 3.28 (t, 2H), 3.67 (t, 2H), 5.80 (d, 1H), 5.91 (d, 1H), 7.50 (t, 1H), 7.82 (t, 1H), 7.86 (d, 1H), 8.40 (t, 1H), 8.56 (d, 1H)

MS (ESI); m/z=229.30 (MH$^+$)

Preparation Example 6 (Compound 7)

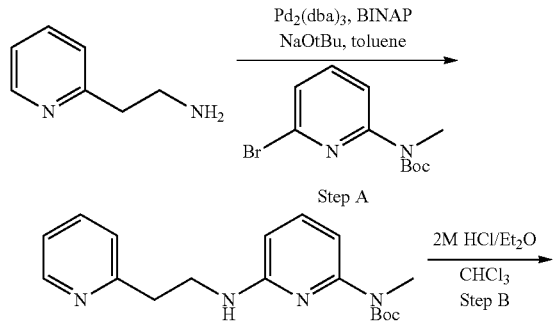

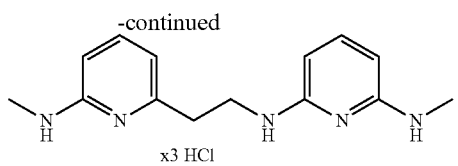

x3 HCl

Step A

The title compound from Example 1 Step F (0.075 g, 0.3 mmol) and the title compound from Example 2 Step H (0.072 g, 0.25 mmol) were dissolved in toluene (4.5 mL) and treated with 2,2-bis-(diphenylphosphino)-1,1-naphthalene (0.031 g, 0.05 mmol) and sodium tert-butylate (0.075 g, 0.78 mmol). The reaction mixture was then degassed by bubbling argon through the reaction mixture followed by the addition of tris(dibenzylideneacetone)dipalladium chloroform complex (0.023 g, 0.025 mmol). The reaction vessel was sealed and the mixture was heated at ~110° C. in a sand bath for 45 minutes. The reaction mixture was diluted with ethyl acetate (20 mL), water (5 mL) and brine (5 mL). The organic phase was separated, dried over $Na_2SO_4$, filtered and the solvents were removed. The residue was purified by chromatography on silica using dichloromethane/acetone (95/5) to elute unpolar impurities together with the desired compound (0.098 g). The product was further purified by chromatography on silica using ethylacetate/n-heptane (30/70) to afford the title compound as a pale yellow oil (0.09 g, 78%).

$^1$H-NMR (400 MHz, $CDCl_3$): d=1.51 (s, 9H), 1.54 (s, 9H), 3.04 (t, 2H), 3.33 (s, 3H), 3.44 (s, 3H), 3.64-3.70 (m, 2H), 5.02 (br-s, 1H), 6.12 (d, 1H), 6.86-6.90 (m, 2H), 7.37 (t, 1H), 7.53-7.57 (m, 2H)

Step B

The title compound from Step A above (0.09 g, 0.196 mmol) was dissolved in chloroform (2.9 mL) and treated with a 2 M solution of hydrogen chloride in diethylether (2.9 mL). The reaction mixture was stirred at room temperature overnight and the solvents were removed using a syringe. The solid material was dissolved in water (5 mL) and filtered through a 0.2 μm filter cartridge. The filtrate was collected and the solvent was evaporated to afford the title compound as a dark yellow glass (0.057 g, 80%).

$^1$H-NMR (400 MHz, $D_2O$): d=2.78 (s, 3H), 2.89 (s, 3H), 2.98 (t, 2H), 3.57 (t, 2H), 5.80 (d, 1H), 5.90 (d, 1H), 6.63 (d, 1H), 6.77 (d, 1H), 7.50 (t, 1H), 7.68 (t, 1H)

MS (ESI); m/z=258.28 ($MH^+$)

Preparation Example 7 (Compound 4)

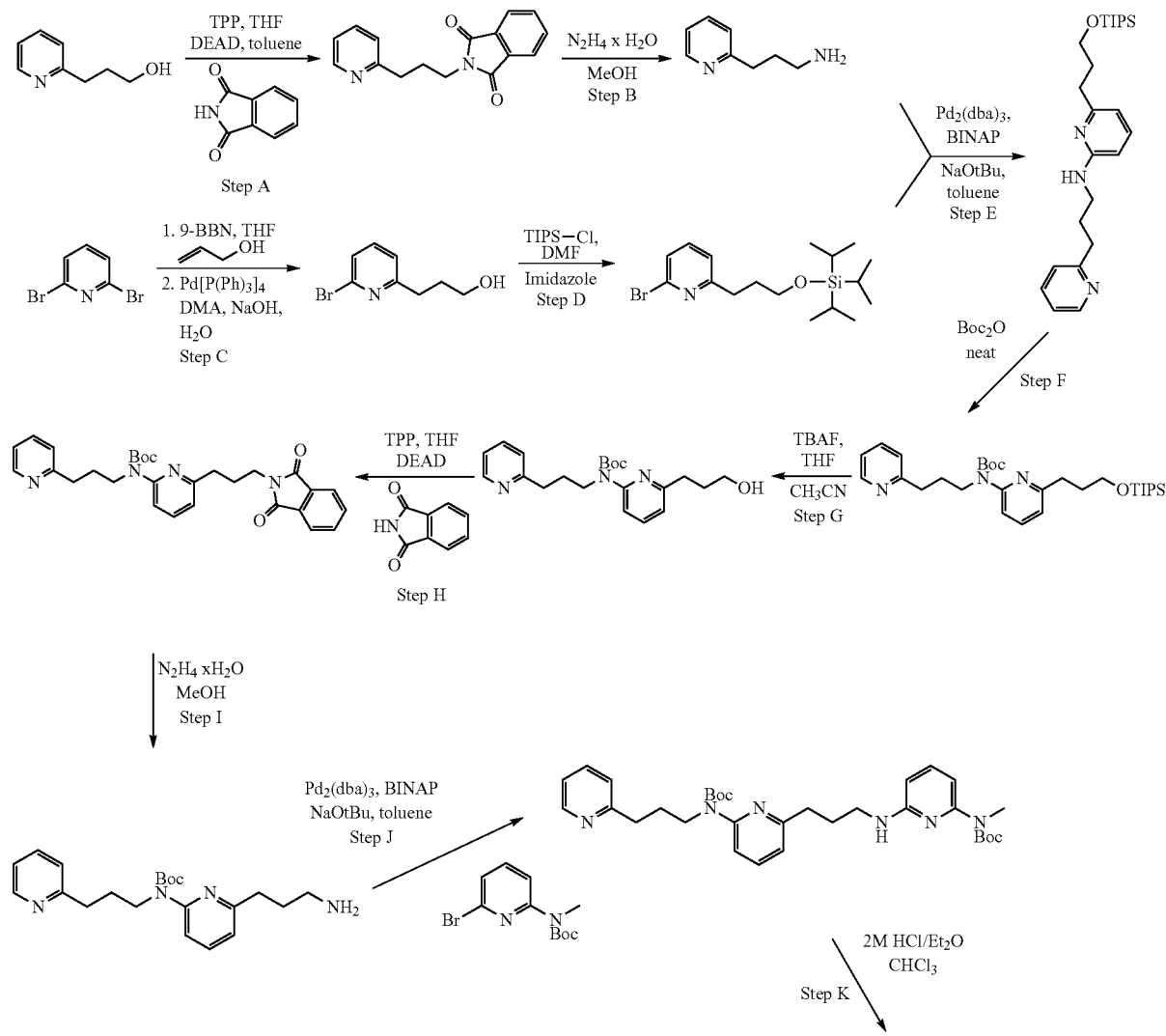

-continued

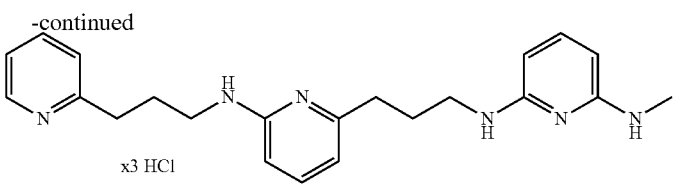

x3 HCl

Step A

Triphenylphosphine (3.8 g, 14.4 mmol) and phthalimide (1.08 g, 7.4 mmol) were dissolved in tetrahydrofuran (20 mL) and the mixture was cooled to 0° C. At 0° C. a mixture of commercially available 2-pyridin-1-propanol (1 g, 7.4 mmol) in tetrahydrofuran (10 mL) and a 40% solution of diethyl azodicarboxylate in toluene (6 mL, 14.4 mmol) were added over a period of 5 min. The mixture was stirred overnight and allowed to reach room temperature. The solvents were removed and the residue was purified by chromatography on silica using ethylacetate/n-heptane (60/40) to afford the title compound as a red oil (1.9 g, 98%).

$^1$H-NMR (400 MHz, CDCl$_3$): d=2.13-2.21 (m, 2H), 2.87 (t, 2H), 3.80 (t, 2H), 7.07-7.11 (m, 1H), 7.20 (d, 1H), 7.58 (dt, 1H), 7.69-7.72 (m, 2H), 7.83-7.86 (m, 2H), 8.50 (d, 1H)

Step B

The title compound from Step A above (1.9 g, 7 mmol) was dissolved in methanol (50 mL) and treated with a 50% solution of hydrazine in water (1.4 mL, 14 mmol). The mixture was stirred at room temperature overnight and the solvents were removed. The solid was treated with dichloromethane (100 mL) and sonicated for 5 min to obtain a slurry, which was stirred at room temperature for 30 min. The mixture was filtered and the precipitate was washed with 30 mL dichloromethane. The filtrate was concentrated and the residue was purified by chromatography on silica using dichloromethane/methanol (9/1) to elute colored impurities followed by dichloromethane/methanol (1:1) containing 10 mL 7 M ammonia in methanol per 500 mL to afford the title compound as a brown liquid (0.69 g, 70%).

$^1$H-NMR (400 MHz, CDCl$_3$): d=1.43 (br-s, 2H), 1.85-1.92 (m, 2H), 2.74 (t, 2H), 2.83 (t, 2H), 7.08-7.12 (m, 1H), 7.16 (d, 1H), 7.59 (dt, 1H), 8.52 (d, 1H)

Step C

Allyl alcohol (0.087 mL, 1.5 mmol) was dissolved in tetrahydrofuran (3 mL) and the mixture was cooled to 0° C. At 0° C. a 0.4 M solution of 9-borabicyclo[3.3.1]nonane in hexane (11.25 mL, 4.5 mmol) was added and stirring at 0° C. was continued for 15 min. The mixture was then stirred at room temperature for 4 h and the solvents were evaporated. The residue was dissolved in tetrahydrofuran (8 mL) and a 3 M aqueous solution of sodium hydroxide (2 mL, 6 mmol) was added. After the addition of a solution of commercially available 2,6-dibromo-pyridine (0.46 g, 1.95 mmol) in N,N'-dimethylacetamide (10 mL), the mixture was sonicated for 5 min while a stream of argon was bubbled through the mixture. Then tetrakis(triphenylphosphine)palladium(0) (0.17 g, 0.156 mmol) was added and the mixture was heated at ~95° C. in a sand bath for 90 min. The mixture was diluted with ethylacetate (50 mL) and washed with 10% citric acid (20 mL) and brine (15 mL). The organic phase was separated, dried over Na$_2$SO$_4$, filtered and the solvents were removed. The residue was purified by chromatography on silica using ethylacetate/n-heptane (30/70) to elute colored impurities followed by ethylacetate/n-heptane (60/40) to afford the crude product. The combined crude products from this and two additional runs were further purified by chromatography on silica using ethylacetate/n-heptane (50/50) to afford the title compound as a pale yellow oil (0.48 g, 49%).

$^1$H-NMR (400 MHz, CDCl$_3$): d=1.97-2.03 (m, 2H), 2.92 (t, 2H), 3.68-3.73 (m, 2H), 7.12 (d, 1H), 7.34 (d, 1H), 7.42 (t, 1H)

Note: $^1$H-NMR showed the presence of small amounts of decomposition products of 9-BBN, but the material is pure enough for use in the next step.

Step D

The title compound from Step C above (0.48 g, 2.23 mmol) was dissolved in N,N'-dimethylformamide (10 mL) and imidazole (0.3 g, 4.46 mmol) was added. After the addition of chlorotriisopropylsilane (0.43 g, 2.23 mmol), the mixture was stirred at room temperature for 16 h. The reaction mixture was diluted with ethylacetate (60 mL) and washed with a 10% citric acid solution (3×15 mL) and brine (15 mL). The organic phase was separated, dried over Na$_2$SO$_4$, filtered and the solvents were removed. The residue was purified by chromatography on silica using ethylacetate/n-heptane (5/95) to afford the title compound as a colorless liquid (0.66 g, 79%).

$^1$H-NMR (400 MHz, CDCl$_3$): (=1.05-1.14 (m, 21H), 1.94-2.01 (m, 2H), 2.88 (t, 2H), 3.72 (t, 2H), 7.14 (d, 1H), 7.31 (d, 1H), 7.45 (t, 1H)

Step E

The title compounds from Step B (0.136 g, 1 mmol) and from Step D (0.35 g, 0.95 mmol) above were dissolved in toluene (17 mL) and treated with 2,2-bis-(diphenylphosphino)-1,1-naphthalene (0.13 g, 0.19 mmol) and sodium tert-butylate (0.25 g, 2.58 mmol). The reaction mixture was then degassed by bubbling argon through the reaction mixture followed by the addition of tris(dibenzylideneacetone)dipalladium chloroform complex (0.086 g, 0.095 mmol). The reaction vessel was sealed and the mixture heated at ~85° C. in a sand bath for 45 minutes. The reaction mixture was diluted with ethyl acetate (80 mL), water (20 mL) and brine (20 mL). The organic phase was separated, dried over Na$_2$SO$_4$, filtered and the solvents were removed. The residue was purified by chromatography on silica using dichloromethane/acetone (95/5) to elute unpolar impurities, followed by ethylacetate/n-heptane (80/20) to elute the desired compound. The crude product was again purified by chromatography on silica using ethylacetate/n-heptane (80/20) to afford the title compound as a dark yellow oil (0.34 g, 83%).

$^1$H-NMR (400 MHz, CDCl$_3$): d=1.05-1.14 (m, 21H), 1.92-1.97 (m, 2H), 2.05-2.12 (m, 2H), 2.68 (t, 2H), 2.91 (t, 2H), 3.27-3.33 (m, 2H), 3.74 (t, 2H), 4.60-4.63 (br-s, 1H), 6.18 (d, 1H), 6.46 (d, 1H), 7.10-7.13 (m, 1H), 7.17 (d, 1H), 7.32 (t, 1H), 7.60 (dt, 1H), 8.52 (d, 1H)

Step F

The title compound from Step E above (0.34 g, 0.79 mmol) was dissolved in dichloromethane (5 mL) and di-tert-butyl dicarbonate (0.86 g, 3.95 mmol) was added. The solvent was removed and the oily residue was heated in a sand bath at ~75° C. for 3 days until all starting material had disappeared as judged by TLC. The mixture was then purified by chromatography on silica using ethylacetate/n-heptane (10/90) to elute excess of di-tert-butyl dicarbonate followed by ethylacetate/n-heptane (30/70) afford the title compound as an orange oil (0.38 g, 92%).

$^1$H-NMR (400 MHz, CDCl$_3$): d=1.05-1.14 (m, 21H), 1.49 (s, 9H), 1.99-1.96 (m, 2H), 2.05-2.12 (m, 2H), 2.74-2.84 (m, 4H), 3.72 (t, 2H), 4.01 (t, 2H), 6.88 (d, 1H), 7.07-7.10 (m, 1H), 7.12 (d, 1H), 7.39 (d, 1H), 7.52 (t, 1H), 7.58 (dt, 1H), 8.51 (d, 1H)

Step G

The title compound from Step F above (0.38 g, 0.72 mmol) was dissolved in acetonitrile (8 mL) and a 1 M solution of tetrabutylammonium fluoride (3.6 mL, 3.6 mmol) in tetrahydrofuran was added. The mixture was stirred at room temperature overnight and the solvents were removed. The residue was purified by chromatography on silica using ethylacetate to afford the title compound as a pale yellow oil (0.25 g, 94%).

$^1$H-NMR (400 MHz, CDCl$_3$): d=1.49 (s, 9H), 2.00-2.11 (m, 4H), 2.81-2.89 (m, 4H), 3.68 (t, 2H), 4.02 (t, 2H), 6.88 (d, 1H), 7-08-7.12 (m, 1H), 7.16 (d, 1H), 7.41 (d, 1H), 7.52 (t, 1H), 7.59 (t, 1H), 8.47 (d, 1H)

Step H

Triphenylphosphine (0.35 g, 1.36 mmol) and phthalimide (0.1 g, 0.68 mmol) were dissolved in tetrahydrofuran (3 mL) and the mixture was cooled to 0° C. At 0° C. a mixture of the title compound from Step G above (0.25 g, 0.68 mmol) in tetrahydrofuran (2 mL) and a 40% solution of diethyl azodicarboxylate in toluene (0.55 mL, 1.36 mmol) were added over a period of 5 min. The mixture was stirred overnight and allowed to reach room temperature. The solvents were removed and the residue was purified by chromatography on silica using ethylacetate/n-heptane (60/40) to afford the title compound as an orange oil (382 mg).

$^1$H-NMR (400 MHz, CDCl$_3$): d=1.49 (s, 9H), 2.00-2.17 (m, 4H), 2.77 (t, 2H), 2.81 (t, 2H), 3.76 (t, 2H), 4.03 (t, 2H), 6.88 (d, 1H), 7.04-7.08 (m, 1H), 7.14 (d, 1H), 7.38 (d, 1H), 7.48 (t, 1H), 7.55 (t, 1H), 7.69-7.72 (m, 2H), 7.82-7.86 (m, 2H), 8.48 (d, 1H)

Note: $^1$H-NMR showed the presence of small amounts of diethyl hydrazine-1,2-dicarboxylate, but the material is pure enough for use in the next step.

Step I

The title compound from Step H above (0.34 g, 0.68 mmol) was dissolved in methanol (7 mL) and treated with a 50% solution of hydrazine in water (0.14 mL, 1.36 mmol). The mixture was stirred at room temperature overnight and the solvents were removed. The solid was treated with dichloromethane (20 mL) and sonicated for 5 min to obtain a slurry, which was stirred at room temperature for 30 min. The mixture was filtered and the precipitate was washed with 10 mL dichloromethane. The filtrate was concentrated and the residue was purified by chromatography on silica using dichloromethane/methanol (9/1) to elute colored impurities followed by dichloromethane/methanol (1:1) containing 10 mL 7 M ammonia in methanol per 500 mL to afford the title compound as a pale yellow oil (0.16 g, 62%).

$^1$H-NMR (400 MHz, CDCl$_3$): d=1.52 (s, 9H), 1.86 (q, 2H), 2.08 (q, 2H), 2.70-2.76 (m, 4H), 2.83 (t, 2H), 4.04 (t, 2H), 6.85 (d, 1H), 7.08-7.11 (m, 1H), 7.14 (d, 1H), 7.40 (d, 1H), 7.52 (t, 1H), 7.57 (t, 1H), 8.51 (d, 1H)

Step J

The title compound from Step I above (0.075 g, 0.2 mmol) and the title compound from Example 2 Step H (0.055 g, 0.193 mmol) were dissolved in toluene (3.1 mL) and treated with 2,2-bis-(diphenylphosphino)-1,1-naphthalene (0.024 g, 0.039 mmol) and sodium tert-butylate (0.05 g, 0.52 mmol). The reaction mixture was then degassed by bubbling argon through the reaction mixture followed by the addition of tris(dibenzylideneacetone)dipalladium chloroform complex (0.017 g, 0.019 mmol). The reaction vessel was sealed and the mixture was heated at ~110° C. in a sand bath for 45 minutes. The reaction mixture was diluted with ethyl acetate (20 mL), water (5 mL) and brine (5 mL). The organic phase was separated, dried over Na$_2$SO$_4$, filtered and the solvents were removed. The residue was purified by chromatography on silica using dichloromethane/acetone (95/5) to elute unpolar impurities followed by ethylacetate/n-heptane (60/40) to elute the desired compound. The crude product was again purified by chromatography on silica using ethylacetate/n-heptane (60/40) to afford the title compound as a pale yellow oil (0.094 g, 89%).

$^1$H-NMR (400 MHz, CDCl$_3$): d=1.50 (s, 9H), 1.52 8s, 9H), 2.00-2.12 (m, 4H), 2.78-2.84 (m, 4H), 3.27-3.33 (m, 5H), 4.02 (t, 2H), 4.70 (br-s, 1H), 6.08 (d, 1H), 6.86 (d, 2H), 7.08-7.13 (m, 2H), 7.34 (t, 1H), 7.40 (d, 1H), 7.48-7.57 (m, 2H), 8.50 (d, 1H)

Step K

The title compound from Step J above (0.094 g, 0.16 mmol) was dissolved in chloroform (2.3 mL) and treated with a 2 M solution of hydrogen chloride in diethylether (2.3 mL). The reaction mixture was stirred at room temperature overnight and the solvents were removed using a syringe. The solid material was dissolved in water (5 mL) and filtered through a 0.2 μm filter cartridge. The filtrate was collected and the solvent was evaporated to afford the title compound as an orange glass (0.06 g, 76%).

$^1$H-NMR (400 MHz, D$_2$O): d=1.97 (q, 2H), 2.06 (q, 2H), 2.73-2.79 (m, 5H), 3.07 (t, 2H), 3.25 (t, 2H), 3.36 (t, 2H), 5.82-5.87 (m, 2H), 6.66 (d, 1H), 6.73 (d, 1H), 7.50 (t, 1H), 7.72 (t, 1H), 7.78 (t, 1H), 7.83 (d, 1H), 8.39 (t, 1H), 8.51 (d, 1H)

MS (ESI); m/z=377.17 (MH$^+$)

Preparation Example 8 (Compound 3)

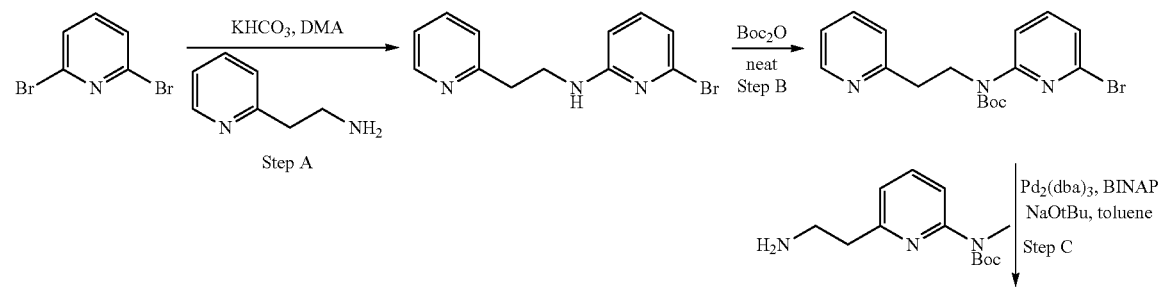

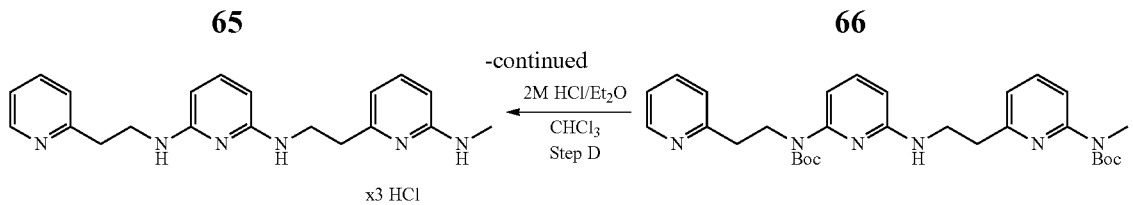

x3 HCl

Step A

Commercially available 2,6-dibromo pyridine (0.5 g, 2.1 mmol) was dissolved in N,N'-dimethylacetamide (5 mL) and commercially available 2-pyridyl-ethylamine (0.26 g, 2.1 mmol) was added. After the addition of potassium bicarbonate (0.23 g, 2.3 mmol), the mixture was heated at ~110° C. in a sand bath for 5 h. The mixture was diluted with ethylacetate (80 mL) and washed with water 83×20 mL. The organic phase was separated, dried over $Na_2SO_4$, filtered and the solvents were removed. The residue was purified by chromatography on silica using ethylacetate to afford the title compound as an orange oil (0.13 g, 21%).

$^1$H-NMR (400 MHz, $CDCl_3$): d=3.07 (t, 2H), 3.68 (m, 2H), 5.17 (br-s, 1H), 6.30 (d, 1H), 6.70 (d, 1H), 7.10-7.21 (m, 3 H), 7.58 (t, 1H), 8.52 (d, 1H)

Step B

The title compound from Step A above (0.13 g, 0.46 mmol) was dissolved in dichoromethane (3 mL) and di-tert-butyl dicarbonate (0.5 g, 2.32 mmol) was added. The solvent was removed and the oily residue was heated in a sand bath at ~75° C. for 3 days. The mixture was then purified by chromatography on silica using ethylacetate/n-heptane (20/80) to elute excess of di-tert-butyl dicarbonate followed by ethylacetate/n-heptane (40/60) afford the title compound as a pale yellow oil (0.095 g, 53%).

$^1$H-NMR (400 MHz, $CDCl_3$): d=1.49 (s, 9H), 3.18 (t, 2H), 4.38 (t, 2H), 7.11-7.14 (m, 1H), 7.18 (d, 1H), 7.23 (d, 1H), 7.48 (t, 1H), 7.59-7.67 (m, 2H), 8.52 (d, 1H)

Step C

The title compound from Step B above (0.09 g, 0.238 mmol) and the title compound from Example 1 Step F (0.07 g, 0.27 mmol) were dissolved in toluene (4.25 mL) and treated with 2,2-bis-(diphenylphosphino)-1,1-naphthalene (0.032 g, 0.048 mmol) and sodium tert-butylate (0.061 g, 0.65 mmol). The reaction mixture was then degassed by bubbling argon through the reaction mixture followed by the addition of tris(dibenzylideneacetone)dipalladium chloroform complex (0.021 g, 0.024 mmol). The reaction vessel was sealed and the mixture was heated at ~110° C. in a sand bath for 45 minutes. The reaction mixture was diluted with ethyl acetate (20 mL), water (5 mL) and brine (5 mL). The organic phase was separated, dried over $Na_2SO_4$, filtered and the solvents were removed. The residue was purified by chromatography on silica using dichloromethane/acetone (95/5) to elute unpolar impurities followed by ethylacetate/n-heptane (60/40) to elute the desired compound. The crude product was again purified by chromatography on silica using ethylacetate/n-heptane (60/40) to afford the title compound as a pale yellow oil (0.12 g, 94%).

$^1$H-NMR (400 MHz, $CDCl_3$): d=1.42 (s, 9H), 1.53 (s, 9H), 3.04 (t, 2H), 3.18 (t, 2H), 3.43 (s, 3H), 3.68-3.73 (m, 2H), 4.30 (t, 2H), 5.00 (br-s, 1H), 6.14 (d, 1H), 6.83 (d, 1H), 6.86-6.89 (m, 1H), 7.09-7.11 (m, 1H), 7.16 (d, 1H), 7.38 (t, 1H), 7.53-7.58 (m, 3H), 8.51 8d, 1H)

Step D

The title compound from Step C above (0.12 g, 0.22 mmol) was dissolved in chloroform (3.1 mL) and treated with a 2 M solution of hydrogen chloride in diethylether (3.1 mL). The reaction mixture was stirred at room temperature overnight and the solvents were removed using a syringe. The solid material was dissolved in water (5 mL) and filtered through a 0.2 lam filter cartridge. The filtrate was collected and the solvent was evaporated to afford the title compound as an orange glass (0.074 g, 74%).

$^1$H-NMR (400 MHz, $D_2O$): d=2.90 (s, 3H), 3.00 (t, 2H), 3.31 (t, 2H), 3.58 (t, 2H), 3.69 (t, 2H), 5.88-5.93 (m, 2H), 6.61-6.65 (m, 1H), 6.79 (d, 1H), 7.50-7.73 (m, 1H), 7.70 (t, 1H), 7.84-7.91 (m, 2H), 8.42 (t, 1H), 8.58 (d, 1H)

MS (ESI); m/z=349.49 (MH$^+$)

Preparation Example 9 (Compound 9)

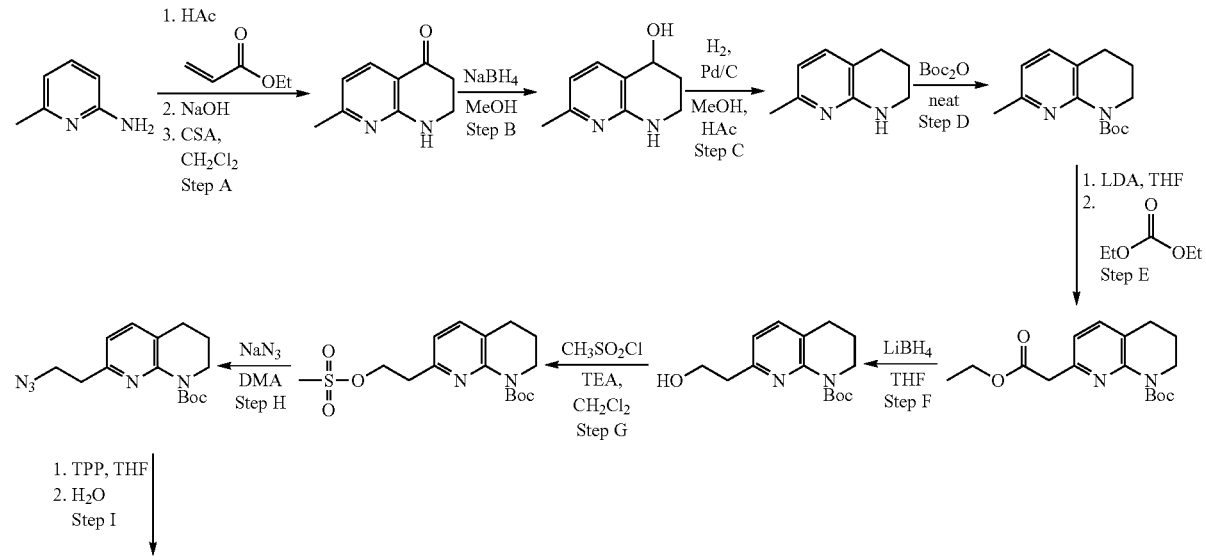

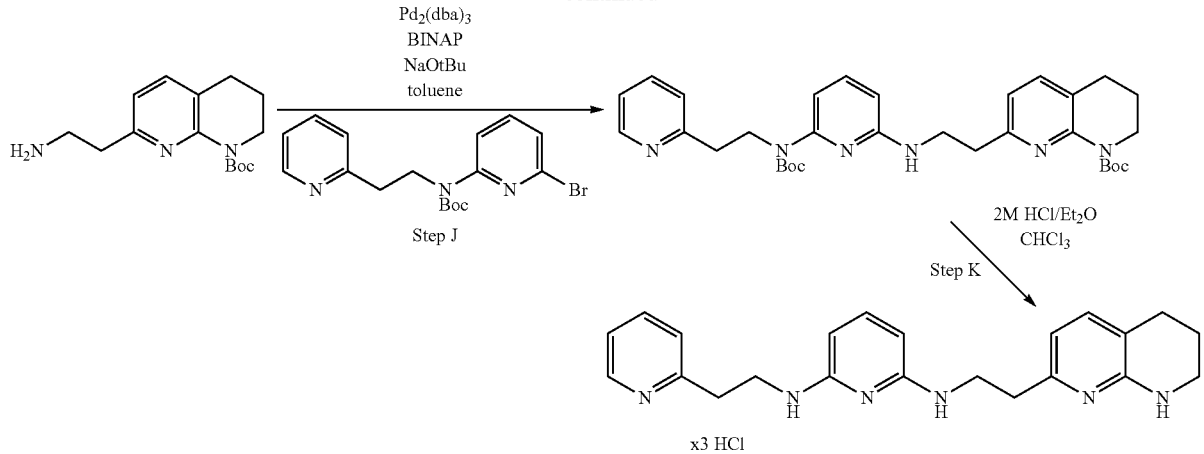

Step A

To commercially available 2-amino-6-methylpyridine (25.46 g, 235 mmol) was added ethyl acrylate (26 mL, 239 mmol) and acetic acid (6 mL, 105 mmol). This mixture was heated at ~150° C. in a sand bath for 50 h. The mixture was cooled to room temperature and 6 N sodium hydroxide (120 mL, 720 mmol) was added. The mixture was then heated at ~120° C. in a sand bath for 1 h. The mixture was cooled to room temperature and concentrated hydrochloric acid was added until the pH reached approx. 4-5 with ice-cooling. A polymeric precipitate was formed and the mixture was filtered. The filtrate was evaporated and the residue was treated with methanol (100 mL). The resulting slurry was stirred at room temperature for 30 minutes and filtered. The precipitate was washed with methanol (30 mL) and the combined filtrates were evaporated to leave a brownish, sticky mass. This crude material was dissolved in dichloromethane (400 mL) and the solution was placed in an ice-bath. Then chlorosulfonic acid (162 mL, 2430 mmol) was added dropwise. After the addition was completed, the mixture was stirred at room temperature for 2 h. Then the mixture was placed back into the ice-bath and water (800 mL) was carefully added. After the addition was completed, the acidic solution was made alkaline to pH ~6 by adding sodium hydroxide. Then sodium carbonate was added to adjust the pH to ~10 to 11. A precipitate was formed and the mixture was extracted with ethyl acetate (3×400 mL). The organic phase was separated, dried over $Na_2SO_4$, filtered and the solvents were removed. The residue was purified by chromatography on silica using ethyl acetate/n-heptane (75/25) to elute unpolar impurities, followed by ethyl acetate to afford the title compound as a yellow solid (12.2 g, 32%).

$^1$H-NMR (400 MHz, $CDCl_3$): d=2.40 (s, 3H), 2.69 (t, 2H), 3.58-3.62 (m, 2H), 5.31 8br-s-, 1H), 6.58 (d, 1H), 7.97 (d, 1H)

Step B

The title compound from Step A above (7 g, 43.2 mmol) was suspended in methanol (170 mL) and sodium borohydride (2.94 g, 77.7 mmol) was added in portions. After the addition was completed, the mixture was stirred at room temperature for 1 h to become a clear solution. Then acetic acid (21 mL) was added and the solvents were removed. The residue was dissolved in water (250 mL) and the aqueous phase was washed with dichloromethane (2×100 mL). The aqueous phase was made alkaline (pH ~10) by adding sodium carbonate and extracted with ethyl acetate (6×150 mL). The combined organic phase was dried over $Na_2SO_4$, filtered and the solvents were removed to afford the title compound as an off-white solid (6.39 g, 90%).

$^1$H-NMR (400 MHz, $CDCl_3$): d=1.82-1.90 (m, 1H), 1.95-2.01 (m, 1H), 2.30 (s, 3H), 3.10 (br-s, 1H), 3.31-3.36 (m, 1H), 3.48 (dt, 1H), 4.72 (t, 1H), 5.32 (br-s, 1H), 6.38 (d, 1H), 7.32 (d, 1H)

Step C

The title compound from Step B above (6.39 g, 38.9 mmol) was dissolved in methanol (130 mL) and acetic acid (65 mL). After the addition of 10% palladium on carbon catalyst (1.6 g), the mixture was hydrogenated for 3 days. The mixture was filtered, the catalyst was washed with methanol (50 mL) and the combined filtrates were evaporated. The acetate salt was dissolved in water (200 mL) and the pH was adjusted to pH ~10 by adding sodium carbonate. The aqueous phase was extracted with dichloromethane (3×150 mL). The combined organic phase was dried over $Na_2SO_4$, filtered and the solvents were removed to afford the free amine as a white solid (4.42 g, 76%).

$^1$H-NMR (400 MHz, $CDCl_3$): d=1.86-1.92 (m, 2H), 2.30 (s, 3H), 2.68 (t, 2H), 3.37-3.41 (m, 2H), 4.80 (br-s, 1H), 6.34 (d, 1H), 7.03 (d, 1H)

Step D

To the title compound from Step C above (7.42 g, 50.13 mmol) was added a solution of di-tert-butyl dicarbonate (33.7 g, 150.4 mmol) in dichloromethane (100 mL). The solvent was removed and the oily residue was heated at ~75° C. in a sand bath for 18 h. The reaction mixture was purified by chromatography on silica using ethyl acetate/n-heptane (10/90) to remove excess di-tert-butyl dicarbonate followed by ethyl acetate/n-heptane (40/60) to afford the title compound as a white solid (11.2 g, 90%).

$^1$H-NMR (400 MHz, $CDCl_3$): d=1.52 (s, 9H), 1.87-1.93 (m, 2H), 2.46 (s, 3H), 2.70 (t, 2H), 3.72 (t, 2H), 6.80 (d, 1H), 7.24 (d, 1H)

Step E

A solution of LDA was prepared by adding a 1.6 M solution of n-butyllithium (39.24 mL, 62.82 mmol) at 0° C. to a stirred solution of N,N'-diisopropylamine (9.9 mL, 75.4 mmol) in tetrahydrofuran (45 mL). The mixture was stirred at 0° C. for 15 min. The LDA solution was then added dropwise at −78° C. to a solution of the title compound from Step D above (5.6 g, 22.56 mmol) and diethylcarbonate (10.08 mL, 83.1 mmol) in tetrahydrofuran (72 mL). The mixture was stirred at −78° C. for 40 minutes. The reaction was quenched by adding a solution of saturated ammonium chloride (100 mL) at −8° C. The mixture was allowed to reach room temperature and was diluted with ethylacetate (200 mL). The organic phase was separated, dried over $Na_2SO_4$, filtered and the solvents were removed. The residue was purified by chromatography on silica using ethylacetate/ n-heptane (50/50) to afford the title compound as a yellow oil, which became a solid by standing at room temperature (7 g, 96%).

$^1$H-NMR (400 MHz, CDCl$_3$): d=1.25 (t, 3H), 1.51 (s, 9H), 1.88-1.93 (m, 2H), 2.72 (t, 2H), 3.71-3.75 (m, 4H), 4.13 (q, 2H), 6.96 (d, 1H), 7.34 (d, 1H)

Step F

The title compound from Step E above (2 g, 6.25 mmol) was dissolved in tetrahydrofuran (40 mL) and lithium borohydride (0.18 g, 8.14 mmol) was added in portions. The reaction mixture was stirred at room temperature overnight. Then water (25 mL) was added and the mixture was stirred at room temperature for 10 min. After the addition of ethylacetate (150 mL), the organic phase was separated and the aqueous phase was extracted with ethylacetate (50 mL). The combined organic phase was dried over Na$_2$SO$_4$, filtered and the solvents were removed. The residue was purified by chromatography on silica using ethylacetate to afford the title compound as a colorless oil (1.48 g, 85%), followed by dichloromethane/methanol (4/1) to afford the N-Boc deprotected product as a yellow oil (0.13 g, 11%).

Title compound:
$^1$H-NMR (400 MHz, CDCl$_3$): d=1.51 (s, 9H), 1.88-1.93 (m, 2H), 2.70 (t, 2H), 2.92 (t, 2H), 3.77 (t, 2H), 3.98 (t, 2H), 5.53 (br-s, 1H), 6.75 (d, 1H), 7.30 (d, 1H)

N-Boc deprotected product:
$^1$H-NMR (400 MHz, CDCl$_3$): d=1.87-1.93 (m, 2H), 2.03 (s, 1H), 2.68 (t, 2H), 2.80 (t, 2H), 3.40 (t, 2H), 3.89 (t, 2H), 6.32 (d, 1H), 6.48 (br-s, 1H), 7.10 (d, 1H)

Step G

The title compound from Step F above (822 mg, 2.95 mmol) was dissolved in dichloromethane (15 mL) and triethylamine (0.9 mL, 6.5 mmol) was added. After the addition of methanesulfonylchloride (0.46 mL, 5.87 mmol), the reaction mixture was stirred at room temperature for 1 h. The mixture was diluted with dichloromethane (50 mL) and washed with 10% citric acid solution (20 mL), saturated sodium bicarbonate (20 mL) and brine (20 mL). The organic phase was separated, dried over Na$_2$SO$_4$, filtered and the solvents were removed. The residue was purified by chromatography on silica using ethylacetate/n-heptane (80/20) to afford the title compound as a colorless oil (0.83 g, 78%).

$^1$H-NMR (400 MHz, CDCl$_3$): d=1.51 (s, 9H), 1.88-1.93 (m, 2H), 2.72 (t, 2H), 2.92 (s, 3H), 3.12 (t, 2H), 3.74 (t, 2H), 4.65 (t, 2H), 6.86 (d, 1H), 7.32 (d, 1H)

Step H

The title compound from Step G above (0.83 g, 2.22 mmol) was dissolved in N,N'-dimethylacetamide (5.5 mL) and sodium azide (0.76 g, 11.65 mmol) was added. The mixture was heated in a sand bath at ~75° C. for 16 h. The mixture was diluted with ethylacetate (55 mL) and 10% citric acid solution (15 mL). The organic phase was separated, washed with saturated sodium bicarbonate (15 mL) and brine (15 mL). The organic phase was dried over Na$_2$SO$_4$, filtered and the solvents were removed. The residue was purified by chromatography on silica using ethylacetate/ n-heptane (40/60) to afford the title compound as a pale yellow oil (0.6 g, 84%).

$^1$H-NMR (400 MHz, CDCl$_3$): d=1.51 (s, 9H), 1.88-1.93 (m, 2H), 2.72 (t, 2H), 2.98 (t, 2H), 3.69 (t, 2H), 3.74 (t, 2H), 6.84 (d, 1H), 7.32 (d, 1H)

Step I

The title compound from Step H above (0.6 g, 1.98 mmol) was dissolved in tetrahydrofuran (8 mL) and triphenylphosphine (0.63 g, 2.38 mmol) was added. The reaction mixture was stirred at room temperature for 20 h and then water (4 mL) was added. Stirring was continued overnight and the solvents were removed in vacuo. The residue was purified by chromatography on silica using dichloromethane/methanol (95/5) followed by dichloromethane/methanol (1/1, containing 10 mL 7 M ammonia in methanol per 500 mL) to afford the title compound as a pale yellow oil (0.5 g, 91%).

$^1$H-NMR (400 MHz, CDCl$_3$): d=1.52 (s, 9H), 1.66 (br-s, 2H), 1.89-1.96 (m, 2H), 2.72 (t, 2H), 2.87 (t, 2H), 3.11 (t, 2H), 3.78 (t, 2H), 6.80 (d, 1H), 7.25 (d, 1H)

Step J

The title compound from Example 8 Step B (0.090 g, 0.238 mmol) and the title compound from Step I above (0.075 g, 0.27 mmol) were dissolved in toluene (4.25 mL) and treated with 2,2-bis-(diphenylphosphino)-1,1-naphthalene (0.032 g, 0.048 mmol) and sodium tert-butylate (0.061 g, 0.65 mmol). The reaction mixture was then degassed by bubbling argon through the reaction mixture followed by the addition of tris(dibenzylideneacetone)dipalladium chloroform complex (0.021 g, 0.024 mmol). The reaction vessel was sealed and the mixture was heated at ~110° C. in a sand bath for 45 minutes. The reaction mixture was diluted with ethyl acetate (20 mL), water (5 mL) and brine (5 mL). The organic phase was separated, dried over Na$_2$SO$_4$, filtered and the solvents were removed. The residue was purified by chromatography on silica using ethylacetate/n-heptane (60/ 40) to afford the crude title compound. The crude material was again purified by chromatography on silica using ethylacetate/n-heptane (80/20) to afford the title compound as a yellow oil (0.58 g, 42%).

$^1$H-NMR (400 MHz, CDCl$_3$): d=1.40 (s, 9H), 1.52 (s, 9H), 1.86-1.92 (m, 2H), 2.67-2.71 (m, 2H), 2.93-2.99 (m, 2H), 3.10-3.17 (m, 2H), 3.68-3.73 (m, 2H), 3.73-3.80 (m, 2H), 4.23-4.27 (m, 2H), 6.40 (d, 1H), 6.68 (d, 1H), 6.80 (d, 1H), 7.06-7.09 (m, 1H), 7.12 (d, 1H), 7.23-7.29 (m, 2H), 7.50-7.56 (m, 1H), 8.50-8.53 (m, 1H)

Step K

The title compound from Step J above (0.058 g, 0.1 mmol) was dissolved in chloroform (1.6 mL) and treated with a 2 M solution of hydrogen chloride in diethylether (1.6 mL). The reaction mixture was stirred at room temperature overnight and the solvents were removed using a syringe. The solid material was dissolved in water (4 mL) and filtered through a 0.2 μm filter cartridge. The filtrate was collected and the solvent was evaporated to afford the title compound as a dark yellow glass (0.042 g, 86%).

$^1$H-NMR (400 MHz, D$_2$O): d=1.71-1.78 (m, 2H), 2.57-2.61 (m, 2H), 2.79-2.84 (m, 2H), 3.22-3.30 (m, 4H), 3.47-3.50 (m 2H), 3.59-3.63 (m, 2H), 5.80 (d, 1H), 6.44 (d, 1H), 7.33 (d, 1H), 7.42-7.83 (m, 4H), 8.35 (t, 1H), 8.51 8d, 1H)

MS (ESI); m/z=375.29 (MH+)

Preparation Example 10 (Compound 10)

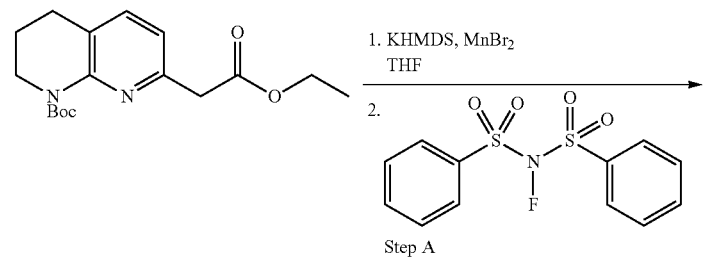

Step A

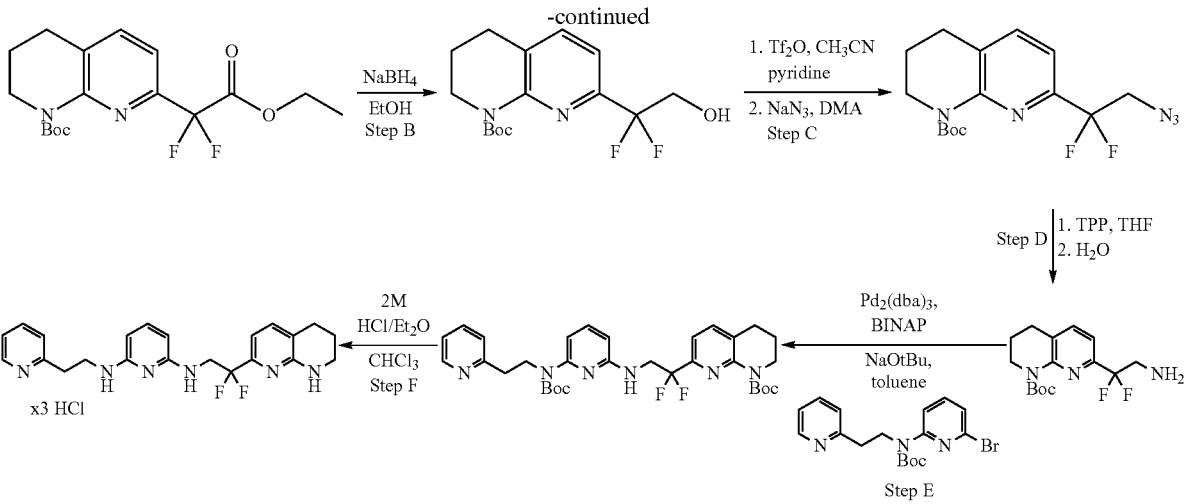

Step A

Potassium bis(trimethylsilyl)amide (5.99 g, 30 mmol) was dissolved in tetrahydrofuran (90 mL) and the solution was cooled to −78° C. At −78° C. the title compound from Example 9 Step E (3.2 g, 10 mmol) was added in one portion and the mixture was stirred at −78° C. for 45 minutes. Manganese(II)bromide (4.3 g, 20 mmol) was added in one portion and stirring at −78° C. was continued for 30 minutes. Then N-fluorobenzenesulfonimide (8.9 g, 28.2 mmol) was added at −78° C. in one portion. The mixture was stirred at −78° C. for 30 minutes and allowed to warm to room temperature overnight. The mixture was diluted with saturated sodium bicarbonate (250 mL) and ethylacetate (300 mL). The organic phase was separated, dried over $Na_2SO_4$, filtered and the solvents were removed. The residue was purified by chromatography on silica using ethyl acetate/n-heptane (40/60) to afford the title compound as a pale orange oil (2.15 g, 60%).

$^1$H-NMR (400 MHz, $CDCl_3$): d=1.30 (m, 3H), 1.50 (s, 9H), 1.88-1.96 (m, 2H), 2.77-2.82 (m, 2H), 3.73-3.78 (m, 2H), 4.30-4.36 (m, 2H), 7.31-7.34 (m, 1H), 7.48-7.51 (m, 1H)

Step B

The title compound from Step A above (2.15 g, 6 mmol) was dissolved in ethanol (8 mL) and the mixture was cooled to 0° C. Then sodium borohydride (0.23 g, 6 mmol) was added in portions over a period of 10 minutes. After the addition was completed, the mixture was stirred overnight and allowed to reach room temperature The mixture was diluted with ethylacetate (80 mL), water (10 mL) and 10% citric acid solution (5 mL). The organic phase was separated, dried over $Na_2SO_4$, filtered and the solvents were removed. The residue was purified by chromatography on silica using ethylacetate/n-heptane (40/60) to afford the title compound as an off white solid (1.08 g, 57%).

$^1$H-NMR (400 MHz, $CDCl_3$): d=1.50 (s, 9H), 1.92-1.98 (m, 2H), 2.76-2.80 (m, 2H), 3.77-3.82 (m, 2H), 4.14 (t, 2H), 5.28 (br-s, 1H), 7.30-7.38 (m, 1H), 7.52-7.56 (m, 1H)

Step C

The title compound from Step B above (1.08 g, 3.44 mmol) was dissolved in acetonitrile (6 mL) and pyridine (0.36 mL, 5.4 mmol) was added. The mixture was cooled to 0° C. and trifluoromethanesulfonic acid anhydride (0.63 mL, 3.77 mmol) was added dropwise. After the addition was completed, the mixture was stirred at 0° C. for 30 minutes. The mixture was diluted with diethylether (100 mL) and washed with 10% citric acid (10 mL) and brine (10 mL). The organic phase was separated, dried over $Na_2SO_4$, filtered and the solvents were removed to afford the crude triflate as an orange oil. The crude triflate was dissolved in N,N'-dimethylacetamide (7.5 mL) and sodium azide (1.1 g, 17.2 mmol) was added. The mixture was heated at ~75° C. in a sand bath for 3 h. The mixture was diluted with diethylether (100 mL) and washed with water (20 mL) and brine (20 mL). The organic phase was separated, dried over $Na_2SO_4$, filtered and the solvents were removed. The residue was purified by chromatography on silica using ethylacetate/n-heptane (30/70) to afford the title compound as a pale yellow oil, which becomes a solid by standing at room temperature (0.87 g, 742%).

$^1$H-NMR (400 MHz, $CDCl_3$): d=1.50 (s, 9H), 1.92-1.98 (m, 2H), 2.79 (t, 2H), 3.78 (t, 2H), 3.97 (t, 2H), 7.36 (d, 1H), 7.51 (d, 1H)

Step D

The title compound from Step C above (0.87 g, 2.58 mmol) was dissolved in tetrahydrofuran (10 mL) and triphenylphosphine (0.81 g, 3.1 mmol) was added. The reaction mixture was stirred at room temperature for 20 h and then water (10 mL) was added. Stirring was continued overnight and the solvents were removed in vacuo. The residue was purified by chromatography on silica using dichloromethane/methanol (98/2) followed by dichloromethane/methanol (95/5) to afford the crude title compound. The crude material was again purified by chromatography on silica using dichloromethane/methanol (99/1) followed by dichloromethane/methanol (9/1) to afford the title compound as a yellow liquid, which becomes a solid/wax by standing at room temperature (0.79 g, 98%). The title compound contains traces of triphenylphosphineoxide.

$^1$H-NMR (400 MHz, $CDCl_3$): d=1.50 (s, 9H), 1.70 (br-s, 2H), 1.90-1.97 (m, 2H), 2.74-2.79 (m, 2H), 3.40 (t, 2H), 3.74-3.79 (m, 2H), 7.31 (d, 1H), 7.48 (d, 1H)

Step E

The title compound from Example 8 Step B (0.09 g, 0.238 mmol) and the title compound from Step D above (0.085 g, 0.27 mmol) were dissolved in toluene (4.25 mL) and treated with 2,2-bis-(diphenylphosphino)-1,1-naphthalene (0.032 g, 0.048 mmol) and sodium tert-butylate (0.061 g, 0.65 mmol). The reaction mixture was then degassed by bubbling argon through the reaction mixture followed by the addition of tris(dibenzylideneacetone)dipalladium chloroform complex (0.021 g, 0.024 mmol). The reaction vessel was sealed and the mixture was heated at ~115° C. in a sand bath for 45 minutes. The reaction mixture was diluted with ethyl acetate (20 mL), water (5 mL) and brine (5 mL). The organic phase was separated, dried over Na$_2$SO$_4$, filtered and the solvents were removed. The residue was purified by chromatography on silica using ethylacetate/n-heptane (40/60) to afford the title compound as a dark yellow wax (0.62 g, 43%).

$^1$H-NMR (400 MHz, CDCl$_3$): d=1.42 (s, 9H), 1.57 (s, 9H), 1.92-1.98 (m, 2H), 2.76-2.80 (m, 2H), 3.13-3.18 (m, 2H), 3.77-3.82 (m, 2H), 4.22-4.32 (m, 4H), 6.38 (d, 1H), 6.52 (br-s, 1H), 6.82 (d, 1H), 7.06-7.09 (m, 1H), 7.17-7.20 (m, 1H), 7.26-7.31 (m, 2H), 7.47-7.56 (m, 2H), 8.51 (m, 1H)

Step F

The title compound from Step E above (0.06 g, 0.1 mmol) was dissolved in chloroform (1.6 mL) and treated with a 2 M solution of hydrogen chloride in diethylether (1.6 mL). The reaction mixture was stirred at room temperature overnight and the solvents were removed using a syringe. The solid material was dissolved in water (4 mL) and filtered through a 0.2 lam filter cartridge. The filtrate was collected and the solvent was evaporated to afford the title compound as a dark yellow glass (0.039 g, 74%).

$^1$H-NMR (400 MHz, D$_2$O): d=1.73-1.81 (m, 2H), 2.67-2.71 (m, 2H), 3.23-3.28 (m, 2H), 3.32-3.38 (m, 2H), 3.62-3.67 (m, 2H), 3.97 (t, 2H), 5.90-5.93 (m, 1H), 6.80-6.83 (m, 1H), 7.44-7.83 (m, 5H), 8.38 (t, 1H), 8.50-8.53 (m, 1H)

MS (ESI); m/z=411.45 (MH$^+$)

Preparation Example 11 (Compound 12)

in a sand bath overnight. The mixture was diluted with ethyl acetate (60 mL) and a solution of potassium dihydrogenphosphate (8.58 g, 63 mmol) in water (50 mL) was added. The mixture was stirred at room temperature for 30 minutes and filtered. The precipitate was washed with ethyl acetate (30 mL) and the organic phase was separated from the filtrate. The organic phase was washed with water (2 ×20 mL), dried over Na$_2$SO$_4$, filtered and the solvents were removed. The residue was purified by chromatography on silica using ethylacetate/n-heptane (20/80) to afford the title compound as a yellow oil (3.17 g, 55%).

$^1$H-NMR (400 MHz, CDCl$_3$): d=1.33 (t, 3H), 4.38 (q, 2H), 7.40-7.45 (m, 1H), 7.72 (d, 1H), 7.86 (t, 1H), 8.66 (d, 1H)

Step B

The title compound from Step A above (3.17 g, 15.8 mmol) was dissolved in ethanol (18 mL) and the flask was surrounded by a water-bath. Then sodium borohydride (0.6 g, 16 mmol) was added in portions over a period of 10 minutes. After the addition was completed, the mixture was stirred at room temperature for 90 minutes. The mixture was diluted with ethylacetate (60 mL) and a 10% citric acid solution was added until the foaming of the mixture stopped. Additional water (25 mL) was added and the organic phase was separated, dried over Na$_2$SO$_4$, filtered and the solvents were removed. The residue was purified by chromatography on silica using dichloromethane/methanol (95/5) to afford the title compound as an off white solid (2 g, 79%).

$^1$H-NMR (400 MHz, CDCl$_3$): d=3.52 (br-s, 1H), 4.23 (t, 2H), 7.40-7.45 (m, 1H), 7.72 (d, 1H), 7.87 (t, 1H), 8.61 (d, 1H)

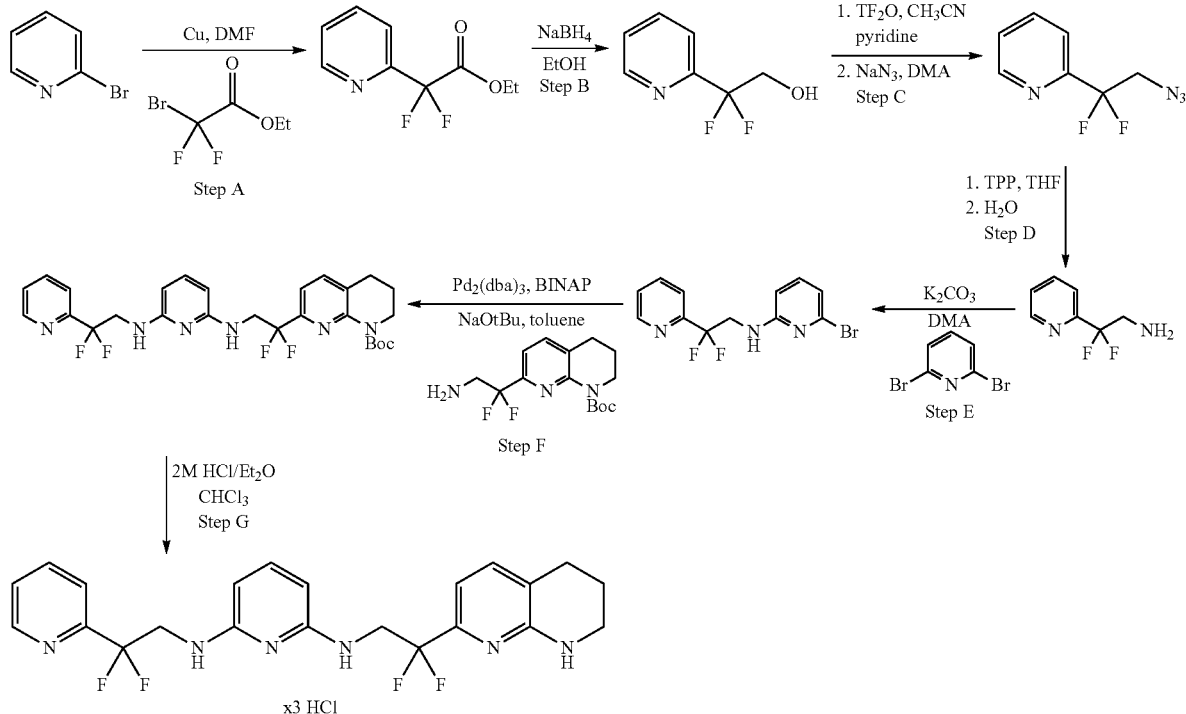

Step A

Copper powder (4.5 g, 70.8 mmol) was suspended in N,N'-dimethylformamide (22.5 mL) and 2-bromopyridine (4.5 g, 28.5 mmol) and 2-bromo-2,2-difluoroacetate (6 g, 29.6 mmol) was added. The mixture was heated at~72° C.

Step C

The title compound from Step B above (1.8 g, 11.3 mmol) was dissolved in acetonitrile (18 mL) and pyridine (1.18 mL, 17.8 mmol) was added. The mixture was cooled to 0° C. and trifluoromethanesulfonic acid anhydride (2.09 mL, 12.4 mmol) was added dropwise. After the addition was completed, the mixture was stirred at 0° C. for 30 minutes. The mixture was diluted with diethylether (200 mL) and washed with 10% citric acid (60 mL) and brine (60 mL). The organic phase was separated, dried over $Na_2SO_4$, filtered and the solvents were removed to afford the crude triflate as a brown oil. The crude triflate was dissolved in N,N'-dimethylacetamide (25 mL) and sodium azide (3.69 g, 56.7 mmol) was added. The mixture was heated at ~75° C. in a sand bath for 3 h. The mixture was diluted with diethylether (200 mL) and washed with 10% citric acid (60 mL) and brine (60 mL). The organic phase was separated, dried over $Na_2SO_4$, filtered and the solvents were removed. The residue was purified by chromatography on silica using ethylacetate/n-heptane (30/70) to afford the title compound as a colorless liquid (1.29 g, 62%).

$^1$H-NMR (400 MHz, $CDCl_3$): d=4.02 (t, 2H), 7.39-7.45 (m, 1H), 7.72 (d, 1H), 7.86 (t, 1H), 8.68 (d, 1H)

Step D

The title compound from Step C above (1.4 g, 7.6 mmol) was dissolved in tetrahydrofuran (30 mL) and triphenylphosphine (2.4 g, 9.1 mmol) was added. The reaction mixture was stirred at room temperature for 48 h and then water (15 mL) was added. Stirring was continued overnight and the solvents were removed in vacuo. The residue was purified by chromatography on silica using dichloromethane/methanol (98/2) followed by dichloromethane/methanol (95/5) to afford the title compound as a pale yellow liquid (1.05 g, 87%).

$^1$H-NMR (400 MHz, $CDCl_3$): d=1.42 (s, 2H), 3.42 (t, 2H), 7.35-7.40 (m, 1H), 7.68 (d, 1H), 7.82 (t, 1H), 8.65 (d, 1H)

Step E

Commercially available 2,6-dibromopyridine (0.5 g, 2.1 mmol) was dissolved in N,N'-dimethylacetamide (5 mL) and the title compound from Step D above was added (0.31 g, 2.1 mmol). After the addition of potassium bicarbonate (0.23 g, 2.3 mmol), the mixture was heated at ~145° C. in a sand bath for 8 h. The mixture was diluted with ethylacetate (100 mL) and was washed with water (30 mL) and brine (30 mL). The organic phase was separated, dried over $Na_2SO_4$, filtered and the solvents were removed. The residue was purified by chromatography on silica using ethylacetate/n-heptane (30/70) to afford the title compound as an orange oil (0.13 g, 20%).

$^1$H-NMR (400 MHz, $CDCl_3$): d=4.20 (dt, 2H), 5.08 (br-s, 1H), 6.42 (d, 1H), 6.71 (d, 1H), 7.20 (d, 1H), 7.35-7.39 (m, 1H), 7.66 (d, 1H), 7.79 (t, 1H), 8.63 (d, 1H)

Step F

The title compound from Step E above (0.12 g, 0.39 mmol) and the title compound from Example 10 Step D (0.14 g, 0.44 mmol) were dissolved in toluene (7 mL) and treated with 2,2-bis-(diphenylphosphino)-1,1-naphthalene (0.053 g, 0.078 mmol) and sodium tert-butylate (0.1 g, 1.06 mmol). The reaction mixture was then degassed by bubbling argon through the reaction mixture followed by the addition of tris(dibenzylideneacetone)dipalladium chloroform complex (0.035 g, 0.039 mmol). The reaction vessel was sealed and the mixture was heated at ~115° C. in a sand bath for 45 minutes. The reaction mixture was diluted with ethyl acetate (20 mL), water (5 mL) and brine (5 mL). The organic phase was separated, dried over $Na_2SO_4$, filtered and the solvents were removed. The residue was purified by chromatography on silica using dichloromethane/acetone (95/5) to afford the crude title compound. The crude material was again purified by chromatography on silica using ethylacetate/n-heptane (50/50) to afford the title compound as a dark yellow oil (0.62 g, 29%).

$^1$H-NMR (400 MHz, $CDCl_3$): d=1.56 (s, 9H), 1.90-1.97 (m, 2H), 2.74-2.80 (m, 2H), 3.78-3.82 (m, 2H), 4.13-4.27 (m, 4H), 4.50 (br-s, 1H), 5.68-5.70 (m, 1H), 5.92-5.98 (m, 2H), 7.10 (t, 1H), 7.26-7.32 (m, 2H), 7.45-7.50 (m, 1H), 7.63-7.68 (m, 1H), 7.73-7.79 (m, 1H), 8.63-8.67 (m, 1H)

Step G

The title compound from Step F above (0.06 g, 0.11 mmol) was dissolved in chloroform (1.6 mL) and treated with a 2 M solution of hydrogen chloride in diethylether (1.6 mL). The reaction mixture was stirred at room temperature overnight and the solvents were removed using a syringe. The solid material was dissolved in water (4 mL) and filtered through a 0.2 μm filter cartridge. The filtrate was collected and the solvent was evaporated to afford the title compound as a dark yellow glass (0.048 g, 77%).

$^1$H-NMR (400 MHz, $D_2O$): d=1.71-1.78 (m, 2H), 2.63-2.69 (m, 2H), 3.30-3.36 (m, 2H), 3.90-4.02 (m, 4H), 5.81-8.48 (m, 9H)

MS (ESI); m/z=447.38 (MH$^+$)

Preparation Example 12 (Compound 11)

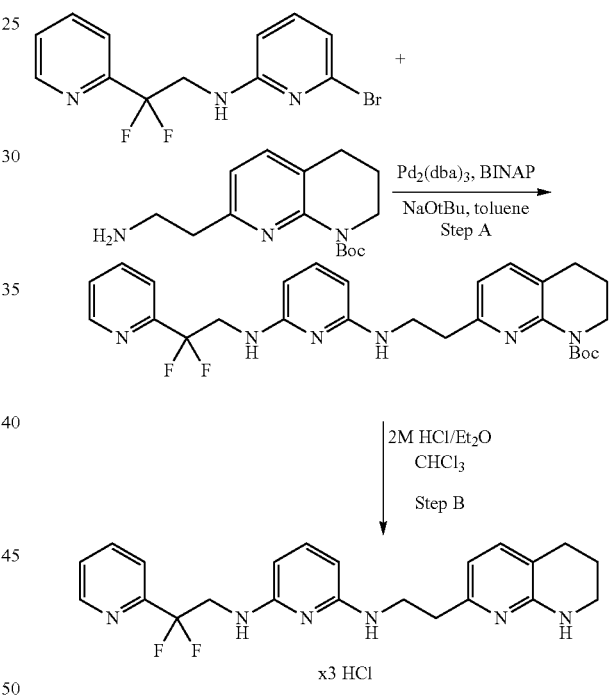

Step A

The title compound from Example 11 Step E (0.13 g, 0.42 mmol) and the title compound from Example 9 Step I (0.13 g, 0.48 mmol) were dissolved in toluene (7.6 mL) and treated with 2,2-bis-(diphenylphosphino)-1,1-naphthalene (0.058 g, 0.084 mmol) and sodium tert-butylate (0.11 g, 1.15 mmol). The reaction mixture was then degassed by bubbling argon through the reaction mixture followed by the addition of tris(dibenzylideneacetone)dipalladium chloroform complex (0.038 g, 0.042 mmol). The reaction vessel was sealed and the mixture was heated at ~115° C. in a sand bath for 45 minutes. The reaction mixture was diluted with ethyl acetate (20 mL), water (5 mL) and brine (5 mL). The organic phase was separated, dried over $Na_2SO_4$, filtered and the solvents were removed. The residue was purified by chromatography on silica using ethylacetate/n-heptane (70/30) to afford the crude title compound. The crude material was again purified by chromatography on silica using ethylacetate/n-heptane (70/30) to afford the title compound as a grey foam (0.07 g, 32%).

$^1$H-NMR (400 MHz, CDCl$_3$): d=1.54 (s, 9H), 1.86-2.04 (m, 2H), 2.66-2.74 (m, 2H), 2.93-3.08 (m, 2H), 3.48-3.66 (m, 2H), 3.72-3.80 (m, 2H), 4.18 (t, 2H), 4.5 (br-s, 1H), 5.65-5.98 (m, 2H), 6.21-6.40 (m, 1H), 6.76-6.83 (m, 1H), 7.10 (t, 1H), 7.25-7.36 (m, 2H), 7.61-7.68 (m, 1H), 7.72-7.77 (m, 1H), 8.60-8.64 (m, 1H)

Step B

The title compound from Step A above (0.07 g, 0.14 mmol) was dissolved in chloroform (2 mL) and treated with a 2 M solution of hydrogen chloride in diethylether (2 mL). The reaction mixture was stirred at room temperature overnight and the solvents were removed using a syringe. The solid material was dissolved in water (4 mL) and filtered through a 0.2 lam filter cartridge. The filtrate was collected and the solvent evaporated to afford the title compound as a dark yellow glass (0.063 g, 88%).

$^1$H-NMR (400 MHz, D$_2$O): d=1.63-1.75 (m, 2H), 2.44-2.59 (m, 2H), 2.73-2.85 (m, 2H), 3.18-3.28 (m, 2H), 3.41-3.49 (m, 2H), 3.93 (t, 2H), 5.73-5.80 (m, 1H), 6.38-6.43 (m, 1H), 7.25-7.50 (m, 4 H), 7.61-7.65 (m, 1H), 7.85-7.90 (m, 1H), 8.42-8.48 (m, 1H)

MS (ESI); m/z=411.45 (MH$^+$)

Preparation Example 13 (Compound 8)

Compound 8 was prepared as described in WO2008/061795.

Experimental results

Method for measuring the solubility:
1. Materials, Reagents & Equipment
Plate shaker, Centrifuge (Eppendorf, 8 cm radius), HPLC (Dionex P580), Column: Agilent Zorbax Eclipse XDB-C18 rapid resolution (4.6×50 mm, 3.5 mM, Agilent), Uncoloured microtubes 1.5 mL (Eppendorf, 1.5 mL), Micropipettes 100-1000 mL, Micropipettes 10-100 mL, Dulbecco's phosphate buffer, DMSO, ammonium formate, formic acid 98-100%, UP-H$_2$O, acetonitrile HPLC grade, methanol GR analysis, PVDF membrane filter.
2. Method
2.1 Preparation of PBS 5× (Stored at 4° C.) and PBS1× for Analysis
PBS 5×
Dissolved the full content of PBS salt (D-5652-10L) in 2 L of UP-H$_2$O.
PBS1×
Before analysis, dilute 5 fold the PBS 5× in order to prepare 30 mL of PBS1× and filter the solution using a syringe and any hydrophilic membrane e.g. PVDF membrane.

2.2 Preparation of HPLC Solvent (Stored at RT)
Solvent A: 13.3 mM ammonium formate/6.5 mM formic acid/UP-water
Dissolve 820±1 mg of ammonium formate and 245 μL of formic acid in 1000 mL of UP-H$_2$O.
Solvent B: 6.0 mM ammonium formate/2.9 mM formic acid/90% acetonitrile/10% UP-water
Dissolve 378±1 mg of ammonium formate and 110 μL of formic acid in 900 mL acetonitrile and 100 mL of UP-H$_2$O.
2.3 Preparation of the Stock Solution of the Compound
Dissolve compound in DMSO at a concentration of 25 mM (minimum 50 mL).
2.4 Preparation of Standard Curve
Prepare 15 mL of methanol/H$_2$O (6/4).
Prepare 5 standard calibrators: 250 μM, 200 μM, 50 μM, 12.5 μM and 3.13 μM in methanol/H$_2$O (6/4).
Make preparations of each standard concentration in 1.5 microtubes.

| | Concentration [mM] | | | | | |
|---|---|---|---|---|---|---|
| | 250 | 200 | 50 | 12.5 | 3.13 | Blank |
| | Microtubes # | | | | | |
| | 1 | 2 | 3 | 4 | 5 | 6 |
| Methanol/H$_2$O (6/4) | 392 μL | 392 μL | 294 μL | 294 μL | 294 μL | 294 μL |
| DMSO | 4 μL | 4.8 μL | 6 μL | 6 μL | 6 μL | 6 μL |
| 25 mM DMSO Stock Compound | 4 μL | 3.2 μL | — | — | — | — |
| 200 mM Standard (from #2) | — | — | 100 μL | — | — | — |
| 50 mM Standard (from #3) | — | — | — | 100 μL | — | — |
| 12.5 mM Standard (from #4) | — | — | — | — | 100 μL | — |

Transfer directly 250-300 μL from each microtube to an HPLC vial.
Run HPLC (from microtubes #6 to #1), using the following conditions:
C18 column, 0.7 mL/min, 20° C., UV detection at 254 nm, volume injection: 20 μL and one of the following gradients:
Gradient for Very Polar/Hydrophilic Compounds

| Time [min] | Flowrate [mL/min] | % A | % B |
|---|---|---|---|
| 0 | 0.7 | 100 | 0 |
| 2.5 | 0.7 | 75 | 25 |
| 5 | 0.7 | 55 | 45 |
| 6 | 0.7 | 35 | 65 |
| 7 | 0.7 | 15 | 85 |
| 8 | 0.7 | 0 | 100 |
| 9 | 0.7 | 0 | 100 |
| 9.1 | 0.7 | 100 | 0 |
| 12.0 | 0.7 | 100 | 0 |

Gradient for Less Polar/Lipophilic Compounds

| Time [min] | Flowrate [mL/min] | % A | % B |
|---|---|---|---|
| 0 | 0.7 | 100 | 0 |
| 5 | 0.7 | 10 | 90 |
| 6 | 0.7 | 5 | 95 |
| 9 | 0.7 | 0 | 100 |
| 9.1 | 0.7 | 100 | 0 |
| 12 | 0.7 | 100 | 0 |

2.5. Preparation of the Sample for Aqueous Solubility
Prepare Samples of the Compound in Triplicates

| Concentration [mM] | 200 μM | Blank |
|---|---|---|
| PBS 1x | 392 μL | 294 μL |
| DMSO | 4.8 μL | 6 μL |
| 25 mM DMSO Stock compound | 3.2 μL | — |

Shake it gently (350 rpm) for 24 hours at room temperature.
After the incubation time, centrifuge at 2500 g (5500 rpm) for 30 min.
Sample 200 μL of supernatant for HPLC analysis using the same conditions described in 2.4.

2.6. Data Treatment
Integrate area of each standard point peak at 254 nm.
Determine the standard curve for the compound by plotting the area vs. the theoretical concentration. Establish the standard curve equation based on a linear regression (with an intercept at 0, $R^2 \geq 0.90$).

$$y_{(area)} = \text{slope} \times x_{(concentration)}$$

Calculate the average area of each triplicate prepared in aqueous phase.
The concentration of the compound in the supernatant is determined by the following formula:

$$x_{(concentration)} = \left( \frac{y_{(average\cdot Area)}}{slope_{(STD\text{-}curve)}} \right) [\mu M]$$

The solubility of the compound is determined by the following formula:

$$\text{Aqueous Solubility} = \left( \frac{M_{w(freebase)} \cdot x_{(concentration)}}{1000} \right) [mg/L]$$

Example

Inhibition of Amyloid Beta (Ab) 1-42 Peptide Aggregation (ThT Assay)

A number of small molecules were tested for their capacity to inhibit the aggregation of amyloid beta (Ab) 1-42 peptide using a thioflavin T spectrofluorescence assay.
Preparation of Ab Peptide Film
Ab1-42 lyophilized powder (Bachem) was reconstituted in hexafluoroisopropanol (HFIP) to 1 mM. The peptide solution was sonicated for 15 min at room temperature, agitated overnight, and aliquots were placed in non-siliconized microcentrifuge tubes. The HFIP was then evaporated under a stream of argon. The resulting peptide film was dried under vacuum for 10 min, tightly sealed and stored at −80° C. until used.
Inhibition of Ab1-42 Aggregation
To assay for the small molecule-mediated inhibition of Ab1-42 aggregation, the small molecules were dissolved previous to each experiment in anhydrous dimethyl sulfoxide (DMSO, Sigma-Aldrich) to reach a concentration of 7.4 mM. Ab1-42 peptide film was dissolved in DMSO to reach 400 μM. Assay solution in PBS buffer was prepared in non-siliconized incubation tubes to reach the following concentrations: 330 mM small molecule, 33 mM Ab1-42, 10 μM thioflavin T (ThT), and 12.8% DMSO. Therefore, the final molar ratio of small molecule to Ab1-42 was 10:1. A positive control without a small molecule was prepared to measure maximum RFU. A negative control without Ab1-42 was prepared for each small molecule. 3-Aminopyrazole trimer (Trimer) was tested in all assays to ascertain reproducibility between independent experiments. The solutions were incubated for 24 hrs at 37° C., and the spectrofluorescence (relative fluorescence units; RFU) read in six replicates in black 384-well assay plates (Perkin-Elmer) on a Perkin-Elmer FluoroCount spectrofluorometer. Inhibition of aggregation is expressed as mean % inhibition or ±1 standard deviation (SD) according to the following equation:

% inhibition=(RFU of positive control−RFU of negative control)−(RFU of sample with Aβ-42−RFU of sample without Aβ1-42)×100

(RFU of positive control−RFU of negative control)
Cut-off criteria for selection of functional molecules were defined at 50% inhibition capacity. Molecules showing an inhibition capacity over 70% were considered as very strong candidates.
To determine the $IC_{50}$, the following dilutions of the compounds were used in the ThT assay describe above: 330 μM, 82.50 μM, 20.63 μM, 5.16 μM, 1.29 μM, 0.32 μM and 0.08 μM Example Effect of a Compound of the Invention in a Rat Model of Chronic Ocular Hypertension/Glaucoma A rat model of chronic ocular hypertension (OHT)/glaucoma was created by injecting hypertonic saline into the episcleral veins of one eye of Dark Agouti rats. 18 rats received an intra-vitreal injection containing a volume of 5 μL of compound 1 (ACI-260) at a concentration of 74 mg/L in the OHT eye. 18 rats served as negative control and received 5 μl of saline and 18 rats served as positive control and received 6 μL Congo Red (1.46 mg/mL). 6 animals/timepoint were euthanized at 3, 8 and 16 weeks after treatment.
Intraocular pressure (IOP) was measured using a Tonopen once every 4 weeks post dosing and prior to sacrifice (within 3 days). 5 to 7 days prior to sacrifice, animals were injected intra-cerebrally with 5 μL of 4% FluoroGold to label the retinal ganglion cells (RGCs). In order to quantify viable RGCs, images were processed using a specific system of image analysis software and viable RGCs were expressed per square millimeter.
At 3 weeks, a reduction of intraocular pressure was not observed in any of the animals. However, the number of viable RGCs was significantly increased in the group treated with compound 1 ($p<0.001$) and in the Congo Red group ($p<0.001$) in comparison to the control group. At 8 and 16 weeks, these results were confirmed, suggesting that compound 1 is neuroprotective. The results are shown in FIG. 1.

| Comp. | | $IC_{50}$ ThT-assay* [mM] | Solubility [mM] [mg/L] |
|---|---|---|---|
| 1 | [structure: pyridyl-CH2CH2-NH-pyridyl-CH2CH2-NH-pyridyl-NH-CH3, x 3 HCl] | 25.5 μM | 857 μM / 298 mg/L |

| Comp. | | IC$_{50}$ ThT-assay* [mM] | Solubility [mM] [mg/L] |
|---|---|---|---|
| 2 | 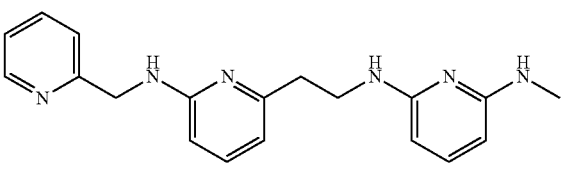 x 3 HCl | 12.9 μM | — |
| 3 | 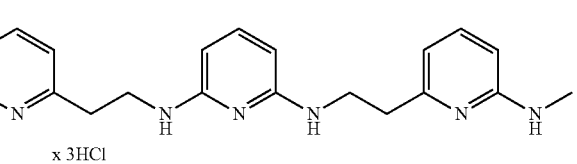 x 3HCl | 35.3 μM | 206 μM<br>71 mg/L |
| 4 | 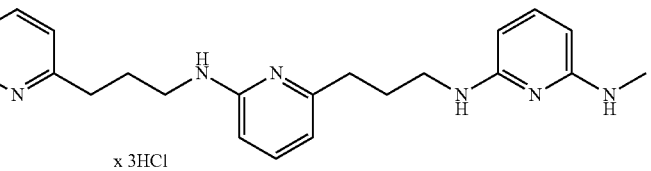 x 3HCl | 16.5 μM | 103 μM<br>38 mg/L |
| 5 | 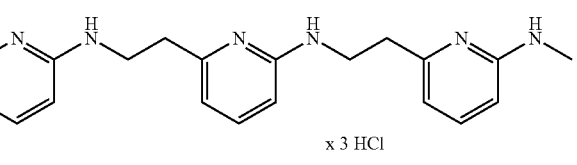 x 3 HCl | 140 μM | |
| 13 | 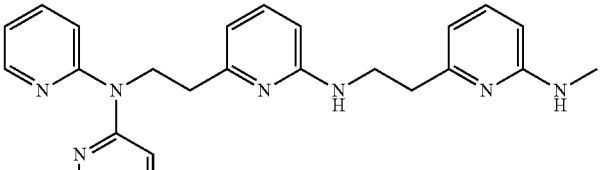 x 3 HCl | 298 μM | |

*mean of 2 experiments

As can be seen by comparing the results obtained with the compounds according to the invention (compounds 1, 2, 3 and 4), the longer linker decreases the solubility.

Compound 5 (not according to the invention) does not have a 2,6-diaminopyridine moiety. As can be seen, the biological activity is significantly decreased.

| Comp. | | ThT assay at 330 mM % inhib. | ThT assay at 330 mM % inhib. | Mean % inhib. | Solubility [mM] [mg/L] |
|---|---|---|---|---|---|
| 1 | 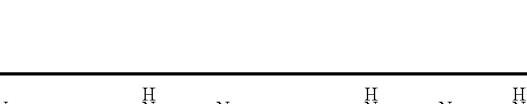 x 3 HCl | 88.8 | 79.6 | 84.2 | 857 μM<br>298 mg/L |
| 6 | 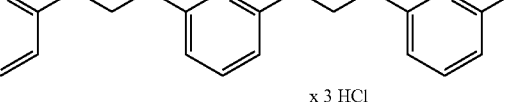 x 2HCl | 68.4 | 59.0 | 63.7 | |

| Comp. | ThT assay at 330 mM % inhib. | ThT assay at 330 mM % inhib. | Mean % inhib. | Solubility [mM] [mg/L] |
|---|---|---|---|---|
| 7 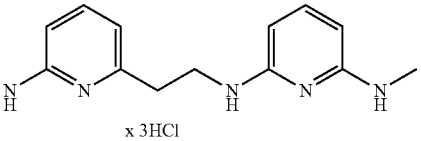 | 77.6 | 70.3 | 74.0 | 195 µM 50 mg/L |
| 8 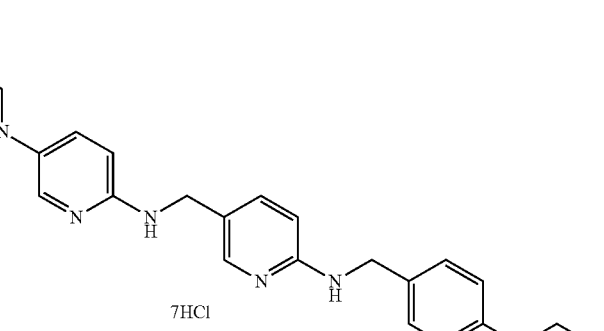 | 73.3 | 80.7 | 77.0 | 1.0 µM 0.4 mg/L |
| 9 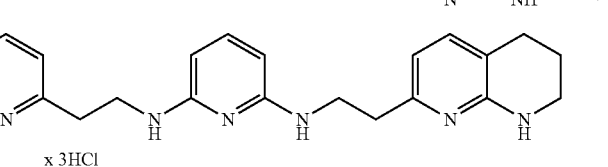 | 91.8 | 93.4 | 92.6 | 154 µM 57 mg/L |
| 10 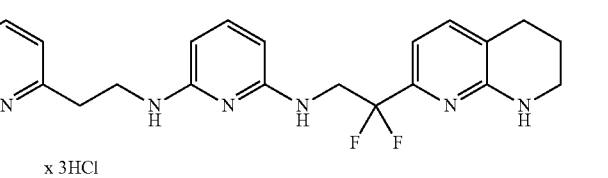 | 89.6 | 77.6 | 83.6 | |
| 11 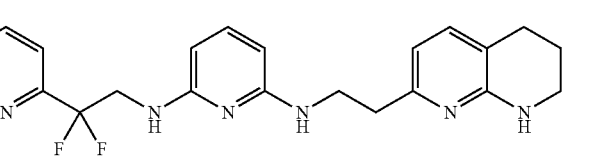 | 95.3 | 94.4 | 94.9 | 119 µM 48 mg/L |
| 12 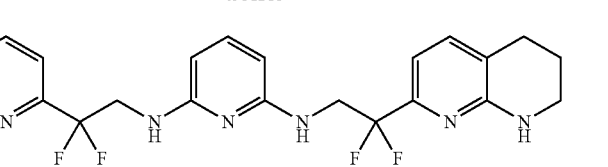 | 56.4 | 63.7 | 60.0 | 21.5 µM 9.5 mg/L |

Compound 6 (not according to the invention) only has two pyridine rings. Compound 7 (not according to the invention) only has two pyridine rings. Both of these compounds have significantly reduced activity compared to compound 1 (according to the invention).

The solubility of compound 8 (not according to the invention), which has a 2,5-diaminopyridine moiety, is significantly worse than that of compound 1 (according to the invention), which has a 2,6-diaminopyridine moiety.

Compounds 9, 10, and 11 have comparable activity to compound 1 but their solubility is worse. Only for compound 12 both solubility and activity are worse when compared to compound 1.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the invention.

We claim:

1. A method of inhibiting, treating, or alleviating the effects of glaucoma, comprising; administering to a subject in need thereof an effective amount of a compound having the formula (I)

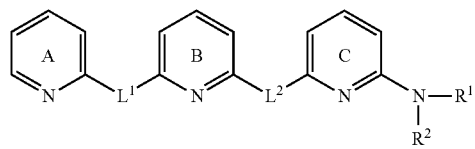

(I)

wherein $L^1$ and $L^2$ are independently selected from moieties having the formula (a) or (b)

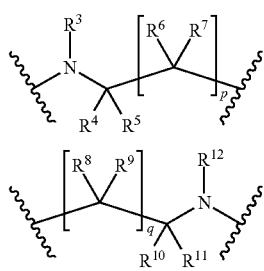

wherein at least one of $L^1$ or $L^2$ has the formula (b);
$R^1$ and $R^2$ are independently selected from the group consisting of hydrogen, and C1-6-alkyl;
$R^3$, $R^4$, $R^5$, $R^6$, $R^7$, $R^8$, $R^9$, $R^{10}$, $R^{11}$, and $R^{12}$ are hydrogen;
p is 1 or 2; and
q is 0, 1 or 2,
or a pharmaceutically acceptable salt thereof.

2. The method of claim 1, wherein the glaucoma is selected from chronic (idiopathic) open-angle glaucoma, pupillary block glaucoma, developmental glaucoma, glaucoma associated with other ocular disorders, glaucoma associated with elevated episcleral venous pressure, glaucoma associated with inflammation and trauma, glaucoma following intraocular surgery, high-pressure glaucoma, normal-pressure glaucoma, acute angle-closure glaucoma, subacute angle-closure glaucoma, chronic angle-closure glaucoma, combined mechanism glaucoma, congenital (infantile) glaucoma, juvenile glaucoma aniridia, glaucoma associated with disorders of the corneal endothelium, glaucoma associated with disorders of the iris and ciliary body, glaucoma associated with disorders of the lens, glaucoma associated with disorders of the retina, choroid, and vitreous, glaucoma associated with retinal detachment and vitreoretinal abnormalities, neovascular glaucoma, pigmentary glaucoma, exfoliation syndrome, lens-induced open-angle glaucoma, glaucoma associated with lens intumescence and dislocation, glaucoma associated with keratitis, episcleritis, and scleritis, ciliary block (malignant) glaucoma, glaucoma in aphakia and pseudophakia, epithelial, fibrous, and endothelial proliferation, glaucoma associated with corneal surgery, and glaucoma associated with vitreoretinal surgery or a combination thereof.

3. The method of claim 1, wherein $R^1$ and $R^2$ are independently selected from hydrogen and methyl.

4. The method of claim 1, wherein q is 2.

5. The method of claim 1, wherein the compound is selected from

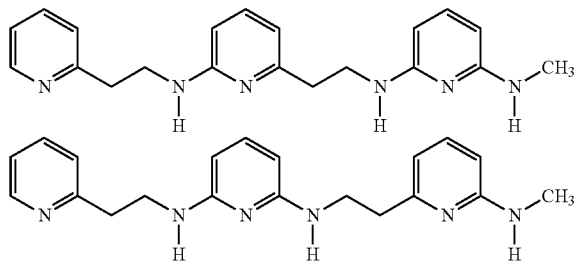

or a pharmaceutically acceptable salt thereof.

6. The method of claim 1, wherein the compound is

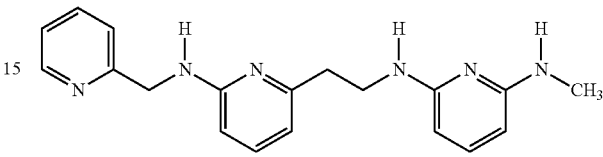

or a pharmaceutically acceptable salt thereof.

7. The method of claim 1, wherein the compound is

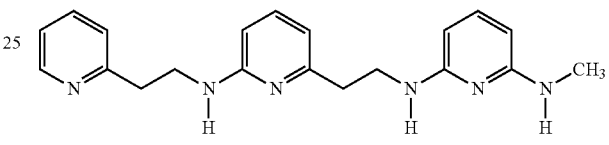

or a pharmaceutically acceptable salt thereof.

8. The method of claim 1, wherein the compound is

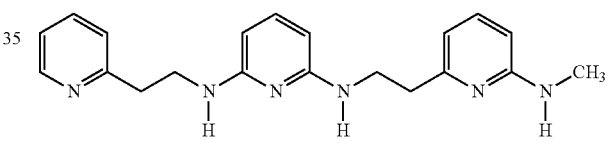

or a pharmaceutically acceptable salt thereof.

\* \* \* \* \*

UNITED STATES PATENT AND TRADEMARK OFFICE
CERTIFICATE OF CORRECTION

PATENT NO. : 9,701,660 B2
APPLICATION NO. : 14/502907
DATED : July 11, 2017
INVENTOR(S) : Heiko Kroth et al.

It is certified that error appears in the above-identified patent and that said Letters Patent is hereby corrected as shown below:

At Column 13, Line 46, italicize "in situ";

At Column 27, Line 40, insert the missing -- N -- at the chemical compound "C";

At Column 28, Line 10, insert the missing -- N -- at the chemical compound "C";

At Column 34, Line 67, italicize "in situ";

At Column 44, Line 32, italicize "in vacuo";

At Column 56, Line 42, italicize "in vacuo";

At Column 57, Line 42, change "1am" to the symbol for micrometer - µm -;

At Column 72, Line 47, italicize "in vacuo";

At Column 73, Line 22, change "1am" to the symbol for micrometer - µm -;

At Column 75, Line 25, italicize "in vacuo"; and

At Column 77, Line 18, change "1am" to the symbol for micrometer - µm -.

Signed and Sealed this
Third Day of October, 2017

Joseph Matal
*Performing the Functions and Duties of the*
*Under Secretary of Commerce for Intellectual Property and*
*Director of the United States Patent and Trademark Office*